US009651559B2

(12) United States Patent
Himmler et al.

(10) Patent No.: US 9,651,559 B2
(45) Date of Patent: *May 16, 2017

(54) DISPLAY OF BINDING AGENTS

(71) Applicant: F-star Biotechnologische Forschungs-und Entwicklungsges.m.b.H, Vienna (AT)

(72) Inventors: Gottfried Himmler, Gross-Enzersdorf (AT); Geert Mudde, Breitenfurt (AT); Gerda Redl, Gross-Enzersdorf (AT); Florian Ruker, Vienna (AT); Gordana Wozniak-Knopp, Vienna (AT)

(73) Assignee: F-star Biotechnologische Forschungs— und Entwicklungsges.m.b.H, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/556,662

(22) Filed: Dec. 1, 2014

(65) Prior Publication Data

US 2015/0153359 A1 Jun. 4, 2015

Related U.S. Application Data

(63) Continuation of application No. 12/666,618, filed as application No. PCT/AT2008/000232 on Jun. 26, 2008, now Pat. No. 8,921,279.

(Continued)

(51) Int. Cl.
*C40B 30/04* (2006.01)
*G01N 33/68* (2006.01)
(Continued)

(52) U.S. Cl.
CPC ....... *G01N 33/6857* (2013.01); *C07K 16/005* (2013.01); *C07K 16/32* (2013.01);
(Continued)

(58) Field of Classification Search
None
See application file for complete search history.

(56) References Cited

U.S. PATENT DOCUMENTS

| 5,223,409 A | 6/1993 | Ladner et al. ............... 435/69.7 |
| 5,395,750 A | 3/1995 | Dillon et al. ..................... 435/5 |

(Continued)

FOREIGN PATENT DOCUMENTS

| AU | 2006/204459 B2 | 1/2006 | ............. C07K 16/00 |
| AU | 2005/289685 A1 | 4/2006 | ............. A61K 47/48 |

(Continued)

OTHER PUBLICATIONS

Braren et al. (Mar. 21, 2007) Biotechnol Appl Biochem vol. 47 pp. 205 to 214.*

(Continued)

*Primary Examiner* — Christian Boesen
(74) *Attorney, Agent, or Firm* — Sunstein Kann Murphy & Timbers LLP

(57) ABSTRACT

The present application relates to a method of preparing a genetic package displaying oligomers of modular antibody domains binding to a target and to a scaffold ligand as well as to vectors and libraries of genetic packages produced thereby. The invention further relates to methods of selecting suitable linker sequences for use in such oligomer display.

9 Claims, 2 Drawing Sheets

Related U.S. Application Data

Figure 1:
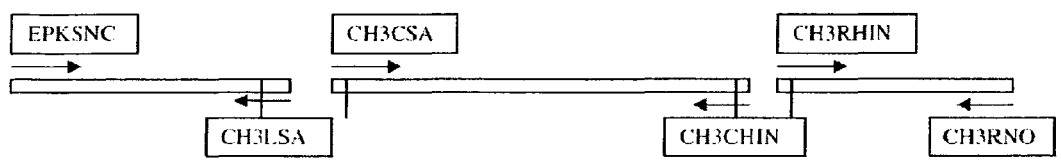

(60) Provisional application No. 60/946,287, filed on Jun. 26, 2007, provisional application No. 61/049,826, filed on May 2, 2008.

(51) Int. Cl.
*C07K 16/00* (2006.01)
*C07K 16/32* (2006.01)

(52) U.S. Cl.
CPC .... *C07K 2317/52* (2013.01); *C07K 2317/569* (2013.01); *C07K 2318/10* (2013.01); *C40B 30/04* (2013.01); *G01N 2333/70535* (2013.01)

(56) References Cited

U.S. PATENT DOCUMENTS

| | | | |
|---|---|---|---|
| 5,475,100 A | 12/1995 | Hashino et al. | 536/23.53 |
| 5,536,814 A | 7/1996 | Ruoslahti et al. | 530/329 |
| 5,723,323 A | 3/1998 | Kaurrman et al. | 435/172.3 |
| 5,759,817 A | 6/1998 | Barbas | 435/69.7 |
| 5,763,192 A | 6/1998 | Kauffman et al. | 435/7.1 |
| 5,814,476 A | 9/1998 | Kauffman et al. | 435/69.1 |
| 5,817,483 A | 10/1998 | Kauffman et al. | 435/69.1 |
| 5,824,514 A | 10/1998 | Kauffman et al. | 435/91.1 |
| 5,844,094 A | 12/1998 | Hudson et al. | 530/387.3 |
| 5,892,019 A | 4/1999 | Schlom et al. | 536/23.53 |
| 6,057,098 A | 5/2000 | Buechler et al. | 435/6 |
| 6,294,654 B1 | 9/2001 | Bogen et al. | 530/387.3 |
| 6,352,842 B1 | 3/2002 | Short et al. | 435/69.1 |
| 6,358,709 B1 | 3/2002 | Short et al. | 435/69.1 |
| 6,361,974 B1 | 3/2002 | Short et al. | 435/69.1 |
| 6,365,377 B1 | 4/2002 | Patten et al. | 435/91.1 |
| 6,376,246 B1 | 4/2002 | Crameri et al. | 435/440 |
| 6,562,617 B1 | 5/2003 | Anderson et al. | 435/325 |
| 6,602,684 B1 | 8/2003 | Umaña et al. | 435/69.1 |
| 7,442,778 B2 | 10/2008 | Gegg et al. | 530/391.7 |
| 7,632,497 B2 | 12/2009 | Stavenhagen | 424/133.1 |
| 7,645,861 B2 | 1/2010 | Gegg et al. | 530/391.7 |
| 7,655,764 B2 | 2/2010 | Gegg et al. | 530/391.7 |
| 7,655,765 B2 | 2/2010 | Gegg et al. | 530/391.7 |
| 7,662,931 B2 | 2/2010 | Gegg et al. | 530/391.7 |
| 7,750,127 B2 | 7/2010 | Gegg et al. | 530/391.7 |
| 7,750,128 B2 | 7/2010 | Gegg et al. | 530/391.7 |
| 7,858,090 B2 | 12/2010 | Koide | 424/145.1 |
| 8,008,453 B2 | 8/2011 | Gegg et al. | 530/391.7 |
| 8,580,927 B2 | 11/2013 | Dimitrov | 530/387.3 |
| 8,859,738 B2 | 10/2014 | Himmler et al. | |
| 8,921,279 B2 | 12/2014 | Himmler et al. | 506/9 |
| 9,045,528 B2 | 6/2015 | Rüker et al. | |
| 2002/0103345 A1 | 8/2002 | Zhu | 530/388.15 |
| 2002/0106370 A1 | 8/2002 | Cardy et al. | 424/133.1 |
| 2003/0027213 A1 | 2/2003 | Zhu et al. | 435/7.1 |
| 2003/0129188 A1 | 7/2003 | Barbas et al. | 424/144.1 |
| 2003/0148372 A1 | 8/2003 | Tomlinson et al. | 435/7.1 |
| 2003/0157091 A1 | 8/2003 | Hoogenboom | 424/130.1 |
| 2004/0018508 A1 | 1/2004 | Friedman | 435/6 |
| 2004/0043424 A1 | 3/2004 | Baughn et al. | 435/7.1 |
| 2004/0063924 A1 | 4/2004 | Tang et al. | 536/23.5 |
| 2004/0071690 A1 | 4/2004 | Hudon et al. | 424/130.1 |
| 2004/0082508 A1 | 4/2004 | Yue et al. | 514/12 |
| 2004/0097711 A1 | 5/2004 | Yue et al. | 530/387.1 |
| 2004/0101905 A1 | 5/2004 | Brekke et al. | 435/7.1 |
| 2004/0132101 A1 | 7/2004 | Lazar et al. | 435/7.1 |
| 2004/0146976 A1 | 7/2004 | Wittrup et al. | 435/69.1 |
| 2005/0009025 A1 | 1/2005 | Jakobsen et al. | 435/6 |
| 2005/0054832 A1 | 3/2005 | Lazar et al. | 530/387.3 |
| 2005/0069549 A1 | 3/2005 | Herman | 424/178.1 |
| 2005/0158829 A1 | 7/2005 | Fandl et al. | 435/69.1 |
| 2005/0244403 A1 | 11/2005 | Lazar et al. | 424/130.1 |
| 2005/0255548 A1 | 11/2005 | Lipovsck et al. | |
| 2005/0266000 A1 | 12/2005 | Bond et al. | 424/143.1 |
| 2006/0140934 A1 | 6/2006 | Gegg et al. | 424/133.1 |
| 2008/0227958 A1 | 9/2008 | Thompson et al. | 530/387.3 |
| 2009/0298195 A1 | 12/2009 | Rüker et al. | 436/501 |
| 2010/0048877 A1 | 2/2010 | Rüker et al. | 530/387.3 |
| 2011/0251375 A1 | 10/2011 | Rüker et al. | 530/387.3 |
| 2012/0010388 A1 | 1/2012 | Himmler | 530/387.3 |
| 2012/0028839 A1 | 2/2012 | Rüker et al. | 506/14 |
| 2012/0094874 A1 | 4/2012 | Rüker et al. | 506/18 |
| 2012/0276104 A1 | 11/2012 | Woisetschlager | 424/136.1 |
| 2015/0153359 A1 | 6/2015 | Himmler et al. | |

FOREIGN PATENT DOCUMENTS

| | | | |
|---|---|---|---|
| CN | 1606566 A | 4/2005 | C07K 5/08 |
| EP | 0 640 130 B1 | 7/1993 | C12N 15/12 |
| EP | 1 752 471 A1 | 2/2007 | C07K 16/00 |
| EP | 1 772 465 A1 | 4/2007 | C07K 16/00 |
| EP | 1 797 127 A2 | 6/2007 | A61K 47/48 |
| EP | 2 028 193 A1 | 2/2009 | C07K 16/00 |
| EP | 1 699 826 B1 | 3/2009 | C07K 16/00 |
| EP | 2 158 220 A1 | 3/2010 | C07K 16/00 |
| EP | 2 407 487 A1 | 1/2012 | C07K 16/32 |
| EP | 2 451 838 | 5/2012 | C12N 15/09 |
| JP | 2002-58479 A | 2/2002 | C12N 15/09 |
| JP | 2003-518377 | 6/2003 | C12N 15/09 |
| JP | 2003-518377 A | 6/2003 | C12N 15/09 |
| WO | WO 90/07861 | 7/1990 | C12P 21/00 |
| WO | WO 92/09690 | 6/1992 | C12N 15/00 |
| WO | WO 93/08278 | 4/1993 | C12N 15/10 |
| WO | WO 93/23537 | 11/1993 | C12N 15/12 |
| WO | WO 96/22377 | 7/1996 | C12N 15/62 |
| WO | WO 97/20858 | 6/1997 | C07K 16/32 |
| WO | WO 97/34631 | 9/1997 | A61K 39/395 |
| WO | WO 98/39482 | 9/1998 | C12Q 1/68 |
| WO | WO 00/42561 | 7/2000 | G06F 19/00 |
| WO | WO 00/71694 | 11/2000 | C12N 15/06 |
| WO | WO 01/01748 | 1/2001 | |
| WO | WO 01/48145 A2 | 7/2001 | |
| WO | WO 01/55366 A1 | 8/2001 | C12N 12/10 |
| WO | WO 01/57211 A1 | 8/2001 | C07K 14/725 |
| WO | WO 01/62908 A2 | 8/2001 | C12N 15/10 |
| WO | WO 01/70947 | 9/2001 | C12N 15/10 |
| WO | WO 01/83525 | 11/2001 | C07K 14/00 |
| WO | WO 01/88159 | 11/2001 | C12N 15/62 |
| WO | WO 02/06469 | 1/2002 | C12N 15/10 |
| WO | WO 02/32925 | 4/2002 | |
| WO | WO 02/44215 | 6/2002 | C07K 16/00 |
| WO | WO 02/059263 A2 | 8/2002 | |
| WO | WO 02/060919 | 8/2002 | |
| WO | WO 02/066636 A2 | 8/2002 | C12N 15/10 |
| WO | WO 02/088171 | 11/2002 | |
| WO | WO 03/012100 | 2/2003 | C12N 15/10 |
| WO | WO 03/029456 | 4/2003 | C12N 15/00 |
| WO | WO 03/075840 | 9/2003 | |
| WO | WO 2004/018674 | 3/2004 | C12N 15/10 |
| WO | WO 2004/033685 A1 | 4/2004 | C12N 15/12 |
| WO | WO 2004/041862 A2 | 5/2004 | C07K 16/00 |
| WO | WO 2004/044004 | 5/2004 | C07K 14/705 |
| WO | WO 2004/044011 | 5/2004 | |
| WO | WO 2004/050705 | 6/2004 | C07K 14/705 |
| WO | WO 2004/074322 | 9/2004 | C07K 14/725 |
| WO | WO 2005/021595 | 3/2005 | C07K 19/00 |
| WO | WO 2005/113595 A2 | 12/2005 | C07K 14/705 |
| WO | WO 2005/114215 | 12/2005 | G01N 33/68 |
| WO | WO 2005/116646 A1 | 12/2005 | G01N 33/50 |
| WO | WO 2006/033700 | 3/2006 | |
| WO | WO 2006/036834 | 4/2006 | C07K 19/00 |
| WO | WO 2006/037960 A2 | 4/2006 | C07K 14/705 |
| WO | WO 2006/054096 A2 | 5/2006 | C12N 15/62 |
| WO | WO 2006/056733 A1 | 6/2006 | C12N 15/12 |
| WO | WO 2006/072620 | 7/2006 | C07K 16/00 |
| WO | WO 2006/087637 | 8/2006 | C07K 16/32 |
| WO | WO 2008/003103 | 1/2008 | C07K 16/00 |
| WO | WO 2008/003116 | 1/2008 | C12N 15/09 |
| WO | WO 2008/119096 | 10/2008 | C07K 16/00 |
| WO | WO 2009/000006 | 12/2008 | C07K 16/00 |
| WO | WO 2009/099961 | 8/2009 | C07K 16/00 |
| WO | WO 2009/132876 A1 | 11/2009 | A61K 39/395 |

(56) References Cited

FOREIGN PATENT DOCUMENTS

| WO | WO 2011/003811 | 1/2011 | ............ C07K 16/00 |
|----|----------------|--------|------------------------|
| WO | WO 2012/007167 | 1/2012 | ............ C07K 16/32 |
| WO | WO 2015/049537 | 4/2015 | ............ C12Q 1/68 |

OTHER PUBLICATIONS

Short et al. (Dec. 1, 1995) Journal of Biological Chemistry vol. 270 pp. 28541 to 28550.*
Bird, et al., "Single-Chain Antigen-Binding Proteins," Science, vol. 242, No. 4877, p. 423, Oct. 21, 1988.
Brawley, et al, "Complementarity-Determining Region 1 Sequence Requirements Drive Limited Vα Usage in Response to Influenza Hemagglutinin in 307-319 Peptide[1,]" The Journal of Immunology, vol. 168, No. 8, pp. 3894-3901, Apr. 15, 2002.
Brekke, et al, "Therapeutic antibodies for human diseases at the dawn of the twenty-first century," nature Reviews Drug Discovery, vol. 2, No. 1, pp. 52-62, Jan. 2003.
Bunn, Jr., et al., "Expression of Her-2/ neu in Human Lung Cancer Cell Lines by Immunohistochemistry and Fluorescence in Situ Hybridization," Clinical Cancer Research, vol. 7, pp. 3239-3250, Oct. 2001.
Chlewicki, et al., "High-Affinity, Peptide-Specific T Cell Receptors Can be Generated by Mutations in CDR1, CDR2 or CDR3," Journal of Molecular Biology, vol. 346, No. 1, pp. 223-239, Feb. 11, 2005.
DiGiusto, et l., An Analysis of Sequence Variation in the β Chain Framework and Complementarity Determining Regions of an Allo-Reactive T Cell Receptor, Molecular Immunology, vol. 31, No. 9, pp. 693-699, Jan. 1994.
Dunn, et al, "Directed Evolution of Human T Cell Receptor CDR2 Residues by Phage Display Dramatically Enhances Affinity for Cognate Peptide-MHC Without Increasing Apparent Cross-Reactivity," Protein Science, vol. 15, pp. 710-721, Published by Cold Spring Harbor Laboratory Press, 2006.
Esteva, et al., "Molecular Predictors of Response to Trastuzumab and Lapatinib in Breast Cancer," Nature Reviews, Clinical Oncology, vol. 7, No. 2, Feb. 1, 2010, pp. 98-107.
Fountzilas, et al, "A randomized phase III study comparing three anthracycline-free taxane-based regimens, as first line chemotherapy, in metastatic breast cancer," Breast Cancer Research and Treatment, vol. 115, pp. 87-99, 2009.
Hoogenboom, H.R., "Selecting and screening recombinant antibody libraries," Nature in Biotechnology, vol. 23, No. 9, pp. 1105-1116, Sep. 2005.
Iyengar, et al., "A Pilot Study of Dose-Dense Paclitaxel With Trastuzumab and Lapatinib for Node-negative HER2-Overexpressed Breast Cancer," Clinical Breast Cancer, vol. 16, No. 2, pp. 87-94, Apr. 2016.
Krebber et al, "Selectively-infective Phage (SIP): A Mechanistic Dissection of a Novel in vivo Selection for Protein-ligand Interactions," Journal of Molecular Biology, vol. 268, No. 9, pp. 607-618, May 9, 1997.
Laugel, et al., "Design of Soluble Recombinant T Cell Receptors for Antigen Targeting and T Cell Inhibition," Theo Journal of Biological Chemistry, vol. 280, No. 3, pp. 1882-1892, Jan. 2005.
Leung, et al, "A HER2-specific Modified Fc Fragment (Fcab) Induces Antitumor Effects Through Degradation of HER2 and Apoptosis," Molecular Therapy, vol. 23, No. 11, pp. 1722-1733, Nov. 2015.
Liang, et al, "Cross-species Vascular Endothelial Growth Factor (VEGF)-blocking Antibodies Completely Inhibit the Growth of Human Tumor Xenografts and Measure the Contribution of Stromal VEGF," The Journal of Biological Chemistry, vol. 28, No. 2, pp. 951-961, Jan. 13, 2006.
Molloy, et al, "Soluble T Cell Receptors: Novel Immunotherapies," Current Opinion in Pharmacology, vol. 5, Issue 4, pp. 438-443, Aug. 2005.
Nakauchi, et al., "Molecular cloning of Lyt-2, a Membrane Glycoprotein Marking a Subset of Mouse T Lymphocytes: Molecular Homology to its Human Counterpart, Leu-2/T8, and to Immunoglobulin Variable Regions," Proceeding of the National Academy of Science of the United States of America, vol. 82, No. 15, pp. 5126-5130, Aug. 1, 1985.
Philippidis, "Companion Diagnostics: 52 Pick-Up," Genetic Engineering & Biotechnology News, Insight & Intelligence,12 pages, May 13, 2013.
Richman, et al., "Development of a Novel Strategy for Engineering High-Affinity Proteins by Yeast Display," Protein Engineering, Design & Selection, vol. 19, No. 6, pp. 255-264, 2006.
Richman, et al., "Structural features of T cell receptor variable regions that enhance domain stability and enable expression as single-chain VαVβ fragments," Molecular Immunology, vol. 46, Issue 5, pp. 902-916, Feb. 2009 (Abstract).
Stagg, et al., "Anti-ErbB-2 mAb therapy requires type I and II interferons and synergizes with anti-PD-1 or anti-CD137 mAb therapy," Proceedings of the National Academy of Sciences, USA, vol. 108, No. 17, pp. 7142-7147, Apr. 26, 2011.
Tolaney, et al., "Adjuvant Paclitaxel and Trastuzumab for Node-Negative, HER2-Positive Breast Cancer," The New England journal of Medicine, vol. 372, pp. 134-141, Jan. 8, 2015.
Traxlmayr et al., "Directed Evolution of Her2/neu-binding IgG1-Fc for Improved Stability and Resistance to Aggregation by Using Yeast Surface Display," Protein Engineering, Design & Selection, vol. 26, No. 4, pp. 255-265, 2013.
Willcox, et al., "Production of Soluble αβ T-cell Receptor Heterodimers Suitable for Biophysical Analysis of Ligand Binding", Protein Science, vol. 8, No. 11, pp. 2418-2423, Nov. 1999.
Wülfing, et al., "Correctly Folded T-cell Receptor Fragments in the Periplasm of *Escherichia coli*: Influence of Folding Catalysts," Journal of Molecular Biology, vol. 242, Issue 5, pp. 655-669, Oct. 6, 1994.
International Searching Authority, Written Opinion of International Searching Authority, Application No. PCT/GB2014/052994, 6 pages, Jan. 9, 2015.
European Patent Office, International Search Report, Application No. PCT/GB2014/052994, 5 pages, Jan. 9, 2015.
European Patent Office, International Search Report and Written Opinion, Application No. PCT/EP2016/057800, 18 pages, Jun. 24, 2016.
The International Bureau of WIPO, Switzerland, Authorized Officer Athina Nickitas-Etienne, International Preliminary Report on Patentability with Written Opinion of the International Searching Authority, International Application PCT/GB2014/052994, 7 pages, Apr. 5, 2016.
U.S. Appl. No. 11/722,517, filed Jun. 21, 2007.
U.S. Appl. No. 12/307,582, filed Jan. 5, 2009.
U.S. Appl. No. 12/307,578, filed Jun. 26, 2007.
U.S. Appl. No. 12/307,569, filed Sep. 21, 2009.
U.S. Appl. No. 13/086,897, filed Apr. 14, 2011.
U.S. Appl. No. 13/149,871, filed May 31, 2011.
U.S. Appl. No. 13/151,207, filed Jun. 1, 2011.
U.S. Appl. No. 13/228,559, filed Sep. 9, 2011.
U.S. Appl. No. 13/377,817, filed Dec. 12, 2011.
U.S. Appl. No. 13/434,765, filed Mar. 29, 2012.
U.S. Appl. No. 13/482,926, filed May 29, 2012.
U.S. Appl. No. 14/470,425, filed Aug. 27, 2014.
U.S. Appl. No. 14/559,662, filed Dec. 1, 2014.
U.S. Appl. No. 14/629,760, filed Feb. 24, 2015.
U.S. Appl. No. 14/853,919, filed Sep. 14, 2015.
U.S. Appl. No. 15/004,692, filed Jan. 22, 2016.
U.S. Appl. No. 15/087,272, filed Mar. 31, 2016.
Adachi et al., Interaction Between the Antigen and Antibody Is Controlled by the Constant Domains: Normal Mode Dynamics of the HEL-Hyhel-10 Complex,, Protein Science, vol. 12, No. 10, pp. 2125-2131, Oct. 2003.
Adib-Conquy et al., "Effect of Amino Acid Substitutions in the Heavy Chain CDR3 of an Autoantibody On Its Reactivity," International Immunology, vol. 10, No. 3, pp. 341-346, Mar. 1998.
Altschul et al., "Local Alignment Statistics," Methods in Enzymology vol. 266, pp. 460-480, 1996.

(56) References Cited

OTHER PUBLICATIONS

Amstutz et al., "In vitro Display Technologies: Novel Developments and Applications," Current Opinion Biotechnology, vol. 12, No. 4, pp. 400-405, Aug. 2001.

Asano et al., "Humanization of the Bispecific Epidermal Growth Factor Receptor×CD3 Diabody and Its Efficacy as a Potential Clinical Reagent," Clinical Cancer Research, vol. 12, No. 13, p. 4036-4042, Jul. 1, 2006.

Auf der Maur et al., "Antigen-Independent Selection of intracellular Stable Antibody Frameworks," Methods, vol. 34, No. 2, pp. 215-224, Oct. 2004.

Barbas III, et al., "Semisynthetic Combinatorial Antibody Libraries: A Chemical Solution to the Diversity Problem," Proceeding of the National Academy of Science. USA, vol. 89, No. 10, pp. 4457-4461, May 15, 1992.

Barclay, "Membrane Proteins With Immunoglobulin-Like Domains—A Master Superfamily of interaction Molecules," Seminars in Immunology, vol. 15, No. 4, pp. 215-223, Aug. 2003.

Batey et al., "Abstract B123: Preclinical Evaluation of FS102: A HER2-Specific Fcab With a Novel Mechanism of Action," Molecular Cancer Therapeutics, vol. 12, Supplement 11, B123, Nov. 2013.

Batey et al., Poster: "Pre-Clinical Evaluation of FS102: A HER2 Specific Fcab With a Novel Mechanism of Action," AACR-NCI-EORTC International Conference on Molecular Targets and Cancer Therapeutics, Boston, 1 page, Oct. 21, 2013.

Benhar et al., "Highly Efficient Selection of Phage Antibodies Mediated by Display of Antigen as Lpp-OmpA' Fusions on Live Bacteria," Journal of Molecular Biology, vol. 301, No. 4, pp. 893-904, Aug. 25, 2000.

Berntzen et al., "Prolonged and Increased Expression of Soluble Fc Receptors, IgG and a TCR-Ig Fusion Protein by Transiently Transfected Adherent 293E Cells," Journal Immunological Methods, vol. 298, No. 1-2, pp. 93-104, Mar. 2005.

Berntzen et al., "Characterization of an Fcγ/RI-Binding Peptide Selected by Phage Display," Protein Engineering, Design & Selection, vol. 19, No. 3, pp. 121-128, Jan. 19, 2006.

Berry et al., "Development of Functional Human Monoclonal Single-Chain Variable Fragment Antibody Against HIV-1 from Human Cervical B Cells." Hybrid. Hybridomaics, vol. 22, No. 2, pp. 97-108, Apr. 2003.

Binz et al., "High-Affinity Binders Selected From Designed Ankyrin Repeat Protein Libraries," Nature Biotechnology, vol. 22, No. 5, pp. 575-582, May 2004.

Binz et al., "Engineering Novel Binding Proteins From Nonimmunoglobulin Domains," Nature Biotechnology, vol. 23, pp. 1257-1268, Oct. 6, 2005.

Boder et al., "Yeast Surface Display for Screening Combinatorial Polypeptide Libraries," Nature Biotechnology, vol. 15, No. 6, pp. 553-557, Jun. 1997.

Boder et al., "Yeast Surface Display for Directed Evolution of Protein Expression, Affinity, and Stability," Methods in Enzymology, vol. 328, pp. 430-444, 2000.

Boder et al., "Directed Evolution of Antibody Fragments With Monovalent Femtomolar Antigen-Binding Affinity," Proceedings of the National Academy of Science; vol. 97, No. 20, pp. 10701-10705, Sep. 26, 2000.

Bork et al., "The Immunoglobulin Fold. Structural Classification, Sequence Patterns and Common Core", Journal of Molecular Biology, vol. 242, pp. 309-320, 1994.

Boulter et al., "Stable, Soluble, High-Affinity, Engineered T Cell Receptors: Novel Antibody-Like Proteins for Specific Targeting of Peptide Antigens," Clinical and Experimental Immunology, pp. 454-460, 2005.

Bowie et al., "Deciphering the Message in Protein Sequences: Tolerance to Amino Acid Substitutions" Science, vol. 247, No. 4948, pp. 1306-1310, Mar. 16, 1990.

Burgess et al., "Possible Dissociation of the Heparin-binding and Mitogenic Activities of Heparin-binding (Acidic Fibroblast) Growth Factor-1 from Its Receptor-binding Activities by Site Directed Mutagenesis of a Single Lysine Residue," Journal of Cell Biology, vol. 111, pp. 2129-2138, Nov. 1990.

Cabilly et al., "Generation of Antibody Activity From Immunoglobulin Polypeptide Chains Produced in *Escherichia coli*," Proceedings of National Academy of Science USA, vol. 81, pp. 3273-3277, Jun. 1984.

Caldas et al., "Humanization of the Anti-CD18 Antibody 6.7: An Unexpected Effect of a Framework Residue in Binding to Antigen," Molecular Immunology, vol. 39, No. 15, pp. 941-952, May 2003.

Carter, "Bispecific Human IgG by Design," Journal of Immunological Methods, vol. 248, pp. 7-15, 2001.

Carter et al., "High Level *Escherichia coli* Expression and Production of a Bivalent Humanized Antibody Fragment," Biotechnology, vol. 10, No. 2, pp. 163-167, Feb. 1992.

Chen et al., "Isolation of High-Affinity Ligand-Binding Proteins by Periplasmic Expression With Cytometric Screen (PECS)," Nature Biotechnology vol. 19, pp. 537-542, Jun. 2001.

Chien et al., "Significant Structural and Functional Change of an Antigen-Binding Site by a Distant Amino Acid Substitution: Proposal of a Structural Mechanism," Proceeding of the National Academy of Science USA, vol. 86, No. 14, pp. 5532-5536, Jul. 1989.

Chirino et al., "Minimizing the Immunogenicity of Protein Therapeutics," Drug Discovery Today, vol. 9, No. 2, pp. 82-90, Jan. 2004.

Cho et al., "Structure of the Extracellular Region of HER2 Alone and in Complex with the Herceptin Fab," Nature, vol. 421, pp. 756-760, Feb. 13, 2003.

Coco et al., "DNA Shuffling Method for Generating Highly Recombined Genes and Evolved Enzymes", Nature Publishing Group, vol. 19, pp. 354-359, Apr. 2001.

Conrath et al., "Antigen Binding and Solubility Effects upon the Veneering of a Camel VHH in Framework-2 to Mimic a VH", Journal of Molecular Biology, vol. 350, pp. 112-125, 2005.

Cornish-Bowden, "Nomenclature for Incompletely Specified Bases in Nucleic Acid Sequences: Recommendations 1984," Nucleic Acids Research, vol. 3, No. 9, pp. 3021-3030, May 10, 1985.

Cortez-Retamozo et al., "Efficient Tumor Targeting by Single-Domain Antibody Fragments of Camels", International Journal of Cancer, vol. 98, pp. 456-462, 2002.

Crameri et al., "DNA Shuffling of a Family of Genes From Diverse Species Accelerates Directed Evolution ," Nature vol. 391, pp. 288-291, Jan. 15, 1998.

Dall' Acqua et al., "Increasing the Affinity of a Human IgG1 for the Neonatal Fc Receptor: Biological Consequences," The Journal of Immunology, vol. 169, pp. 5171-5180, 2002.

Dall' Acqua et al., "Modulation of the Effector Functions of a Human IgG1 through Engineering of Its Hinge Region," The Journal of Immunology, vol. 177, pp. 1129-1138, 2006.

de Jager et al., "Simultaneous Detection of 15 Human Cytokines in a Single Sample of Stimulated Peripheral Blood Mononuclear Cells," Clinical Diagnostic Laboratory Immunology, vol. 10, No. 1, pp. 133-139, 2003.

Doi et al., "Screening of Conformationally Constrained Random Polypeptide Libraries Displayed on a Protein Scaffold," Cellular and Molecular Life Sciences, vol. 54, No. 5, pp. 394-404, May 1998.

Dottorini et al., "Crystal Structure of a Human VH: Requirements for Maintaining a Monomeric Fragment," Biochemistry, vol. 43, No. 3, pp. 622-628, Jan. 27, 2004.

Ewert et al., "Stability Improvement of Antibodies for Extracellular and Intracellular Applications: CDR Grafting to Stable Frameworks and Structure-Based Framework Engineering ," Methods, vol. 34, pp. 184-199, 2004.

F-star, "F-star Alpha: A New Asset Centric Company," 15 pages, Feb. 11, 2014.

Felgenhauer et al., "Nucleotide Sequences of the Cdnas Encoding the V-Regions of H- and L-Chains of a Human Monoclonal Antibody Specific to HIV-1-gp41," Nucleic Acids Research, vol. 18, No. 16, pp. 4927, 1990.

Fellouse et al., "Synthetic Antibodies From a Four-Amino-Acid Code: A Dominant Role for Tyrosine in Antigen Recognition," Proceeding of the National Academy of Science, vol. 101, No. 34, pp. 12467-12472, Aug. 24, 2004.

(56) References Cited

OTHER PUBLICATIONS

Fellouse et al., "Molecular Recognition by a Binary Code," The Journal of Molecular Biology, vol. 348, No. 5, pp. 1153-1162, May 20, 2005.

Fellouse et al., "Tyrosine Plays a Dominant Functional Role in the Paratope of a Synthetic Antibody Derived from a Four Amino Acid Code," The Journal of Molecular Biology, vol. 357, pp. 100-114, 2006.

Fields et al., "A Novel Genetic System to Detect Protein-Protein Interactions," Nature vol. 340, pp. 245-246, Jul. 20, 1989.

Fitzgerald, "In vitro Display Technologies—New Tools for Drug Discovery," vol. 5, No. 6, pp. 253-258, Jun. 2000.

Foote, "Antibody Framework Residues Affecting the Conformation of the Hypervariable Loops," Journal of Molecular Biology, vol. , No. 2, pp. 487-499, Mar. 20, 1992.

Gao et al., "Making Artificial Antibodies: A Format for Phage Display of Combinatorial Heterodimeric Arrays," Proceedings of the National Academy of Sciences of USA, vol. 96, No. 11 pp. 6025-6030, May 25, 1999.

Georgiou et al., "Practical Applications of Engineering Ggram-Negative Bacterial Cell Surfaces," Trends in Biotechnology, vol. 11, No. 1, pp. 6-10, Jan. 1993.

Georgiou et al., "Display of Heterologous Proteins on the Surface of Microorganisms: From the Screening of Combinatorial Libraries to Live Recombinant Vaccines," Nature Biotechnology vol. 15, No. 1, pp. 29-34, Jan. 1997.

Ghahroudi et al., "Selection and Identification of Single Domain Antibody Fragments from Camel Heavy-Chain Antibodies," FEBS Letters, vol. 414, No. 3, pp. 521-526, Sep. 15, 1997.

Giusti et al., "Somatic Diversification of S107 from an Antiphosphocholine to an Anti-DNA Autoantibody is Due to a Single Base Change in its Heavy Chain Variable Region," Proceedings of the National Academy of Science, USA, vol. 84, No. 9, pp. 2926-2930, May 1987.

Goncalves, "Fluorescent Labeling of Biomolecules with Organic Probes," Chemical Review, vol. 109, No. 1, pp. 190-212, 2009.

Gram et al., "In vitro Selection and Affinity Maturation of Antibodies from a Naive Combinatorial Immunoglobulin Library," Proceedings of the National Academy of Sciences of the United States of America, vol. 89, No. 8, pp. 3576-3580, Apr. 15, 1992.

Halaby et al., "The Immunoglobulin Fold Family: Sequence Analysis and 3D Structure Comparisons," Protein Engineering, vol. 12, No. 7, pp. 563-571, Jul. 1999.

Hanes et al., "In vitro Selection and Evolution of Functional Proteins by Using Ribosome Display," Proceedings of the National Academy of Science, USA, vol. 94, No. 19, pp. 4937-4942, May 1997.

Harriman et al., "Multiplexed Elispot Assay," Journal Immunology Methods, vol. 341, No. 1-2, pp. 127-134, Feb. 28, 2009.

Hasenhindl et al., "Stability Assessment on a Library Scale: A Rapid Method for the Evaluation of the Commutability and Insertion of Residues in C-Terminal Loops of the CH3 domains of IgG1-Fc," Protein Engineering, Design and Selection, vol. 26, issue 10, pp. 675-682, Oct. 2013.

Hasenhindl et al., "Creating Stable Stem Regions for Loop Elongation in Fcabs—Insights from Combining Yeast Surface Display, in Sihco Loop Reconstruction and Molecular Dynamics Simulations", Biochimica et Biophysica Acta, vol. 1844, No. 9, pp. 1530-1540, Sep. 2014.

Haurum, "How to Leverage Oncogene Addiction: Targetd Biological Therapy Inducing Growth Factor Receptor Internalization and Degradation," PEPtalk: The Protein Science Week Jan. 19, 2015.

Hayhurst et al., "High-throughput Antibody Isolation," Current Opinion in Chemical Biology, vol. 5, No. 6, pp. 683-689, Dec. 2001.

He et al., "Structure of a Human Monoclonal Antibody Fab Fragment Against gp41 of Human Immunodeficiency Virus Type 1," Proceedings of the National Academy of Science, USA vol. 89, No. 15, pp. 7154-7158, Aug. 1, 1992.

Hermeling et al., "Structure-Immunogenicity Relationships of Therapeutic Proteins," Pharmaceutical Research, vol. 21, No. 6, pp. 897-903, Jun. 2004.

Holler et al., "In vitro Evolution of a T Cell Receptor with High Affinity for Peptide/MHC," Proceedings of the National Academy of Science, USA, vol. 97, No. 10, pp. 5387-5392, May 9, 2000.

Holliger et al., "Engineered Antibody Fragments and the Rise of Single Domains," Nature Biotechnology, vol. 23, No. 9, pp. 1126-1136, Sep. 2005.

Hoogenboom et al., "Multi-Subunit Proteins on the Surface of Filamentous Phage: Methodologies for Displaying Antibody (Fab) Heavy and Light Chains," Nucleic Acids Research, vol. 19, No. 15, pp. 4133-4137, Aug. 11, 1991.

Hoover et al., "DNAWorks: An Automated Method for Designing Oligonucleotides for PCR-based Gene Synthesis," Nucleic Acids Research, vol. 30, No. 10, May 15, 2002.

Hosse et al., "A New Generation of Protein Display Scaffolds for Molecular Recognition," Protein Science, vol. 15, No. 1, pp. 14-27, Jan. 2006.

Hufton et al., "Development and Application of Cytotoxic T Lymphocyte-Associated Antigen 4 As a Protein Scaffold for the Generation of Novel Binding Ligand," FEBS Letters, vol. 465, No. 3, pp. 225-231, Jun. 23, 2000.

Huston et al., "Protein Engineering of Antibody Binding Sites: Recovery of Specific Activity in an Anti-Digoxin Single-Chain Fv Analogue Produced in *Escherichia coli*," Proceedings of the National Academy of Science, USA, vol. 85, No. 16, pp. 5879-5883, Aug. 1988.

Isaac et al., Poster: "Pre-Clinical Evaluation of FS102: A HER2-Specific Fcab with a Novel Mechanism of Action," AstraZeneca-MedImmune—Cambridge Cancer Centre Symposium, 1 page, Mar. 25, 2014.

Janeway et al., "Immunobiology, the Immune System in Health and Disease," 6th Edition, Garland Science, 2005.

Jez et al., "Significant Impact of Single N-Glycan Residues on the Biological Activity of Fc-Based Antibody-Like Fragments," The Journal of Biological Chemistry, vol. 287, No. 9, pp. 24313-24319, Jul. 13, 2012.

Johnsson et al., "Split Ubiquitin As a Sensor of Protein interactions in vivo," Proceedings of the National Academy of Science, USA vol. 91, No. 22, pp. 10340-10344, Oct. 1994.

Jones et al., "Replacing the Complementarity-Determining Regions in a Human Antibody With Those From a Mouse," Nature, vol. 321, No. 6069, pp. 522-525, May 29, 1986.

Jung et al., "Surface Display of Zymomonas Mobilis Levansucrase by Using the Ice-Nucleation Protein of Pseudomonas Syringae," Nature Biotechnology vol. 16, No. 6, 576-580, Jun. 1998.

Kainer et al., "Correlation Between CD16a Binding and Immuno Effector Functionality of an Antigen Specific Immunoglobulin Fc Fragment (Fcab)," Archives of Biochemistry and Biophysics, vol. 526, No. 2, pp. 154-158, Oct. 23, 2012.

Kang et al., "Linkage of Recognition and Replication Functions by Assembling Combinatorial Antibody Fab Libraries Along Phage Surfaces," Proceedings of the National Academy of Science, USA, vol. 88, No. 10, pp. 4363-4366, May 15, 1991.

Kang et al., "Human Neutralizing Fab Molecules against Severe Acute Respiratory Syndrome Coronavirus Generated by Phage Display," Clinical and Vaccine Immunology, vol. 13, No. 8, pp. 953-957, Aug. 2006.

Kashmiri et al., "SDR Grafting—A New Approach to Antibody Humanization," Methods, vol. 36, No. 1, pp. 25-34, May 2005.

Kay et al., "Phage Display of Peptides and Proteins: A Laboratory Manual," Academic Press, 1996.

Kettleborough et al., "Humanization of a Mouse Monoclonal Antibody by CDR-Grafting: the importance of Framework Residues on Loop Conformation," Protein Engineering, vol. 4, No. 7, pp. 773-783, Oct. 1991.

Kieke et al., "Selection of Functional T Cell Receptor Mutants From a Yeast Surface-Display Library," Proceedings of the National Academy of Science, USA, vol. 96, No. 10, pp. 5651-5656, May 1999.

(56) References Cited

OTHER PUBLICATIONS

Kikuchi et al., "Novel Family Shuffling Methods for the in vitro Evolution of Enzymes," Gene, vol. 236, No. 1, pp. 159-167, Aug. 5, 1999.
Kikuchi et al., "An Effective Family Shuffling Method Using Single-Stranded DNA," Gene, vol. 243, No. 1-2, pp. 133-137, Feb. 8, 2000.
Kohl et al., "Cloning and Expression of an HIV-1 Specific Single-Chain Fv Region Fused to *Escherichia coli* Alkaline Phosphatase," Annals of the New York Academy of Science, vol. 646, pp. 106-114, Dec. 27, 1991.
Koide et al., "High-Affinity Single-Domain Binding Proteins with a Binary-Code Interface," Proceedings of the National Academy of Science, USA, vol. 104, No. 16, pp. 6632-6637, Apr. 17, 2007.
Koivunen et al., "Selection of Peptides Binding to the α5β1 Integrin from Phage Display Library", The Journal of Biological Chemistry, vol. 268, No. 27, pp. 20205-20210, Sep. 25, 1993.
Kolkman et al., "Directed Evolution of Proteins by Exon Shuffling, Nature Biotechnology," vol. 19, pp. 423-428, May 2001.
Konig, "Interactions Between MHC Molecules and Co-Receptors of the TCR," Current Opinion in Immunology, pp. 75-83, Mar. 2002.
Kontermann, "Dual Targeting Strategies With Bispecific Antibodies," MAbs, vol. 4, No. 2, pp. 182-197, Mar. 2012.
Koren et al., "Immune Responses to Therapeutic Proteins in Humans—Clinical Significance, Assessment and Prediction," Current Pharmaceutical Biotechnology, vol. 3, pp. 349-360, 2002.
Kufer et al., "A Revival of Bispecific Antibodies," Trends in Biotechnology, vol. 22, No. 5, pp. 238-244, May 2004.
Kunkel et al., "Rapid and Efficient Site-Specific Mutagenesis Without Phenotype Selection," Proceedings of National Academy of Sciences, vol. 82, pp. 488-492, Jan. 1985.
Laffly et al., "Monoclonal and Recombinant Antibodies, 30 years after . . . ," Human Antibotics, vol. 14, pp. 33-55, 2005.
Lauvrat et al., "Identification and Characterisation of C1q-Binding Phage Displayed Peptides," Biology Chemistry, vol. 378, No. 12, pp. 1509-1519, Dec. 1997.
Lazar et al., "Transforming Growth Factor α: Mutation of Aspartic Acid 47 and Leucine 48 Results in Different Biological Activities," Molecular and Cellular Biology, pp. 1247-1252, Mar. 1988.
Le Gall et al., "Effect of Linker Sequences Between the Antibody Variable Domains on the Formation, Stability and Biological Activity of a Bispecific Tandem Diabody," Protein Engineering, Design & Selection, vol. 17, No. 44, pp. 357-366, 2004.
Lea et al., "Analysis of Antigenic Surfaces of Proteins," Federation of American Societies for Expermential Biology, vol. 9, No. 1, pp. 87-93, Jan. 1995.
Lederman et al., "A Sinlge Amino Acid Substitution in a Common African Allele of the CD4 Molecule Ablates Binding of the Monoclonal Antibody, OKT4," Molecular Immunology vol. 28, No. 11, pp. 1171-1181, Nov. 1991.
Lee et al., "Surface-Displayed Viral Antigens on *Salmonella* Carrier Vaccine," Nature Biotechnology, vol. 18, No. 6, pp. 645-648, Jun. 2000.
Lefranc et al., "IMGT, the International ImMunoGeneTics Database," Nucleic Acids Research, vol. 27, No. 1, pp. 209-212, Jan. 1, 1999.
Lefranc, "IMGT, the International ImMunoGeneTics database," Nucleic Acids Research, vol. 29, No. 1, pp. 207-209, 2001.
Lefranc, "IMGT, the International ImMunoGeneTics database," Nucleic Acids Research, vol. 31, No. 1, pp. 307-310, 2003.
Lefranc et al., "IMGT Unique Numbering for Immunoglobulin and T Cell Receptor Constant Domains and Ig Superfamily C-like Domains," Developmental and Comparative Immunology vol. 27, pp. 55-77, 2003.
Lefranc et al., "IMGT Unique Numbering for immunoglobulin and T Cell Receptor Constant Domains and Ig Superfamily C-like Domains," Developmental and Comparative Immunology, vol. 29, pp. 185-203, 2005.
Lefranc et al., "IMGT, the International 1mMunoGeneTics Information System," Nucleic Acids Research, vol. 33, Database issue, pp. D593-D597, 2005.
Li et al., "Beta-Endorphin Omission Analogs: Dissociation of Immunoreactivity From Other Biological Activities," Proceedings of the National Academy of Science, USA, vol. 77, No. 6, pp. 3211-3214, Jun. 1980.
Li et al., "Directed Evolution of Human T-Cell Receptors With Picomolar Affinities by Phage Display," Nature Biotechnology, vol. 23, No. 3, pp. 349-354, Mar. 2005.
Lo Conte et al., "The Atomic Structure of Protein-Protein Recognition Sites," Journal of Molecular Biology, vol. 285, pp. 2177-2198, 1999.
Lowman et al., "Selecting High-Affinity Binding Proteins by Monovalent Phage Display," Biochemistry, vol. 30, pp. 10832-10838, 1991.
Lutz et al., "Creating Multiple Crossover DNA Libraries Independent of Sequence Identity," Proceedings of the National Academy of Science, USA, vol. 98, No. 20, pp. 11248-11253, Sep. 25, 2001.
Malborg et al., "Selective Phage Infection Mediated by Epitope Expression on F Pilus," Journal of Molecular Biology, vol. 273, pp. 544-551, 1997.
Marvin et al., "Recombinant Approaches to IgG-like Bispecific Antibodies," Acta Pharmacologica Sinica, vol. 6, pp. 649-658, Jun. 2005.
Masuda et al., "The Role of Interface Framework Residues in Determining Antibody VH/VL, Interaction Strength and Antigen-Binding Affinity," The FEBS Journal, vol. 273, pp. 2184-2194, 2006.
Mattheakis et al., "An in vitro Polysome Display System for Identifying Ligands From Very Large Peptide Libraries," Proceedings of the National Academy of Science, USA, vol. 91, pp. 9022-9026, Sep. 1994.
Maynard et al., "Antibody Engineering;" Annual Review of Biomedical Engineering, vol. 2, pp. 339-376, 2000.
McCall et al., "Isolation and Characterization of an Anti-CD16 Single-chain Fv Fragment and Construction of an Anti-HER2/neu/anti-CD16 Bispecific scFv that Triggers CD16-dependent Tumor Cytolysis," Molecular Immunology, vol. 36, pp. 433-446, 1999.
McCall et al., "Increasing the Affinity for Tumor Antigen Enhances Bispecific Antibody Cytotoxicity," The Journal of immunology, vol. 166, pp. 6112-6117, 2001.
Merz et al., "The Protein Folding Problem and Tertiary Structure Prediction," Chapter 1, Authors Adrian Roitberg and Ron Elber, "Modeling Side Chains in Peptides and Proteins with Locally Enhanced Sampling/Simulated Annealing Method", Birkhauser, 584 pages, 1994.
Merz et al., "The Protein Folding Problem and Tertiary Structure Prediction," Chapter 14, Authors J. Thomas Ngo, Joe Marks and Martin Karplus, "Computational Complexity. Protein Structure Prediction, and the Levinthal Paradox", Birkhauser, 9 pages, 1994.
Miyazaki et al., "Changes in the Specificity of Antibodies by Site-Specific Mutagenesis Followed by Random Mutagenesis," Protein Engineering, vol. 12, No. 5, pp. 407-415, 1999.
Moza et al., "Long-Range Cooperative Binding Effects in a T Cell Receptor Variable Domain," Proceedings of the National Academy of Science, USA, vol. 103, No. 26, pp. 9867-9872, Jun. 27, 2006.
Munoz-Olaya, "Advancing Novel Modular Antibody Technology for Generating Bispecific Antibodies," PEGS Lisbon, Nov. 3-4, 2014.
Nemoto et al., "In vitro virus: Bonding of mRNA Bearing Puromycin at the 3'-Terminal End to the C-terminal End of its Encoded Protein on the Robosome in vitro," FEBS Letters, vol. 414, pp. 405-408, 1997.
Nygren et al., "Scaffold for Engineering Novel Binding Sites in Proteins," Current Biology, Engineering and Design, vol. 7, pp. 463-469, 1997.
Park et al., "Rationally Designed Anti-HER2/neu Peptide Mimetic Disables P185 HER2/neu Tyrosine Kinases in vitro and in vivo," Nature Biotechnology, vol. 18, pp. 194-198, Feb. 2000.
Paul, Fundamental Immunology, Chapter 9, "Structure and Function of Imunoglobulins", Third Edition, Raven Press, pp. 292-295, 1993.

(56) References Cited

OTHER PUBLICATIONS

Pelletier et al., "Oligomerization Domain-Directed Reassembly of Active Dihydrofolate Reductase From Rationally Designed Fragments," Proceedings of the National Academy of Science, USA, vol. 95, pp. 12141-12146, Oct. 1998.
Perosa et al., "CD20 Mimicry by a MAb Rituximab-Specific Linear Peptide, A Potential Tool for Active Immunotherapy of Autoimmune Diseases," Annals New York Academy of Sciences, pp. 672-683, 2005.
Presta et al., "Engineering Therapeutic Antibodies for Improved Function," Biochemical Society, vol. 30, No. 4, pp. 487-490, Mar. 2002.
Privezentzev, Poster: "F-star: Advancing Novel Bispecific Antibody Biologics," Gordon Research Conference; Antibody Biology & Engineering, 1 page, Mar. 2014.
Riechmann et al., "Single Domain Antibodies: Comparison of Camel VH and Camelised Human VH Domains," Journal of Immunological Methods, vol. 231, pp. 25-38, 1999.
Roberts et al., "RNA-Peptide Fusions for the in vitro Selection of Peptides and Proteins," Proceedings of the National Academy of Sciences, USA, vol. 94, pp. 12297-12302, Nov. 1997.
Rondot et al., "A Helper Phage to Improve Single-Chain Antibody Presentation in Phage Display," Nature Biotechnology, vol. 19, pp. 75-78, Jan. 2001.
Roovers et al., "Efficient Inhibition of EGFR Signalling and of Tumour Growth by Antagonistic Anti-EGFR Nanobodies," Cancer Immunology Immunotherapy, vol. 56, pp. 303-317, 2007.
Rudikoff et al., "Single Amino Acid Substitution Altering Antigen-Binding Specificity," Proceedings of the National Academy of Sciences, vol. 79, pp. 1979-1983, Mar. 1982.
Ruiz et al., "IMGT, the International ImMunoGeneTics database," Nucleic Acids Research, vol. 28, No. 1, pp. 219-221, 2000.
Rüker et al., "Expression of a Human Monoclonal Anti-HIV-1 Antibody in CHO Cells" Annals of New York Academy of Sciences, vol. 646, pp. 212-219, Dec. 27, 1991.
Saerens et al., "Identification of a Universal VHH Framework to Graft Non-canonical Antigen-binding Loops of Camel Single-domain Antibodies," Journal of Molecular Biology, vol. 352, pp. 597-607, 2005.
Salfield, "Isotype Selection in Antibody Engineering," Nature Biotechnology, vol. 25, No. 12, pp. 1369-1372, 2007.
Schaffitzel et al., "Ribosome Display: an in vitro Method for Selection and Evolution of Antibodies From Libraries," Journal of Immunological Methods, vol. 231, pp. 119-135, 1999.
Schmittel et al., "Application of the IFN-γ ELISPOT Assay to Quantify T Cell Responses Against Proteins", Journal of Immunological Methods, vol. 247, pp. 17-24, 2001.
Shao et al., "Random-priming in vitro Recombination: An Effective Tool for Directed Evolution," Nucleic Acids Research, vol. 26, No. 2, pp. 681-683, 1998.
Shields et al., "High Resolution Mapping of the Binding Site on Human IgG1 for FcγRI, FcγRII, FcγRIII, and FcRn and Design of IgG1 Variants with Improved Binding to the FFcγR," The Journal of Biological Chemistry, vol. 276, No. 9, pp. 6591-6604, 2001.
Shusta et al., "Directed Evolution of a Stable Scaffold for T-cell Receptor Engineering," Nature Biotechnology, vol. 19, 6 pages, Jul. 2000.
Sidhu et al., "Synthetic Therapeutic Antibodies," Nature Chemical Biology, vol. 2, No. 12, pp. 682-688, Dec. 2006.
Simon et al., "A Functional Antibody Mutant With an Insertion in the Framework Region 3 Loop of the VH Domain: Implications for Antibody Engineering," Protein Engineering, vol. 5, No. 3, pp. 229-234, 1992.
Skolnick et al., "From Genes to Protein Structure and Function: Novel Applications of Computational Approaches in the Genomic Era," Trends in Biotechnology, vol. 18, pp. 34-39, Jan. 2000.
Smith, "Filamentous Fusion Phage: Novel Expression Vectors That Display Cloned Antigens on the Virion Surface," Science, vol. 228, No. 4705, pp. 1315-1317, Jun. 14, 1985.
Spiridon et al., "Targeting Multiple Her-2 Epitopes with Monoclonal Antibodies Results in Improved Antigrowth Activity of a Human Breast Cancer Cell Line in Vvitro and in Vivo,": Clinical Cancer Research, vol. 8, pp. 1720-1730, Jun. 2002.
Tangri et al., "Rationally Engineered Therapeutic Proteins with Reduced Immunogenicity," The Journal of Immunology, pp. 3187-3196, 2005.
Traxlmayr et al., "Construction of pH-Sensitive Her2-binding IgG1-Fc by Directed Evolution," Biotechnology, vol. 9, pp. 1013-1022, 2014.
Uhlenbroich, "F-star: Advancing Novel Bispecific Antibody Biologics," Empowered Antibodies Congress, 1 page, Jun. 18-19, 2014—Abstract.
Vajdos et al., "Comprehensive Functional Maps of the Antigen-binding Site of an Anti-ErbB2 Antibody Obtained with Shotgun Scanning Mutagenesis," Journal of Molecular Biology, vol. 320 pp. 416-428, 2002.
Virnekas et al., "Trinucleotide Phosphoramidites: Ideal Reagents for the Synthesis of Mixed Oligonucleotides for Random Mutagenesis," Nucleic Acids Research, vol. 22, No. 25, pp. 5600-5607, 1994.
Visintin et al., Selection of Antibodies for Intracellular Function Using a Two-hybrid in vivo System, Proceedings of the National Academy of Science, USA, vol. 96, No. 21, pp. 11723-11728, Oct. 12, 1999.
Vogt et al., "Construction of an Artificial Receptor Protein ("Anticalin") Based on the Human Apolipoprotein D," ChemBioCem, vol. 5, No. 2, pp. 191-199, Feb. 6, 2004.
Wang et al., "Expression Patterns and Transcript Processing of ftt-1 and ftt-2, two C. elegans 14-3-3 Homologues," Journal of Molecular Biology, vol. 268, pp. 619-630, 1997.
Wang et al., "Retargeting T Cells for HER2-Positive Tumor Killing by a Bispecific Fv-Fc Antibody," PLOS One, vol. 8, No. 9, pp. e75589-1-e75589-11, Sep. 23, 2013.
Weaver-Feldhaus et al., "Yeast Mating for Combinatorial Fab Library Generation and Surface Display," FEBS Letters, vol. 564, No. 1-2, pp. 24-34, Apr. 23, 2004.
Weber et al., "Class II-Restricted T Cell Receptor Engineered In Vitro for Higher Affinity Retains Peptide Specificity and Function," Proceedings of the National Academy of Sciences, vol. 102, No. 52, pp. 19033-19038, Dec. 27, 2005.
Weiner et al., "Site-Directed Mutagenesis of Double-Stranded DNA by the Polymerase Chain Reaction," Gene, vol. 151, No. 1-2, pp. 119-124, Dec. 30, 1994.
Whitehorn et al., "A Generic Method for Expression and Use of "Tagged" Soluble Versions of Cell Surface Receptors," BioTechnology, vol. 13, No. 11, pp. 1215-1219, Nov. 1995.
Winkler et al., "Changing the Antigen Binding Specificity by Single Point Mutations of an Anti-p24 (HIV-1) Antibody," The Journal of Immunology, vol. 165, No. 8, pp. 4505-4514, Oct. 15, 2000.
Winter et al., "Humanized Antibodies," Immunology Today, vol. 14, No. 6, pp. 243-246, 1993.
Wittrup, "Protein Engineering by Cell-Surface Display," Current Opinion in Biotechnology, vol. 12, No. 4, pp. 395-399, Aug. 2001.
Woisetschlager et al., "In vivo and in vitro Activity of an Immunoglobulin Fc Fragment (Fcab) with Engineered Her-2/neu Binding Sites," Biotechnology Journal, vol. 9, No. 6, pp. 844-851, Jun. 2014.
Wozniak-Knopp et al., "Introducing Antigen-Binding Sites in Structural Loops of Immunoglobulin Constant Domains: Fc Fragments with Engineered HER2/neu-binding Sites and Antibody Properties," Protein Engineering, Design & Selection, vol. 23, No. 4, pp. 289-297, Apr. 2010.
Wu et al., "Humanization of a Murine Monoclonal Antibody by Simultaneous Optimization of Framework and CDR Residues," Journal of Molecular Biology, vol. 294, No. 1, pp. 151-162, Nov. 19, 1999.
Xiao et al., "A Large Library Based on a Novel (CH2) Scaffold: identification of HIV-1 Inhibitors," Biochemical and Biophysical Research Communications, vol. 387, No. 2, pp. 387-392, Sep. 18, 2009.
Yanez et al., "Combinatorial Condon-Based Aminio Acid Substitutions," Nucleic Acids Research, vol. 32, No. 20, pp. 1-10, 2004.

(56) References Cited

OTHER PUBLICATIONS

Yau et al., "Affinity Maturation of a VhH by Mutational Hotspot Randomization," Journal of Immunological Methods, vol. 297, No. 1-2, pp. 213-224, Feb. 2005.

Zemlin et al., "Expressed Murine and Human CDR-H3 Intervals of Equal Length Exhibit Distinct Repertoires that Differ in their Amino Acid Composition and Predicted Range of Structures," Journal of Molecular Biology, vol. 334, No. 4, pp. 733-749, Dec. 5, 2003.

Zhao et al., "A Novel Strategy by the Action of Ricin that Connects Phenotype and Genotype without Loss of the Diversity of Libraries," Journal of American Chemical Society vol. 124, No. 4, pp. 538-543, Jan. 30, 2002.

Zhou et al., "A Novel Strategy by the Action of Ricin that Connects Phenotype and Genotype without Loss of the Diversity of Libraries," Journal of American Chemical Society vol. 124, No. 4, pp. 538-543, Jan. 30, 2002.

European Patent Office—Munich, Extended European Search Report, Application No. EP 14191631.2-1405, 12 pages, dated Jun. 16, 2015.

European Patent Office, Authorized Officer, Isabel Perez-Mato, International Searching Report, Application No. PCT/AT2008/000232, 4 pages, dated Oct. 13, 2008, 4 pages.

International Bureau of WHIPO, Authorized officer Yolaine Cussac, International Preliminary Report on Patentability, International Application PCT/AT2008/000232, 10 pages, dated Jan. 5, 2010.

International Searching Authority, Written Opinion pertaining to International Application PCT/AT2008/000232, dated Oct. 12, 2008.

European Patent Office—Rijswijk Authorized Officer Rebecca Hix, International Search Report, dated Feb. 1, 2008, Application No. PCT/AT2007/000313, 3 pages.

International Searching Authority, Authorized Officer, Yolaine Cussac, Written Opinion pertaining to Application No, PCT/EP2009/052506, 8 pages, dated Nov. 2, 2010.

International Searching Authority, Authorized Officer Marie-Paul Toussaint, International Search Report and Written Opinion, Application No. PCT/EP2009/052509, 17 pages, dated Jun. 3, 2009.

European Patent Office, Communication pursuant to Article 94(3) EPC, European Patent Application No. 08 756 842.4, dated Jun. 14, 2010.

Rüker, F. "Modular Antibody Technology", F-Star Fact Sheet, online, Feb. 2008, www.boku.ac.at/fileadmin/BOKU-Topstories/20080702_Rueker_Factsheet.pdf.

* cited by examiner

SEQUENCE LISTING

<160> NUMBER OF SEQ ID NOS: 96

<210> SEQ ID NO 1
<211> LENGTH: 232
<212> TYPE: PRT
<213> ORGANISM: human

<400> SEQUENCE: 1

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 2
<211> LENGTH: 237
<212> TYPE: PRT
<213> ORGANISM: artificial
<220> FEATURE:
<223> OTHER INFORMATION: human IgG including randomized amino acid
      modifications
<220> FEATURE:
<221> NAME/KEY: misc_feature
<222> LOCATION: (144)..(146)
<223> OTHER INFORMATION: Xaa can be any naturally occurring amino acid
<220> FEATURE:
<221> NAME/KEY: misc_feature
<222> LOCATION: (198)..(205)
<223> OTHER INFORMATION: Xaa can be any naturally occurring amino acid
<220> FEATURE:
<221> NAME/KEY: misc_feature
<222> LOCATION: (208)..(209)
<223> OTHER INFORMATION: Xaa can be any naturally occurring amino acid

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Xaa
130                 135                 140

Xaa Xaa Gln Val Ser Leu Thr Cys Leu Val Lys Gly Phe Tyr Pro Ser
```

```
                145                 150                 155                 160
Asp Ile Ala Val Glu Trp Glu Ser Asn Gly Gln Pro Glu Asn Asn Tyr
                    165                 170                 175

Lys Thr Thr Pro Pro Val Leu Asp Ser Asp Gly Ser Phe Phe Leu Tyr
                    180                 185                 190

Ser Lys Leu Thr Val Xaa Xaa Xaa Xaa Xaa Xaa Arg Trp Xaa
                    195                 200                 205

Xaa Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 3
<211> LENGTH: 728
<212> TYPE: DNA
<213> ORGANISM: artificial
<220> FEATURE:
<223> OTHER INFORMATION: DNA Sequence for Cloning of modified IgG
<220> FEATURE:
<221> NAME/KEY: misc_feature
<222> LOCATION: (438)..(439)
<223> OTHER INFORMATION: n is a, c, g, or t
<220> FEATURE:
<221> NAME/KEY: misc_feature
<222> LOCATION: (441)..(442)
<223> OTHER INFORMATION: n is a, c, g, or t
<220> FEATURE:
<221> NAME/KEY: misc_feature
<222> LOCATION: (444)..(445)
<223> OTHER INFORMATION: n is a, c, g, or t
<220> FEATURE:
<221> NAME/KEY: misc_feature
<222> LOCATION: (600)..(601)
<223> OTHER INFORMATION: n is a, c, g, or t
<220> FEATURE:
<221> NAME/KEY: misc_feature
<222> LOCATION: (603)..(604)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (609)..(610)
<223> OTHER INFORMATION: n is a, c, g, or t
<220> FEATURE:
<221> NAME/KEY: misc_feature
<222> LOCATION: (612)..(613)
<223> OTHER INFORMATION: n is a, c, g, or t
<220> FEATURE:
<221> NAME/KEY: misc_feature
<222> LOCATION: (615)..(616)
<223> OTHER INFORMATION: n is a, c, g, or t
<220> FEATURE:
<221> NAME/KEY: misc_feature
<222> LOCATION: (618)..(619)
<223> OTHER INFORMATION: n is a, c, g, or t
<220> FEATURE:
<221> NAME/KEY: misc_feature
<222> LOCATION: (621)..(622)
<223> OTHER INFORMATION: n is a, c, g, or t
<220> FEATURE:
<221> NAME/KEY: misc_feature
<222> LOCATION: (630)..(631)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t

<400> SEQUENCE: 3
```

```
ccatggccga gcccaaatct tgtgacaaaa ctcacacatg cccaccgtgc ccagcacctg      60
aactcctggg gggaccgtca gtcttcctct tccccccaaa acccaaggac accctcatga     120
tctcccggac ccctgaggtc acatgcgtgg tggtggacgt gagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agcccctccca gcccccatcg    360 agaaaaccat ctccaaagcc aagggcagc ctcgagaacc acaggtgtac accctgcccc     420
catcccgtga cgagctcnns nnsnnscaag tcagcctgac ctgcctggtc aaaggcttct     480
atcccagcga catcgccgtg gagtgggaga gcaatgggca gccggagaac aactacaaga     540
ccacgcctcc cgtgctggac tccgacggct ccttcttcct ctacagcaag cttaccgtgn     600
nsnnsnnsnn snnsnnsnns nnsaggtggn nsnnsgggaa cgtcttctca tgctccgtga     660
tgcatgaggc tctgcacaac cactacacac agaagagcct ctccctgtct ccgggtaaag     720
cggccgca                                                              728
```

<210> SEQ ID NO 4
<211> LENGTH: 33
<212> TYPE: DNA
<213> ORGANISM: artificial
<220> FEATURE:
<223> OTHER INFORMATION: PCR primer EPKSNCO

<400> SEQUENCE: 4
ccatggccga gcccaaatct tgtgacaaaa ctc                                   33

<210> SEQ ID NO 5
<211> LENGTH: 30
<212> TYPE: DNA
<213> ORGANISM: artificial
<220> FEATURE:
<223> OTHER INFORMATION: PCR primer CH3LSAC

<400> SEQUENCE: 5
agtcgagctc gtcacgggat gggggcaggg                                       30

<210> SEQ ID NO 6
<211> LENGTH: 41
<212> TYPE: DNA
<213> ORGANISM: artificial
<220> FEATURE:
<223> OTHER INFORMATION: PCR primer CH3CSAC
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 6
gtacgagctc nnsnnsnnsc aagtcagcct gacctgcctg g                         41

<210> SEQ ID NO 7
<211> LENGTH: 32
<212> TYPE: DNA
<213> ORGANISM: artificial

```
<220> FEATURE:
<223> OTHER INFORMATION: PCR primer CH3CHIN

<400> SEQUENCE: 7
tgccaagctt gctgtagagg aagaaggagc cg                                      32

<210> SEQ ID NO 8
<211> LENGTH: 59
<212> TYPE: DNA
<213> ORGANISM: artificial
<220> FEATURE:
<223> OTHER INFORMATION: PCR primer CH3RHIN
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 8
tgccaagctt accgtgnnsn nsnnsaggtg gnnsnnsggg aacgtcttct catgctccg         59

<210> SEQ ID NO 9
<211> LENGTH: 33
<212> TYPE: DNA
<213> ORGANISM: artificial
<220> FEATURE:
<223> OTHER INFORMATION: PCR primer CH3RNOT

<400> SEQUENCE: 9
agttgcggcc gctttacccg gagacaggga gag                                    33

<210> SEQ ID NO 10
<211> LENGTH: 25
<212> TYPE: PRT
<213> ORGANISM: artificial
<220> FEATURE:
<223> OTHER INFORMATION: junction region

<400> SEQUENCE: 10

Ser Pro Gly Lys Ala Ala Ala Glu Gln Lys Leu Ile Ser Glu Glu Asp
1               5                   10                  15

Leu Asn Gly Ala Ala Thr Val Glu Ser
            20                  25

<210> SEQ ID NO 11
<211> LENGTH: 662
<212> TYPE: PRT
<213> ORGANISM: artificial
<220> FEATURE:
<223> OTHER INFORMATION: amino acid sequence of FcabRGD4L

<400> SEQUENCE: 11

Glu Pro Lys Ser Cys Asp Lys Thr His Thr Cys Pro Pro Cys Pro Ala
1               5                   10                  15
```

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Gly Cys Arg Gly Asp Cys Leu Ser Arg Trp Gln
            195                 200                 205

Gln Gly Asn Val Phe Ser Cys Ser Val Met His Glu Ala Leu His Asn
            210                 215                 220

His Tyr Thr Gln Lys Ser Leu Ser Leu Ser Pro Gly Lys Glu Gly Gly
225                 230                 235                 240

Gly Ser Ala Ala Ala Glu Gln Lys Leu Ile Ser Glu Glu Asp Leu Asn
            245                 250                 255

Gly Ala Ala Thr Val Glu Ser Cys Leu Ala Lys Pro His Thr Glu Asn
            260                 265                 270

Ser Phe Thr Asn Val Trp Lys Asp Asp Lys Thr Leu Asp Arg Tyr Ala
            275                 280                 285

Asn Tyr Glu Gly Cys Leu Trp Asn Ala Thr Gly Val Val Val Cys Thr
            290                 295                 300

Gly Asp Glu Thr Gln Cys Tyr Gly Thr Trp Val Pro Ile Gly Leu Ala
305                 310                 315                 320

Ile Pro Glu Asn Glu Gly Gly Ser Glu Gly Gly Ser Glu Gly
            325                 330                 335

Gly Gly Ser Glu Gly Gly Thr Lys Pro Pro Glu Tyr Gly Asp Thr
            340                 345                 350

Pro Ile Pro Gly Tyr Thr Tyr Ile Asn Pro Leu Asp Gly Thr Tyr Pro
            355                 360                 365

Pro Gly Thr Glu Gln Asn Pro Ala Asn Pro Asn Pro Ser Leu Glu Glu
            370                 375                 380

Ser Gln Pro Leu Asn Thr Phe Met Phe Gln Asn Asn Arg Phe Arg Asn
385                 390                 395                 400

Arg Gln Gly Ala Leu Thr Val Tyr Thr Gly Thr Val Thr Gln Gly Thr
                405                 410                 415

Asp Pro Val Lys Thr Tyr Tyr Gln Tyr Thr Pro Val Ser Ser Lys Ala
            420                 425                 430
```

Met Tyr Asp Ala Tyr Trp Asn Gly Lys Phe Arg Asp Cys Ala Phe His
                435                 440                 445

Ser Gly Phe Asn Glu Asp Pro Phe Val Cys Tyr Gln Gly Gln Ser
    450                 455                 460

Ser Asp Leu Pro Gln Pro Pro Val Asn Ala Gly Gly Ser Gly Gly
465                 470                 475                 480

Gly Ser Gly Gly Gly Ser Gly Gly Gly Ser Gly Gly Gly Ser
                485                 490                 495

Glu Gly Gly Gly Ser Glu Gly Gly Gly Ser Gly Gly Gly Ser
                500                 505                 510

Gly Asp Phe Asp Tyr Glu Lys Met Ala Asn Ala Asn Lys Gly Ala Met
            515                 520                 525

Thr Glu Asn Ala Asp Glu Asn Ala Leu Gln Ser Asp Ala Lys Gly Lys
        530                 535                 540

Leu Asp Ser Val Ala Thr Asp Tyr Gly Ala Ala Ile Asp Gly Phe Ile
545                 550                 555                 560

Gly Asp Val Ser Gly Leu Ala Asn Gly Asn Gly Ala Thr Gly Asp Phe
                565                 570                 575

Ala Gly Ser Asn Ser Gln Met Ala Gln Val Gly Asp Gly Asp Asn Ser
            580                 585                 590

Pro Leu Met Asn Asn Phe Arg Gln Tyr Leu Pro Ser Leu Pro Gln Ser
        595                 600                 605

Val Glu Cys Arg Pro Tyr Val Phe Gly Ala Gly Lys Pro Tyr Glu Phe
    610                 615                 620

Ser Ile Asp Cys Asp Lys Ile Asn Leu Phe Arg Gly Val Phe Ala Phe
625                 630                 635                 640

Leu Leu Tyr Val Ala Thr Phe Met Tyr Val Phe Ser Thr Phe Ala Asn
                645                 650                 655

Ile Leu His Lys Glu Ser
                660

<210> SEQ ID NO 12
<211> LENGTH: 5200
<212> TYPE: DNA
<213> ORGANISM: artificial
<220> FEATURE:
<223> OTHER INFORMATION: vector pHENFcabRGD4

<400> SEQUENCE: 12

```
gacgaaaggg cctcgtgata cgcctatttt tataggttaa tgtcatgata ataatggttt      60
cttagacgtc aggtggcact tttcggggaa atgtgcgcgg aaccccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacgatg     540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
```

```
acgagcgtga caccacgatg cctgtagcaa tggcaacaac gttgcgcaaa ctattaactg    780
gcgaactact tactctagct tcccggcaac aattaataga ctggatggag cggataaag     840 ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttt    1860 gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt aagcttgcat gcaaattcta tttcaaggag acagtcataa   2280
tgaaatacct attgcctacg gcagccgctg gattgttatt actcgcggcc cagccggcca   2340
tggccgagcc caaatcttgt gacaaaactc acacatgccc accgtgccca gcacctgaac   2400
tcctgggggg accgtcagtc ttcctcttcc cccaaaaacc caaggacacc ctcatgatct   2460
cccggacccc tgaggtcaca tgcgtggtgg tggacgtgag ccacgaagac cctgaggtca   2520
agttcaactg gtacgtggac ggcgtggagg tgcataatgc caagacaaag ccgcgggagg   2580
agcagtacaa cagcacgtac cgtgtggtca gcgtcctcac cgtcctgcac caggactggc   2640
tgaatggcaa ggagtacaag tgcaaggtct ccaacaaagc cctcccagcc cccatcgaga   2700
aaaccatctc caaagccaaa gggcagcccc gagaaccaca ggtgtacacc ctgcccccat   2760
cccgggatga gctgaccaag aaccaggtca gcctgacctg cctggtcaaa ggcttctatc   2820
ccagcgacat cgccgtggag tgggagagca atgggcagcc ggagaacaac tacaagacca   2880
cgcctcccgt gctggactcc gacggctcct tcttcctcta cagcaagctt accgtggggtt   2940 gccgcggtga ttgtctgagc aggtggcagc aggggaacgt cttctcatgc tccgtgatgc   3000
atgaggctct gcacaaccac tacacgcaga agagcctctc cctgtctccg ggtaaagcgg   3060
ccgcagaaca aaaaactcatc tcagaagagg atctgaatgg ggccgcatag actgttgaaa   3120
```

```
gttgtttagc aaaacctcat acagaaaatt catttactaa cgtctggaaa gacgacaaaa    3180 cttttagatcg ttacgctaac tatgagggct gtctgtggaa tgctacaggc gttgtggttt    3240
gtactggtga cgaaactcag tgttacggta catgggttcc tattgggctt gctatccctg    3300
aaaatgaggg tggtggctct gagggtggcg gttctgaggg tggcggttct gagggtggcg    3360
gtactaaacc tcctgagtac ggtgatacac ctattccggg ctatacttat atcaaccctc    3420
tcgacggcac ttatccgcct ggtactgagc aaaaccccgc taatcctaat ccttctcttg    3480
aggagtctca gcctcttaat actttcatgt ttcagaataa taggttccga ataggcagg    3540 gtgcattaac tgtttatacg ggcactgtta ctcaaggcac tgaccccgtt aaaacttatt    3600
accagtacac tcctgtatca tcaaaagcca tgtatgacgc ttactggaac ggtaaattca    3660
gagactgcgc tttccattct ggctttaatg aggatccatt cgtttgtgaa tatcaaggcc    3720
aatcgtctga cctgcctcaa cctcctgtca atgctggcgg cggctctggt ggtggttctg    3780
gtggcggctc tgagggtggc ggctctgagg gtggcggttc tgagggtggc ggctctgagg    3840
gtggcggttc cggtggcggc tccggttccg gtgattttga ttatgaaaaa atggcaaacg    3900
ctaataaggg ggctatgacc gaaaatgccg atgaaaacgc gctacagtct gacgctaaag    3960
gcaaacttga ttctgtcgct actgattacg gtgctgctat cgatggtttc attggtgacg    4020
tttccggcct tgctaatggt aatggtgcta ctggtgattt tgctggctct aattcccaaa    4080
tggctcaagt cggtgacggt gataattcac ctttaatgaa taatttccgt caatatttac    4140
cttctttgcc tcagtcggtt gaatgtcgcc cttatgtctt tggcgctggt aaaccatatg    4200
aattttctat tgattgtgac aaaataaact tattccgtgg tgtctttgcg tttcttttat    4260
atgttgccac ctttatgtat gtattttcga cgtttgctaa catactgcat aaggagtctt    4320
aataagaatt cactggccgt cgttttacaa cgtcgtgact gggaaaaccc tggcgttacc    4380
caacttaatc gccttgcagc acatccccct ttcgccagct ggcgtaatag cgaagaggcc    4440
cgcaccgatc gcccttccca acagttgcgc agcctgaatg gcgaatggcg cctgatgcgg    4500
tattttctcc ttacgcatct gtgcggtatt tcacaccgca cgtcaaagca accatagtac    4560
gcgccctgta gcggcgcatt aagcgcggcg ggtgtggtgg ttacgcgcag cgtgaccgct    4620
acacttgcca gcgccctagc gcccgctcct ttcgctttct tcccttcctt tctcgccacg    4680
ttcgccggct ttccccgtca agctctaaat cgggggctcc ctttagggtt ccgatttagt    4740
gctttacggc acctcgaccc caaaaaactt gatttgggtg atggttcacg tagtgggcca    4800
tcgccctgat agacggtttt tcgccctttg acgttggagt ccacgttctt taatagtgga    4860
ctcttgttcc aaactggaac aacactcaac cctatctcgg gctattcttt tgatttataa    4920
gggattttgc cgatttcggc ctattggtta aaaaatgagc tgatttaaca aaaatttaac    4980
gcgaatttta acaaaatatt aacgtttaca attttatggt gcactctcag tacaatctgc    5040
tctgatgccg catagttaag ccagccccga cacccgccaa cacccgctga cgcgccctga    5100
cgggcttgtc tgctcccggc atccgcttac agacaagctg tgaccgtctc cgggagctgc    5160
atgtgtcaga ggttttcacc gtcatcaccg aaacgcgcga                          5200
```

<210> SEQ ID NO 13
<211> LENGTH: 48
<212> TYPE: DNA
<213> ORGANISM: artificial
<220> FEATURE:
<223> OTHER INFORMATION: CH3rlink

<400> SEQUENCE: 13
actagcggcc gcagagccac caccctcctt acccggagac agggagag            48

<210> SEQ ID NO 14
<211> LENGTH: 5215
<212> TYPE: DNA
<213> ORGANISM: artificial
<220> FEATURE:
<223> OTHER INFORMATION: vector pHENFcabRGD4L

<400> SEQUENCE: 14

| gacgaaaggg | cctcgtgata | cgcctatttt | tataggttaa | tgtcatgata | ataatggttt | 60 |
| cttagacgtc | aggtggcact | tttcggggaa | atgtgcgcgg | aacccctatt | tgtttatttt | 120 |
| tctaaataca | ttcaaatatg | tatccgctca | tgagacaata | accctgataa | atgcttcaat | 180 |
| aatattgaaa | aaggaagagt | atgagtattc | aacatttccg | tgtcgccctt | attccctttt | 240 |
| ttgcggcatt | ttgccttcct | gttttttgctc | acccagaaac | gctggtgaaa | gtaaaagatg | 300 |
| ctgaagatca | gttgggtgca | cgagtgggtt | acatcgaact | ggatctcaac | agcggtaaga | 360 |
| tccttgagag | ttttcgcccc | gaagaacgtt | ttccaatgat | gagcactttt | aaagttctgc | 420 |
| tatgtggcgc | ggtattatcc | cgtattgacg | ccgggcaaga | gcaactcggt | cgccgcatac | 480 |
| actattctca | gaatgacttg | gttgagtact | caccagtcac | agaaaagcat | cttacggatg | 540 |
| gcatgacagt | aagagaatta | tgcagtgctg | ccataaccat | gagtgataac | actgcggcca | 600 |
| acttacttct | gacaacgatc | ggaggaccga | aggagctaac | cgcttttttg | cacaacatgg | 660 |
| gggatcatgt | aactcgcctt | gatcgttggg | aaccggagct | gaatgaagcc | ataccaaacg | 720 |
| acgagcgtga | caccacgatg | cctgtagcaa | tggcaacaac | gttgcgcaaa | ctattaactg | 780 |
| gcgaactact | tactctagct | tcccggcaac | aattaataga | ctggatggag | gcggataaag | 840 |
| ttgcaggacc | acttctgcgc | tcggcccttc | cggctggctg | gtttattgct | gataaatctg | 900 |
| gagccggtga | gcgtgggtct | cgcggtatca | ttgcagcact | ggggccagat | ggtaagccct | 960 |
| cccgtatcgt | agttatctac | acgacgggga | gtcaggcaac | tatggatgaa | cgaaatagac | 1020 |
| agatcgctga | gataggtgcc | tcactgatta | agcattggta | actgtcagac | caagtttact | 1080 |
| catatatact | ttagattgat | ttaaaacttc | attttttaatt | taaaaggatc | taggtgaaga | 1140 |
| tcctttttga | taatctcatg | accaaaatcc | cttaacgtga | gttttcgttc | cactgagcgt | 1200 |
| cagaccccgt | agaaaagatc | aaaggatctt | cttgagatcc | tttttttctg | cgcgtaatct | 1260 |
| gctgcttgca | acaaaaaaa | ccaccgctac | cagcggtggt | ttgtttgccg | gatcaagagc | 1320 |
| taccaactct | ttttccgaag | gtaactggct | tcagcagagc | gcagatacca | aatactgtcc | 1380 |
| ttctagtgta | gccgtagtta | ggccaccact | tcaagaactc | tgtagcaccg | cctacatacc | 1440 |
| tcgctctgct | aatcctgtta | ccagtggctg | ctgccagtgg | cgataagtcg | tgtcttaccg | 1500 |
| ggttggactc | aagacgatag | ttaccggata | aggcgcagcg | gtcgggctga | acggggggtt | 1560 |
| cgtgcacaca | gcccagcttg | gagcgaacga | cctacaccga | actgagatac | ctacagcgtg | 1620 |
| agcattgaga | aagcgccacg | cttcccgaag | ggagaaaggc | ggacaggtat | ccggtaagcg | 1680 |
| gcagggtcgg | aacaggagag | cgcacgaggg | agcttccagg | gggaaacgcc | tggtatcttt | 1740 |
| atagtcctgt | cgggtttcgc | cacctctgac | ttgagcgtcg | atttttgtga | tgctcgtcag | 1800 |
| gggggcggag | cctatggaaa | aacgccagca | acgcggcctt | tttacggttc | ctggccttttt | 1860 |
| gctggccttt | tgctcacatg | ttctttcctg | cgttatcccc | tgattctgtg | ataaccgta | 1920 |
| ttaccgcctt | tgagtgagct | gataccgctc | gccgcagccg | aacgaccgag | cgcagcgagt | 1980 |

```
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt aagcttgcat gcaaattcta tttcaaggag acagtcataa   2280
tgaaatacct attgcctacg gcagccgctg gattgttatt actcgcggcc cagccggcca   2340
tggccgagcc caaatcttgt gacaaaactc acacatgccc accgtgccca gcacctgaac   2400
tcctgggggg accgtcagtc ttcctcttcc cccaaaaacc caaggacacc ctcatgatct   2460
cccggacccc tgaggtcaca tgcgtggtgg tggacgtgag ccacgaagac cctgaggtca   2520
agttcaactg gtacgtggac ggcgtggagg tgcataatgc caagacaaag ccgcgggagg   2580
agcagtacaa cagcacgtac cgtgtggtca gcgtcctcac cgtcctgcac caggactggc   2640
tgaatggcaa ggagtacaag tgcaaggtct ccaacaaagc cctcccagcc cccatcgaga   2700
aaaccatctc caaagccaaa gggcagcccc gagaaccaca ggtgtacacc ctgcccccat   2760
cccgggatga gctgaccaag aaccaggtca gcctgacctg cctggtcaaa ggcttctatc   2820
ccagcgacat cgccgtggag tgggagagca atgggcagcc ggagaacaac tacaagacca   2880
cgcctcccgt gctggactcc gacggctcct tcttcctcta cagcaagctt accgtggggtt   2940
```

```
tgcataagga gtcttaataa gaattcactg gccgtcgttt tacaacgtcg tgactgggaa   4380
aaccctggcg ttacccaact taatcgcctt gcagcacatc cccctttcgc cagctggcgt   4440
aatagcgaag aggcccgcac cgatcgccct tcccaacagt tgcgcagcct gaatggcgaa   4500
tggcgcctga tgcggtattt tctccttacg catctgtgcg gtatttcaca ccgcacgtca   4560
aagcaaccat agtacgcgcc ctgtagcggc gcattaagcg cggcgggtgt ggtggttacg   4620
cgcagcgtga ccgctacact tgccagcgcc ctagcgcccg ctcctttcgc tttcttccct   4680
tcctttctcg ccacgttcgc cggctttccc cgtcaagctc taaatcgggg ctcccttta    4740
gggttccgat ttagtgcttt acggcacctc gaccccaaaa aacttgattt gggtgatggt   4800
tcacgtagtg ggccatcgcc ctgatagacg gttttttcgcc ctttgacgtt ggagtccacg  4860
ttctttaata gtggactctt gttccaaact ggaacaacac tcaaccctat ctcgggctat   4920
tcttttgatt tataagggat tttgccgatt tcggcctatt ggttaaaaaa tgagctgatt   4980
taacaaaaat ttaacgcgaa ttttaacaaa atattaacgt ttacaatttt atggtgcact   5040
ctcagtacaa tctgctctga tgccgcatag ttaagccagc cccgacaccc gccaacaccc   5100
gctgacgcgc cctgacgggc ttgtctgctc ccggcatccg cttacagaca agctgtgacc   5160
gtctccggga gctgcatgtg tcagaggttt tcaccgtcat caccgaaacg cgcga         5215
```

<210> SEQ ID NO 15
<211> LENGTH: 5013
<212> TYPE: DNA
<213> ORGANISM: artificial
<220> FEATURE:
<223> OTHER INFORMATION: vector pYD1dX

<400> SEQUENCE: 15

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
taacagatat ataaatgcaa aaactgcata accactttaa ctaatacttt caacattttc   360
ggtttgtatt acttcttatt caatgtaat aaaagtatca acaaaaaatt gttaatatac    420
ctctatactt taacgtcaag gagaaaaaac cccggatcgg actactagca gctgtaatac   480
gactcactat agggaatatt aagctaattc tacttcatac attttcaatt aagatgcagt   540
tacttcgctg ttttttcaata ttttctgtta ttgcttcagt tttagcacag gaactgacaa   600
ctatatgcga gcaaatcccc tcaccaactt tagaatcgac gccgtactct tgtcaacga    660
ctactatttt ggccaacggg aaggcaatgc aaggagtttt tgaatattac aaatcagtaa   720
cgtttgtcag taattgcggt tctcacccct caacaactag caaaggcagc cccataaaca   780
cacagtatgt ttttaagctt ctgcaggcta gtggtgtggt ggttctggt ggtggtggt      840
ctggtggtgg tggttctgct agcatgactg gtggacagca aatgggtcgg gatctgtacg   900
acgatgacga taaggtacca ggatccagtg tggtggaatt ctgcagatat ccagcacagt   960
ggcggccgct cgatcgagtc tagagggccc ttcgaaggta agcctatccc taaccctctc  1020
ctcggtctcg attctacgcg taccggtcat catccatc accattgagt ttaaacccgc    1080
tgatctgata caacagtgt agatgtaaca aaatcgactt tgttcccact gtactttag    1140
ctcgtacaaa atacaatata cttttcattt ctccgtaaac aacatgtttt cccatgtaat  1200
```

```
atccttttct attttttcgtt ccgttaccaa ctttacacat actttatata gctattcact    1260
tctatacact aaaaaactaa gacaatttta attttgctgc ctgccatatt tcaatttgtt    1320
ataaattcct ataatttatc ctattagtag ctaaaaaaag atgaatgtga atcgaatcct    1380
aagagaattg ggcaagtgca caaacaatac ttaaataaat actactcagt aataacctat    1440
ttcttagcat ttttgacgaa atttgctatt ttgttagagt cttttacacc atttgtctcc    1500
acacctccgc ttacatcaac accaataacg ccatttaatc taagcgcatc accaacattt    1560
tctggcgtca gtccaccagc taacataaaa tgtaagctct cggggctctc ttgccttcca    1620
acccagtcag aaatcgagtt ccaatccaaa agttcacctg tcccacctgc ttctgaatca    1680
aacaagggaa taaacgaatg aggtttctgt gaagctgcac tgagtagtat gttgcagtct    1740
tttgaaaata cgagtctttt aataactggc aaaccgagga actcttggta ttcttgccac    1800
gactcatctc cgtgcagttg gacgatatca atgccgtaat cattgaccag agccaaaaca    1860
tcctccttag gttgattacg aaacacgcca accaagtatt tcggagtgcc tgaactattt    1920
ttatatgctt ttacaagact tgaaattttc cttgcaataa ccgggtcaat tgttctcttt    1980
ctattgggca cacatataat acccagcaag tcagcatcgg aatctagagc acattctgcg    2040
gcctctgtgc tctgcaagcc gcaaactttc accaatggac cagaactacc tgtgaaatta    2100
ataacagaca tactccaagc tgcctttgtg tgcttaatca cgtatactca cgtgctcaat    2160
agtcaccaat gccctccctc ttggccctct ccttttcttt tttcgaccga atttcttgaa    2220
gacgaaaggg cctcgtgata cgcctatttt tataggttaa tgtcatgata taatggtttt    2280
cttaggacgg atcgcttgcc tgtaacttac acgcgcctcg tatcttttaa tgatggaata    2340
atttgggaat ttactctgtg tttatttatt tttatgtttt gtatttggat tttagaaagt    2400
aaataaagaa ggtagaagag ttacggaatg aagaaaaaaa aataaacaaa ggtttaaaaa    2460
atttcaacaa aaagcgtact ttacatatat atttattaga caagaaaagc agattaaata    2520
gatatacatt cgattaacga taagtaaaat gtaaaatcac aggattttcg tgtgtggtct    2580
tctacacaga caagatgaaa caattcggca ttaatacctg agagcaggaa gagcaagata    2640
aaaggtagta tttgttggcg atcccctag agtcttttac atcttcggaa aacaaaaact    2700
attttttctt taatttcttt ttttactttc tattttaat ttatatattt atattaaaaa    2760
atttaaatta taattatttt tatagcacgt gatgaaaagg acccaggtgg cacttttcgg    2820
ggaaatgtgc gcggaacccc tatttgttta tttttctaaa tacattcaaa tatgtatccg    2880
ctcatgagac aataaccctg ataaatgctt caataatatt gaaaaggaa gagtatgagt    2940 attcaacatt tccgtgtcgc ccttattccc tttttgcgg cattttgcct tcctgttttt    3000
gctcacccag aaacgctggt gaaagtaaaa gatgctgaag atcagttggg tgcacgagtg    3060
ggttacatcg aactggatct caacagcggt aagatccttg agagttttcg ccccgaagaa    3120
cgttttccaa tgatgagcac ttttaaagtt ctgctatgtg gcgcggtatt atcccgtgtt    3180
gacgccgggc aagagcaact cggtcgccgc atacactatt ctcagaatga cttggttgag    3240
tactcaccag tcacagaaaa gcatcttacg gatggcatga cagtaagaga attatgcagt    3300
gctgccataa ccatgagtga taacactgcg gccaacttac ttctgacaac gatcggagga    3360
ccgaaggagc taaccgcttt tttgcacaac atggggatc atgtaactcg ccttgatcgt    3420
tgggaaccgg agctgaatga agccatacca aacgacgagc gtgacaccac gatgcctgta    3480
gcaatggcaa caacgttgcg caaactatta actggcgaac tacttactct agcttcccgg    3540
```

```
caacaattaa tagactggat ggaggcggat aaagttgcag gaccacttct gcgctcggcc    3600
cttccggctg gctggtttat tgctgataaa tctggagccg gtgagcgtgg gtctcgcggt    3660
atcattgcag cactggggcc agatggtaag ccctcccgta tcgtagttat ctacacgacg    3720
ggcagtcagg caactatgga tgaacgaaat agacagatcg ctgagatagg tgcctcactg    3780
attaagcatt ggtaactgtc agaccaagtt tactcatata ctttagat tgatttaaaa     3840
cttcattttt aatttaaaag gatctaggtg aagatccttt ttgataatct catgaccaaa    3900
atcccttaac gtgagttttc gttccactga gcgtcagacc ccgtagaaaa gatcaaagga    3960
tcttcttgag atcctttttt tctgcgcgta atctgctgct tgcaaacaaa aaaaccaccg    4020
ctaccagcgg tggtttgttt gccggatcaa gagctaccaa ctcttttttcc gaaggtaact    4080
ggcttcagca gagcgcagat accaaatact gtccttctag tgtagccgta gttaggccac    4140
cacttcaaga actctgtagc accgcctaca tacctcgctc tgctaatcct gttaccagtg    4200
gctgctgcca gtggcgataa gtcgtgtctt accgggttgg actcaagacg atagttaccg    4260
gataaggcgc agcggtcggg ctgaacgggg gttcgtgca cacagcccag cttggagcga    4320
acgacctaca ccgaactgag atacctacag cgtgagcatt gagaaagcgc cacgcttccc    4380
gaagggagaa aggcggacag gtatccggta agcggcaggg tcggaacagg agagcgcacg    4440
agggagcttc caggggggaa cgcctggtat ctttatagtc ctgtcgggtt cgccacctc    4500
tgacttgagc gtcgattttt gtgatgctcg tcaggggggc cgagcctatg gaaaaacgcc    4560
agcaacgcgg cctttttacg gttcctggcc ttttgctggc cttttgctca catgttcttt    4620
cctgcgttat cccctgattc tgtggataac cgtattaccg cctttgagtg agctgatacc    4680
gctcgccgca gccgaacgac cgagcgcagc gagtcagtga gcgaggaagc ggaagagcgc    4740
ccaatacgca aaccgcctct ccccgcgcgt tggccgattc attaatgcag ctggcacgac    4800
aggtttcccg actggaaagc gggcagtgag cgcaacgcaa ttaatgtgag ttacctcact    4860
cattaggcac cccaggcttt acactttatg cttccggctc ctatgttgtg tggaattgtg    4920
agcggataac aatttcacac aggaaacagc tatgaccatg attacgccaa gctcggaatt    4980
aaccctcact aaagggaaca aaagctggct agt                                 5013
```

<210> SEQ ID NO 16  
<211> LENGTH: 5971  
<212> TYPE: DNA  
<213> ORGANISM: artificial  
<220> FEATURE:  
<223> OTHER INFORMATION: vector pYD1dXFc

<400> SEQUENCE: 16

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg ttttttcaata ttttctgtta ttgcttcagt tttagcacag gaactgacaa    600
```

```
ctatatgcga gcaaatcccc tcaccaactt tagaatcgac gccgtactct tgtcaacga    660
ctactatttt ggccaacggg aaggcaatgc aaggagtttt tgaatattac aaatcagtaa   720
cgtttgtcag taattgcggt tctcacccct caacaactag caaaggcagc cccataaaca   780
cacagtatgt ttttaagctt ctgcaggcta gtggtggtgg tggttctggt ggtggtggtt   840
ctggtggtgg tggttctgct agcatgactg gtggacagca aatgggtcgg atctgtacg   900
acgatgacga taaggtacca ggatccgcta gcaccaaggg ccccagcgtg ttccctctgg   960
cccccagctc aagagcacc tccggcggca ccgccgccct gggctgcctg gtgaaggatt   1020
acttcccaga gcccgtgacc gtgagctgga acagcggcgc cctgaccagc ggcgtgcaca   1080
cctttcccgc cgtgctgcag tccagcggcc tgtactccct gagcagcgtg gtgaccgtgc   1140
ccagcagcag cctgggcacc cagacctaca tctgcaatgt gaaccacaag cccagcaata   1200
ccaaggtgga taagaaggtg gagcccaaga gcagcgacaa gacacacacg tgtccccat    1260
gtcccgcccc tgagctgctg ggcggcccctt ccgtgttcct gttccctccc aagccaaagg   1320
acaccctgat gatctcccgg acccctgagg tgacctgtgt ggtggtggac gtgagccacg   1380
aggacccaga ggtgaagttc aactggtacg tggacggcgt ggaggtgcac aacgccaaga   1440
ccaagcctag agaggagcag tacaacagca cctaccgcgt ggtgagcgtg ctgaccgtgc   1500
tgcaccagga ttggctgaat ggcaaggagt acaagtgcaa ggtgagcaac aaggccctgc   1560
ctgccccat cgagaagacc atctccaagg ccaagggcca gcctcgagaa ccacaggtgt   1620
acaccctgcc cccatcccgg gatgagctga ccaagaacca ggtcagcctg acctgcctgg   1680
tcaaaggctt ctatcccagc gacatcgccg tggagtggga gagcaatggg cagccggaga   1740
acaactacaa gaccacgcct cccgtgctgg actccgacgg ctccttcttc ctctacagca   1800
agctcaccgt ggacaagagc aggtggcagc aggggaacgt cttctcatgc tccgtgatgc   1860
atgaggctct gcacaaccac tacacacaga gagcctctc cctgtctccg ggtaaatgag    1920
cggccgctcg atcgagtcta gagggccctt cgaaggtaag cctatcccta accctctcct   1980
cggtctcgat tctacgcgta ccggtcatca tcaccatcac cattgagttt aaacccgctg   2040
atctgataac aacagtgtag atgtaacaaa atcgactttg ttcccactgt acttttagct   2100
cgtacaaaat acaatatact tttcatttct ccgtaaacaa catgttttcc catgtaatat   2160
ccttttctat ttttcgttcc gttaccaact ttacacatac tttatatagc tattcacttc   2220
tatacactaa aaaactaaga caattttaat tttgctgcct gccatatttc aatttgttat   2280
aaattcctat aatttatcct attagtagct aaaaaaagat gaatgtgaat cgaatcctaa   2340
gagaattggg caagtgcaca aacaatactt aaataaatac tactcagtaa taacctatt    2400
cttagcattt ttgacgaaat ttgctatttt gttagagtct tttacaccat tgtctccac    2460
acctccgctt acatcaacac caataacgcc atttaatcta agcgcatcac caacatttc    2520
tggcgtcagt ccaccagcta acataaaatg taagctctcg ggctctctt gccttccaac    2580
ccagtcagaa atcgagttcc aatccaaaag ttcacctgtc ccacctgctt ctgaatcaaa   2640
caagggaata aacgaatgag gtttctgtga agctgcactg agtagtatgt tgcagtcttt   2700
tggaaatacg agtctttaa taactggcaa accgaggaac tcttggtatt cttgccacga    2760
ctcatctccg tgcagttgga cgatatcaat gccgtaatca ttgaccagag ccaaaacatc   2820
ctccttaggt tgattacgaa acacgccaac caagtatttc ggagtgcctg aactatttt    2880
atatgctttt acaagacttg aaattttcct tgcaataacc gggtcaattg ttctctttct   2940
```

```
attgggcaca catataatac ccagcaagtc agcatcggaa tctagagcac attctgcggc    3000
ctctgtgctc tgcaagccgc aaactttcac caatggacca gaactacctg tgaaattaat    3060
aacagacata ctccaagctg cctttgtgtg cttaatcacg tatactcacg tgctcaatag    3120
tcaccaatgc cctccctctt ggccctctcc ttttcttttt tcgaccgaat tcttgaaga    3180 cgaaagggcc tcgtgatacg cctattttta taggttaatg tcatgataat aatggtttct    3240
taggacggat cgcttgcctg taacttacac gcgcctcgta tcttttaatg atggaataat    3300
ttgggaattt actctgtgtt tatttatttt tatgttttgt atttggattt tagaaagtaa    3360
ataaagaagg tagaagagtt acggaatgaa gaaaaaaaaa taaacaaagg tttaaaaaat    3420
ttcaacaaaa agcgtacttt acatatatat ttattagaca agaaaagcag attaaataga    3480
tatacattcg attaacgata agtaaaatgt aaaatcacag gattttcgtg tgtggtcttc    3540
tacacagaca agatgaaaca attcggcatt aatacctgag agcaggaaga gcaagataaa    3600
aggtagtatt tgttggcgat cccctagag tcttttacat cttcggaaaa caaaaactat    3660
tttttcttta atttcttttt ttactttcta ttttaatttt atatatttat attaaaaaat    3720
ttaaattata attattttta tagcacgtga tgaaaaggac ccaggtggca cttttcgggg    3780
aaatgtgcgc ggaacccccta tttgtttatt tttctaaata cattcaaata tgtatccgct    3840
catgagacaa taaccctgat aaatgcttca ataatattga aaaggaaga gtatgagtat    3900 tcaacatttc cgtgtcgccc ttattccctt ttttgcggca ttttgccttc ctgttttgc    3960 tcacccagaa acgctggtga agtaaaaga tgctgaagat cagttgggtg cacgagtggg    4020
ttacatcgaa ctggatctca acagcggtaa gatccttgag agttttcgcc ccgaagaacg    4080
ttttccaatg atgagcactt ttaaagttct gctatgtggc gcggtattat cccgtgttga    4140
cgccgggcaa gagcaactcg gtcgccgcat acactattct cagaatgact tggttgagta    4200
ctcaccagtc acagaaaagc atcttacgga tggcatgaca gtaagagaat tatgcagtgc    4260
tgccataacc atgagtgata acactgcggc caacttactt ctgacaacga tcggaggacc    4320
gaaggagcta accgcttttt tgcacaacat gggggatcat gtaactcgcc ttgatcgttg    4380
ggaaccggag ctgaatgaag ccataccaaa cgacgagcgt gacaccacga tgcctgtagc    4440
aatggcaaca acgttgcgca aactattaac tggcgaacta cttactctag cttcccggca    4500
acaattaata gactggatgg aggcggataa agttgcagga ccacttctgc gctcggccct    4560
tccggctggc tggtttattg ctgataaatc tggagccggt gagcgtgggt ctcgcggtat    4620
cattgcagca ctggggccag atggtaagcc ctcccgtatc gtagttatct acacgacggg    4680
cagtcaggca actatggatg aacgaaatag acagatcgct gagataggtg cctcactgat    4740
taagcattgg taactgtcag accaagttta ctcatatata ctttagattg atttaaaact    4800
tcatttttaa tttaaaagga tctaggtgaa gatcctttt gataatctca tgaccaaaat    4860
cccttaacgt gagttttcgt tccactgagc gtcagacccc gtagaaaaga tcaaggatc    4920 ttcttgagat cctttttttc tgcgcgtaat ctgctgcttg caaacaaaaa aaccaccgct    4980
accagcggtg gtttgtttgc cggatcaaga gctaccaact ctttttccga aggtaactgg    5040
cttcagcaga gcgcagatac caaatactgt ccttctagtg tagccgtagt taggccacca    5100
cttcaagaac tctgtagcac cgcctacata cctcgctctg ctaatcctgt taccagtggc    5160
tgctgccagt ggcgataagt cgtgtcttac cgggttggac tcaagacgat agttaccgga    5220
taaggcgcag cggtcgggct gaacggggggg ttcgtgcaca cagcccagct tggagcgaac    5280
gacctacacc gaactgagat acctacagcg tgagcattga gaaagcgcca cgcttcccga    5340
```

```
agggagaaag gcggacaggt atccggtaag cggcagggtc ggaacaggag agcgcacgag      5400
ggagcttcca gggggaacg cctggtatct ttatagtcct gtcgggtttc gccacctctg       5460
acttgagcgt cgattttgt gatgctcgtc aggggggccg agcctatgga aaaacgccag       5520
caacgcggcc ttttacggt tcctggcctt ttgctggcct tttgctcaca tgttctttcc       5580
tgcgttatcc cctgattctg tggataaccg tattaccgcc tttgagtgag ctgataccgc      5640
tcgccgcagc cgaacgaccg agcgcagcga gtcagtgagc gaggaagcgg aagagcgccc     5700
aatacgcaaa ccgcctctcc ccgcgcgttg gccgattcat taatgcagct ggcacgacag      5760
gtttcccgac tggaaagcgg gcagtgagcg caacgcaatt aatgtgagtt acctcactca      5820
ttaggcaccc caggctttac actttatgct tccggctcct atgttgtgtg aattgtgag       5880 cggataacaa tttcacacag gaaacagcta tgaccatgat tacgccaagc tcggaattaa      5940
ccctcactaa agggaacaaa agctggctag t                                    5971
```

<210> SEQ ID NO 17
<211> LENGTH: 5657
<212> TYPE: DNA
<213> ORGANISM: artificial
<220> FEATURE:
<223> OTHER INFORMATION: pYD1CH12

<400> SEQUENCE: 17

```
acggattaga agccgccgag cgggtgacag ccctccgaag gaagactctc ctccgtgcgt        60
cctcgtcttc accggtcgcg ttcctgaaac gcagatgtgc ctcgcgccgc actgctccga       120
acaataaaga ttctacaata ctagctttta tggttatgaa gaggaaaaat tggcagtaac       180
ctggccccac aaaccttcaa atgaacgaat caaattaaca accataggat gataatgcga      240 ttagttttttt agccttattt ctgggtaat taatcagcga agcgatgatt tttgatctat       300
taacagatat ataaatgcaa aaactgcata accactttaa ctaatacttt caacattttc      360
ggtttgtatt acttcttatt caatgtaat aaaagtatca acaaaaaatt gttaatatac       420
ctctatactt taacgtcaag gagaaaaaac cccggatcgg actactagca gctgtaatac      480
gactcactat agggaatatt aagctaattc tacttcatac atttttcaatt aagatgcagt     540 tacttcgctg ttttcaata ttttctgtta ttgcttcagt tttagcacag gaactgacaa       600
ctatatgcga gcaaatcccc tcaccaactt tagaatcgac gccgtactct ttgtcaacga      660
ctactatttt ggccaacggg aaggcaatgc aaggagtttt tgaatattac aaatcagtaa     720
cgtttgtcag taattgcggt tctcaccccct caacaactag caaaggcagc ccataaaca      780 cacagtatgt ttttaagctt ctgcaggcta gtggtggtgg tggttctggt ggtggtggtt     840
ctggtggtgg tggttctgct agcatgactg gtggacagca aatgggtcgg gatctgtacg      900
acgatgacga taaggtacca ggatccgcta gcaccaaggg ccccagcgtg ttccctctgg      960
cccccagctc caagagcacc tccggcggca ccgccgccct gggctgcctg gtgaaggatt    1020
acttcccaga gcccgtgacc gtgagctgga acagcggcgc cctgaccagc ggcgtgcaca     1080 cctttccgc cgtgctgcag tccagcggcc tgtactccct gagcagcgtg gtgaccgtgc     1140
ccagcagcag cctgggcacc cagacctaca tctgcaatgt gaaccacaag cccagcaata     1200
ccaaggtgga taagaaggtg agcccaaga gcagcgacaa gacacacacg tgtcccccat     1260
gtccccgccc tgagctgctg gcggccctt ccgtgttcct gttccctccc aagccaaagg     1320
acaccctgat gatctcccgg acccctgagg tgacctgtgt ggtggtggac gtgagccacg     1380
```

```
aggacccaga ggtgaagttc aactggtacg tggacggcgt ggaggtgcac aacgccaaga   1440
ccaagcctag agaggagcag tacaacagca cctaccgcgt ggtgagcgtg ctgaccgtgc   1500
tgcaccagga ttggctgaat ggcaaggagt acaagtgcaa ggtgagcaac aaggccctgc   1560
ctgcccccat cgagaagacc atctccaagg ccaagggcca gcctcgaggc cgctcgatcg   1620
agtctagagg gcccttcgaa ggtaagccta tccctaaccc tctcctcggt ctcgattcta   1680
cgcgtaccgg tcatcatcac catcaccatt gagtttaaac ccgctgatct gataacaaca   1740
gtgtagatgt aacaaaatcg actttgttcc cactgtactt ttagctcgta caaaatacaa   1800 tatactttc atttctccgt aaacaacatg ttttcccatg taatatcctt ttctattttt    1860
cgttccgtta ccaactttac acatacttta tatagctatt cacttctata cactaaaaaa   1920
ctaagacaat tttaattttg ctgcctgcca tatttcaatt tgttataaat tcctataatt   1980
tatcctatta gtagctaaaa aaagatgaat gtgaatcgaa tcctaagaga attgggcaag   2040
tgcacaaaca atacttaaat aaatactact cagtaataac ctatttctta gcattttga    2100 cgaaatttgc tattttgtta gagtcttta caccattgt ctccacacct ccgcttacat     2160
caacaccaat aacgccattt aatctaagcg catcaccaac attttctggc gtcagtccac   2220
cagctaacat aaaatgtaag ctctcggggc tctcttgcct tccaacccag tcagaaatcg   2280
agttccaatc caaagttca cctgtcccac ctgcttctga atcaaacaag gaataaacg     2340 aatgaggttt ctgtgaagct gcactgagta gtatgttgca gtcttttgga aatacgagtc   2400
ttttaataac tggcaaaccg aggaactctt ggtattcttg ccacgactca tctccgtgca   2460
gttggacgat atcaatgccg taatcattga ccagagccaa acatcctcc ttaggttgat    2520 tacgaaacac gccaaccaag tatttcggag tgcctgaact attttttatat gcttttacaa  2580 gacttgaaat tttccttgca ataaccgggt caattgttct ctttctattg ggcacacata   2640
taatacccag caagtcagca tcggaatcta gagcacattc tgcggcctct gtgctctgca   2700
agccgcaaac tttcaccaat ggaccagaac tacctgtgaa attaataaca gacatactcc   2760
aagctgcctt tgtgtgctta atcacgtata ctcacgtgct caatagtcac caatgccctc   2820
cctcttggcc ctctccttt ctttttcga ccgaatttct tgaagacgaa agggcctcgt     2880
gatacgccta tttttatagg ttaatgtcat gataataatg gtttcttagg acggatcgct   2940
tgcctgtaac ttacacgcgc ctcgtatctt ttaatgatgg aataatttgg gaatttactc   3000
tgtgtttatt tattttatg ttttgtattt ggattttaga aagtaaataa agaaggtaga    3060
agagttacgg aatgaagaaa aaaaaataaa caaaggttta aaaaatttca acaaaaagcg   3120
tactttacat atatatttat tagacaagaa aagcagatta aatagatata cattcgatta   3180
acgataagta aaatgtaaaa tcacaggatt ttcgtgtgtg gtcttctaca cagacaagat   3240
gaaacaattc ggcattaata cctgagagca ggaagagcaa gataaaggt agtatttgtt    3300 ggcgatcccc ctagagtctt ttacatcttc ggaaaacaaa aactattttt tctttaattt   3360 cttttttac tttctattt taattatat atttatatta aaaaatttaa attataatta     3420
tttttatagc acgtgatgaa aaggacccag gtggcacttt tcggggaaat gtgcgcggaa   3480
cccctatttg tttattttc taaatacatt caaatatgta tccgctcatg agacaataac    3540
cctgataaat gcttcaataa tattgaaaaa ggaagagtat gagtattcaa catttccgtg   3600
tcgcccttat tccctttttt gcggcatttt gccttcctgt ttttgctcac ccagaaacgc   3660
tggtgaaagt aaaagatgct gaagatcagt tgggtgcacg agtgggttac atcgaactgg   3720
atctcaacag cggtaagatc cttgagagtt ttcgccccga agaacgtttt ccaatgatga   3780
```

```
gcacttttaa agttctgcta tgtggcgcgg tattatcccg tgttgacgcc gggcaagagc    3840
aactcggtcg ccgcatacac tattctcaga atgacttggt tgagtactca ccagtcacag    3900
aaaagcatct tacggatggc atgacagtaa gagaattatg cagtgctgcc ataaccatga    3960
gtgataacac tgcggccaac ttacttctga caacgatcgg aggaccgaag gagctaaccg    4020
cttttttgca caacatgggg gatcatgtaa ctcgccttga tcgttgggaa ccggagctga    4080
atgaagccat accaaacgac gagcgtgaca ccacgatgcc tgtagcaatg caacaacgt     4140 tgcgcaaact attaactggc gaactactta ctctagcttc ccggcaacaa ttaatagact    4200
ggatggaggc ggataaagtt gcaggaccac ttctgcgctc ggcccttccg gctggctggt    4260
ttattgctga taaatctgga gccggtgagc gtgggtctcg cggtatcatt gcagcactgg    4320
ggccagatgg taagccctcc cgtatcgtag ttatctacac gacgggcagt caggcaacta    4380
tggatgaacg aaatagacag atcgctgaga taggtgcctc actgattaag cattggtaac    4440
tgtcagacca gtttactcat atatacttt  agattgattt aaaacttcat ttttaattta     4500
aaaggatcta ggtgaagatc ctttttgata atctcatgac caaaatccct aacgtgagt     4560 tttcgttcca ctgagcgtca gacccgtag  aaaagatcaa aggatcttct tgagatcctt     4620
tttttctgcg cgtaatctgc tgcttgcaaa caaaaaaacc accgctacca gcggtggttt    4680
gtttgccgga tcaagagcta ccaactcttt tccgaaggt  aactggcttc agcagagcgc     4740
agataccaaa tactgtcctt ctagtgtagc cgtagttagg ccaccacttc aagaactctg    4800
tagcaccgcc tacatacctc gctctgctaa tcctgttacc agtggctgct gccagtggcg    4860
ataagtcgtg tcttaccggg ttggactcaa gacgatagtt accggataag cgcagcggt     4920 cgggctgaac ggggggttcg tgcacacagc ccagcttgga gcgaacgacc tacaccgaac    4980
tgagatacct acagcgtgag cattgagaaa gcgccacgct tcccgaaggg agaaaggcgg    5040
acaggtatcc ggtaagcggc agggtcggaa caggagagcg cacgagggag cttccagggg    5100
ggaacgcctg gtatctttat agtcctgtcg ggtttcgcca cctctgactt gagcgtcgat    5160
ttttgtgatg ctcgtcaggg ggccgagcc  tatggaaaaa cgccagcaac gcggcctttt     5220
tacggttcct ggccttttgc tggccttttg ctcacatgtt ctttcctgcg ttatcccctg    5280
attctgtgga taaccgtatt accgcctttg agtgagctga taccgctcgc cgcagccgaa    5340
cgaccgagcg cagcgagtca gtgagcgagg aagcggaaga gcgcccaata cgcaaaccgc    5400
ctctccccgc gcgttggccg attcattaat gcagctggca cgacaggttt cccgactgga    5460
aagcgggcag tgagcgcaac gcaattaatg tgagttacct cactcattag gcaccccagg    5520
ctttacactt tatgcttccg gctcctatgt tgtgtggaat tgtgagcgga taacaatttc    5580
acacaggaaa cagctatgac catgattacg ccaagctcgg aattaaccct cactaaaggg    5640
aacaaaagct ggctagt                                                   5657
```

<210> SEQ ID NO 18
<211> LENGTH: 738
<212> TYPE: DNA
<213> ORGANISM: artificial
<220> FEATURE:
<223> OTHER INFORMATION: Fcab01
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)

<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t

<400> SEQUENCE: 18

```
ggcccagccg gccatggccg agcccaaatc ttgtgacaaa actcacacat gcccaccgtg      60
cccagcacct gaactcctgg ggggaccgtc agtcttcctc ttccccccaa aacccaagga     120
caccctcatg atctcccgga cccctgaggt cacatgcgtg gtggtggacg tgagccacga     180
agaccctgag gtcaagttca actggtacgt ggacggcgtg gaggtgcata atgccaagac     240
aaagccgcgg gaggagcagt acaacagcac gtaccgtgtg gtcagcgtcc tcaccgtcct     300
gcaccaggac tggctgaatg gcaaggagta caagtgcaag gtctccaaca aagccctccc     360
agcccccatc gagaaaacca tctccaaagc caaagggcag cctcgagaac cacaggtgta     420
caccctgccc ccatcccggg atgaactgnn bnnbnnbcag gtcagcctga cctgcctggt     480
caaaggcttc tatcccagcg acatcgccgt ggagtgggag agcaatgggc agccggagaa     540
caactacaag accacgcctc ccgtgctgga ctccgacggc tccttcttcc tctacagcaa     600
gctcaccgtg nnbnnbnnbn nbnnbnnbnn bnnbaggtgg nnbnnbggga acgtcttctc     660
atgctccgtg atgcatgagg ctctgcacaa ccactacacg cagaagagcc tctccctgtc     720
tccgggtaaa gcggccgc                                                   738
```

<210> SEQ ID NO 19
<211> LENGTH: 738
<212> TYPE: DNA
<213> ORGANISM: artificial

<220> FEATURE:
<223> OTHER INFORMATION: Fcab02

<400> SEQUENCE: 19

```
ggcccagccg gccatggccg agcccaaatc ttgtgacaaa actcacacat gcccaccgtg    60
cccagcacct gaactcctgg ggggaccgtc agtcttcctc ttcccccaa aacccaagga    120
caccctcatg atctcccgga cccctgaggt cacatgcgtg gtggtggacg tgagccacga    180
agaccctgag gtcaagttca actggtacgt ggacggcgtg gaggtgcata atgccaagac    240
aaagccgcgg gaggagcagt acaacagcac gtaccgtgtg gtcagcgtcc tcaccgtcct    300
gcaccaggac tggctgaatg gcaaggagta caagtgcaag gtctccaaca aagccctccc    360
agcccccatc gagaaaacca tctccaaagc caaagggcag cctcgagaac cacaggtgta    420
caccctgccc ccatcccggg atgagctgkm tkmtkmtcag gtgagcctga cctgcctggt    480
caaaggcttc tatcccagcg acatcgccgt ggagtgggag agcaatgggc agccggagaa    540
caactacaag accacgcctc ccgtgctgga ctccgacggc tccttcttcc tctacagcaa    600
gctcaccgtg kmtkmtkmtk mtkmtkmtkm tkmtaggtgg kmtkmtggga acgtcttctc    660
atgctccgtg atgcatgagg ctctgcacaa ccactacacg cagaagagcc tctccctgtc    720
tccgggtaaa gcggccgc                                                 738
```

<210> SEQ ID NO 20
<211> LENGTH: 750
<212> TYPE: DNA
<213> ORGANISM: artificial
<220> FEATURE:
<223> OTHER INFORMATION: Fcab03
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (635)..(636)
<223> OTHER INFORMATION: n is a, c, g, or t
<220> FEATURE:

```
<221> NAME/KEY: misc_feature
<222> LOCATION: (638)..(639)
<223> OTHER INFORMATION: n is a, c, g, or t
<220> FEATURE:
<221> NAME/KEY: misc_feature
<222> LOCATION: (653)..(654)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t

<400> SEQUENCE: 20
ggcccagccg gccatggccg agcccaaatc ttgtgacaaa actcacacat gcccaccgtg    60
cccagcacct gaactcctgg ggggaccgtc agtcttcctc ttccccccaa acccaagga    120 caccctcatg atctcccgga cccctgaggt cacatgcgtg gtggtggacg tgagccacga    180
agaccctgag gtcaagttca actggtacgt ggacggcgtg gaggtgcata atgccaagac    240
aaagccgcgg gaggagcagt acaacagcac gtaccgtgtg gtcagcgtcc tcaccgtcct    300
gcaccaggac tggctgaatg gcaaggagta caagtgcaag gtctccaaca agcccctccc    360
agcccccatc gagaaaacca tctccaaagc caaagggcag cctcgagaac cacaggtgta    420
caccctgccc ccttcccggg atgagctgnn bnnbnnbcag gtcagcctga cctgcctggt    480
caaaggcttc tatcccagcg acatcgccgt ggagtgggag agcaatgggc agccggagaa    540
caactacaag accacgcctc ccgtgctgga ctccgacggc tccttcttcc tctacagcaa    600
gctcaccgtg gttctnnbn nbnnbnnbnn bnnbnnbnnb agcggcaggt ggnnbnnbgg    660
gaacgtcttc tcatgctccg tgatgcatga ggctctgcac aaccactaca cgcagaagag    720
cctctccctg tctccgggta aagcggccgc                                    750

<210> SEQ ID NO 21
<211> LENGTH: 750
<212> TYPE: DNA
<213> ORGANISM: artificial
<220> FEATURE:
<223> OTHER INFORMATION: Fcab04

<400> SEQUENCE: 21
ggcccagccg gccatggccg agcccaaatc ttgtgacaaa actcacacat gcccaccgtg    60
cccagcacct gaactcctgg ggggaccgtc agtcttcctc ttccccccaa acccaagga    120 caccctcatg atctcccgga cccctgaggt cacatgcgtg gtggtggacg tgagccacga    180
agaccctgag gtcaagttca actggtacgt ggacggcgtg gaggtgcata atgccaagac    240
aaagccgcgg gaggagcagt acaacagcac gtaccgtgtg gtcagcgtcc tcaccgtcct    300
gcaccaggac tggctgaatg gcaaggagta caagtgcaag gtctccaaca agcccctccc    360
agcccccatc gagaaaacca tctccaaagc caaagggcag cctcgagaac cacaggtgta    420
caccctgccc ccatctcggg atgagctgkm tkmtkmtcag gtcagcctga cctgcctggt    480
caaaggcttc tatcccagcg acatcgccgt ggagtgggag agcaatgggc agccggagaa    540
caactacaag accacgcctc ccgtgctgga ctccgacggc tccttcttcc tctacagcaa    600
gctcaccgtg ggttctkmtk mtkmtkmtkm tkmtkmtkmt agcggcaggt ggkmtkmtgg    660
gaacgtcttc tcatgctccg tgatgcatga ggctctgcac aaccactaca cgcagaagag    720
cctctccctg tctccgggta aagcggccgc                                    750

<210> SEQ ID NO 22
<211> LENGTH: 738
```

```
<212> TYPE: DNA
<213> ORGANISM: artificial
<220> FEATURE:
<223> OTHER INFORMATION: Fcab05
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t

<400> SEQUENCE: 22
ggcccagccg gccatggccg agcccaaatc ttgtgacaaa actcacacat gcccaccgtg      60
cccagcacct gaactcctgg ggggaccgtc agtcttcctc ttccccccaa aacccaagga     120
caccctcatg atctcccgga cccctgaggt cacatgcgtg gtggtggacg tgagccacga     180
agaccctgag gtcaagttca actggtacgt ggacggcgtg gaggtgcata atgccaagac     240
aaagccgcgg gaggagcagt acaacagcac gtaccgtgtg gtcagcgtcc tcaccgtcct     300
gcaccaggac tggctgaatg gcaaggagta caagtgcaag gtctccaaca aagcccttccc    360 agcccccatc gagaaaacca tctccaaagc caaagggcag cctcgagaac cacaggtgta     420
caccctgccc ccatcccgtg atgagkmtnn bnnbnnbkmt gtcagcctga cctgcctggt     480
caaaggcttc tatcccagcg acatcgccgt ggagtgggag agcaatgggc agccggagaa     540
caactacaag accacgcctc ccgtgctgga ctccgacggc tccttcttcc tctacagcaa     600
```

```
gctcaccgtg nnbnnbnnbn nbnnbnnbnn bnnbaggtgg nnbnnbggga acgtcttctc    660
atgctccgtg atgcatgagg ctctgcacaa ccactacacg cagaagagcc tctccctgtc    720
tccgggtaaa gcggccgc                                                  738
```

```
<210> SEQ ID NO 23
<211> LENGTH: 738
<212> TYPE: DNA
<213> ORGANISM: artificial
<220> FEATURE:
<223> OTHER INFORMATION: Fcab06

<400> SEQUENCE: 23
```

```
ggcccagccg gccatggccg agcccaaatc ttgtgacaaa actcacacat gcccaccgtg     60
cccagcacct gaactcctgg ggggaccgtc agtcttcctc ttccccccaa aacccaagga    120
caccctcatg atctcccgga cccctgaggt cacatgcgtg gtggtggacg tgagccacga    180
agaccctgag gtcaagttca actggtacgt ggacggcgtg gaggtgcata atgccaagac    240
aaagccgcgg gaggagcagt acaacagcac gtaccgtgtg gtcagcgtcc tcaccgtcct    300
gcaccaggac tggctgaatg gcaaggagta caagtgcaag gtctccaaca aagcccctcc    360
agcccccatc gagaaaacca tctccaaagc caaagggcag cctcgagaac acaggtgta    420 cacccctgccc ccatcccggg acgagkmtkm tkmtkmtkmt gtcagcctga cctgcctggt    480
caaaggcttc tatcccagcg acatcgccgt ggagtgggag agcaatgggc agccggagaa    540
caactacaag accacgcctc ccgtgctgga ctccgacggc tccttcttcc tctacagcaa    600
gctcaccgtg kmtkmtkmtk mtkmtkmtkm tkmtaggtgg kmtkmtggga acgtcttctc    660
atgctccgtg atgcatgagg ctctgcacaa ccactacacg cagaagagcc tctccctgtc    720
tccgggtaaa gcggccgc                                                  738
```

```
<210> SEQ ID NO 24
<211> LENGTH: 85
<212> TYPE: DNA
<213> ORGANISM: artificial
<220> FEATURE:
<223> OTHER INFORMATION: PCR primer gapch35

<400> SEQUENCE: 24
```

```
caacaaggcc ctgcctgccc ccatcgagaa gaccatctcc aaggccaagg gccagcctcg     60
agaaccacag gtgtacaccc tgccc                                           85
```

```
<210> SEQ ID NO 25
<211> LENGTH: 99
<212> TYPE: DNA
<213> ORGANISM: artificial
<220> FEATURE:
<223> OTHER INFORMATION: PCR primer gapfcs3

<400> SEQUENCE: 25
```

```
gagaccgagg agagggttag ggataggctt accttcgaag ggccctctag actcgatcga     60
gcggccgctc atttacccgg agacaggag aggctcttc                              99
```

```
<210> SEQ ID NO 26
<211> LENGTH: 79
<212> TYPE: DNA
<213> ORGANISM: artificial
<220> FEATURE:
<223> OTHER INFORMATION: primer Abmut
<220> FEATURE:
<221> NAME/KEY: misc_feature
```

```
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 26
gaaccacagg tgtacaccct gcccccatcc cgggatgagc tgnnbnnbnn bcaggtcagc      60
ctgacctgcc tggtcaaag                                                  79

<210> SEQ ID NO 27
<211> LENGTH: 79
<212> TYPE: DNA
<213> ORGANISM: artificial
<220> FEATURE:
<223> OTHER INFORMATION: primer Abmut2LR
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 27
gaaccacagg tgtacaccct gcccccatcc cgggatgagn nbnnbnnbnn bnnbgtcagc      60
ctgacctgcc tggtcaaag                                                  79

<210> SEQ ID NO 28
<211> LENGTH: 79
<212> TYPE: DNA
<213> ORGANISM: artificial
<220> FEATURE:
<223> OTHER INFORMATION: primer Abmut1L
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 28
gaaccacagg tgtacaccct gcccccatcc cgggatgagn nbnnbnnbnn bcaggtcagc      60
```
ctgacctgcc tggtcaaag                                                    79

```
<210> SEQ ID NO 29
<211> LENGTH: 79
<212> TYPE: DNA
<213> ORGANISM: artificial
<220> FEATURE:
<223> OTHER INFORMATION: primer Abmut1R
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 29
```
gaaccacagg tgtacaccct gcccccatcc cgggatgagc tgnnbnnbnn bnnbgtcagc       60
ctgacctgcc tggtcaaag                                                    79

```
<210> SEQ ID NO 30
<211> LENGTH: 5
<212> TYPE: PRT
<213> ORGANISM: artificial
<220> FEATURE:
<223> OTHER INFORMATION: AB-loop sequence AA143ff

<400> SEQUENCE: 30
```

Leu Asp Asn Ser Gln
1               5

```
<210> SEQ ID NO 31
<211> LENGTH: 5
<212> TYPE: PRT
<213> ORGANISM: artificial
<220> FEATURE:
<223> OTHER INFORMATION: AB-loop sequence AA143ff

<400> SEQUENCE: 31
```

Tyr Glu Gly Ser Ser
1               5

```
<210> SEQ ID NO 32
<211> LENGTH: 5
<212> TYPE: PRT
<213> ORGANISM: artificial
<220> FEATURE:
<223> OTHER INFORMATION: AB-loop sequence AA143ff

<400> SEQUENCE: 32
```

Tyr Met Ser Ala Asp
1               5

```
<210> SEQ ID NO 33
<211> LENGTH: 5
<212> TYPE: PRT
<213> ORGANISM: artificial
<220> FEATURE:
<223> OTHER INFORMATION: AB-loop sequence AA143ff
```

```
<400> SEQUENCE: 33

Tyr Arg Arg Gly Asp
1               5

<210> SEQ ID NO 34
<211> LENGTH: 5
<212> TYPE: PRT
<213> ORGANISM: artificial
<220> FEATURE:
<223> OTHER INFORMATION: AB-loop sequence AA143ff

<400> SEQUENCE: 34

Leu Met Ser Arg Gln
1               5

<210> SEQ ID NO 35
<211> LENGTH: 5
<212> TYPE: PRT
<213> ORGANISM: artificial
<220> FEATURE:
<223> OTHER INFORMATION: AB-loop sequence AA143ff

<400> SEQUENCE: 35

Leu His Leu Ala Gln
1               5

<210> SEQ ID NO 36
<211> LENGTH: 5
<212> TYPE: PRT
<213> ORGANISM: artificial
<220> FEATURE:
<223> OTHER INFORMATION: AB-loop sequence AA143ff

<400> SEQUENCE: 36

Tyr Leu Ser Lys Asp
1               5

<210> SEQ ID NO 37
<211> LENGTH: 5
<212> TYPE: PRT
<213> ORGANISM: artificial
<220> FEATURE:
<223> OTHER INFORMATION: AB-loop sequence AA143ff

<400> SEQUENCE: 37

Tyr Arg Ser Gly Ser
1               5

<210> SEQ ID NO 38
<211> LENGTH: 5
<212> TYPE: PRT
<213> ORGANISM: artificial
<220> FEATURE:
<223> OTHER INFORMATION: AB-loop sequence AA143ff

<400> SEQUENCE: 38

Leu Arg Asp Gly Gln
1               5

<210> SEQ ID NO 39
<211> LENGTH: 5
<212> TYPE: PRT
<213> ORGANISM: artificial
<220> FEATURE:
<223> OTHER INFORMATION: AB-loop sequence AA143ff

<400> SEQUENCE: 39
```

```
Tyr Ser Ala Asn Thr
1               5

<210> SEQ ID NO 40
<211> LENGTH: 5
<212> TYPE: PRT
<213> ORGANISM: artificial
<220> FEATURE:
<223> OTHER INFORMATION: AB-loop sequence AA143ff

<400> SEQUENCE: 40

Tyr Ala Ser Asn Thr
1               5

<210> SEQ ID NO 41
<211> LENGTH: 5
<212> TYPE: PRT
<213> ORGANISM: artificial
<220> FEATURE:
<223> OTHER INFORMATION: AB-loop sequence AA143ff

<400> SEQUENCE: 41

Tyr Ser Asp Gly Asp
1               5

<210> SEQ ID NO 42
<211> LENGTH: 5
<212> TYPE: PRT
<213> ORGANISM: artificial
<220> FEATURE:
<223> OTHER INFORMATION: AB-loop sequence AA143ff

<400> SEQUENCE: 42

Tyr Ser Gly Gly Ser
1               5

<210> SEQ ID NO 43
<211> LENGTH: 5
<212> TYPE: PRT
<213> ORGANISM: artificial
<220> FEATURE:
<223> OTHER INFORMATION: AB-loop sequence AA143ff

<400> SEQUENCE: 43

Tyr Gly Arg Asp Ser
1               5

<210> SEQ ID NO 44
<211> LENGTH: 5
<212> TYPE: PRT
<213> ORGANISM: artificial
<220> FEATURE:
<223> OTHER INFORMATION: AB-loop sequence AA143ff

<400> SEQUENCE: 44

Tyr Ala Gly Gly Thr
1               5

<210> SEQ ID NO 45
<211> LENGTH: 5
<212> TYPE: PRT
<213> ORGANISM: artificial
<220> FEATURE:
<223> OTHER INFORMATION: AB-loop sequence AA143ff

<400> SEQUENCE: 45
```

```
Tyr Ser Ser Asp Ser
1               5

<210> SEQ ID NO 46
<211> LENGTH: 5
<212> TYPE: PRT
<213> ORGANISM: artificial
<220> FEATURE:
<223> OTHER INFORMATION: AB-loop sequence AA143ff

<400> SEQUENCE: 46

Tyr His Ser Gly Ser
1               5

<210> SEQ ID NO 47
<211> LENGTH: 5
<212> TYPE: PRT
<213> ORGANISM: artificial
<220> FEATURE:
<223> OTHER INFORMATION: AB-loop sequence AA143ff

<400> SEQUENCE: 47

Tyr Leu Thr Asn Ser
1               5

<210> SEQ ID NO 48
<211> LENGTH: 5
<212> TYPE: PRT
<213> ORGANISM: artificial
<220> FEATURE:
<223> OTHER INFORMATION: AB-loop sequence AA143ff

<400> SEQUENCE: 48

Tyr Gly Ser Glu Glu
1               5

<210> SEQ ID NO 49
<211> LENGTH: 5
<212> TYPE: PRT
<213> ORGANISM: artificial
<220> FEATURE:
<223> OTHER INFORMATION: AB-loop sequence AA143ff

<400> SEQUENCE: 49

Tyr Arg Ser Gly Glu
1               5

<210> SEQ ID NO 50
<211> LENGTH: 5
<212> TYPE: PRT
<213> ORGANISM: artificial
<220> FEATURE:
<223> OTHER INFORMATION: AB-loop sequence AA143ff

<400> SEQUENCE: 50

Tyr Gly Thr Asp Asp
1               5

<210> SEQ ID NO 51
<211> LENGTH: 12
<212> TYPE: PRT
<213> ORGANISM: artificial
<220> FEATURE:
<223> OTHER INFORMATION: EF-loop sequence AA198ff

<400> SEQUENCE: 51

Ile Arg Ser Ser Val Gly Ser Arg Arg Trp Trp Ser
```

```
<210> SEQ ID NO 52
<211> LENGTH: 12
<212> TYPE: PRT
<213> ORGANISM: artificial
<220> FEATURE:
<223> OTHER INFORMATION: EF-loop sequence AA198ff

<400> SEQUENCE: 52

Ala Arg Tyr Ser Pro Arg Met Leu Arg Trp Ala His
1               5                   10

<210> SEQ ID NO 53
<211> LENGTH: 12
<212> TYPE: PRT
<213> ORGANISM: artificial
<220> FEATURE:
<223> OTHER INFORMATION: EF-loop sequence AA198ff

<400> SEQUENCE: 53

Ser Arg Arg Asp Ser Ser Leu Leu Arg Trp Ala His
1               5                   10

<210> SEQ ID NO 54
<211> LENGTH: 12
<212> TYPE: PRT
<213> ORGANISM: artificial
<220> FEATURE:
<223> OTHER INFORMATION: EF-loop sequence AA198ff

<400> SEQUENCE: 54

Ala Pro Gly Ser Lys Gly Tyr Arg Arg Trp Ala Leu
1               5                   10

<210> SEQ ID NO 55
<211> LENGTH: 12
<212> TYPE: PRT
<213> ORGANISM: artificial
<220> FEATURE:
<223> OTHER INFORMATION: EF-loop sequence AA198ff

<400> SEQUENCE: 55

Asp Lys Pro Phe Trp Gly Thr Ser Arg Trp Ser Arg
1               5                   10

<210> SEQ ID NO 56
<211> LENGTH: 12
<212> TYPE: PRT
<213> ORGANISM: artificial
<220> FEATURE:
<223> OTHER INFORMATION: EF-loop sequence AA198ff

<400> SEQUENCE: 56

Ser Ile Asn Asp Leu Ile Asn His Arg Trp Pro Tyr
1               5                   10

<210> SEQ ID NO 57
<211> LENGTH: 12
<212> TYPE: PRT
<213> ORGANISM: artificial
<220> FEATURE:
<223> OTHER INFORMATION: EF-loop sequence AA198ff

<400> SEQUENCE: 57

Met Trp Gly Ser Arg Asp Tyr Trp Arg Trp Ser His
1               5                   10
```

```
<210> SEQ ID NO 58
<211> LENGTH: 12
<212> TYPE: PRT
<213> ORGANISM: artificial
<220> FEATURE:
<223> OTHER INFORMATION: EF-loop sequence AA198ff

<400> SEQUENCE: 58

Asn Ser Gly Ser Ala Met Met Val Arg Trp Ala His
1               5                   10

<210> SEQ ID NO 59
<211> LENGTH: 12
<212> TYPE: PRT
<213> ORGANISM: artificial
<220> FEATURE:
<223> OTHER INFORMATION: EF-loop sequence AA198ff

<400> SEQUENCE: 59

Gln Arg Ser Arg Leu Ser Arg Gln Arg Trp Trp Arg
1               5                   10

<210> SEQ ID NO 60
<211> LENGTH: 12
<212> TYPE: PRT
<213> ORGANISM: artificial
<220> FEATURE:
<223> OTHER INFORMATION: EF-loop sequence AA198ff

<400> SEQUENCE: 60

Ala Arg Tyr Ser Pro Arg Met Leu Arg Trp Ala His
1               5                   10

<210> SEQ ID NO 61
<211> LENGTH: 12
<212> TYPE: PRT
<213> ORGANISM: artificial
<220> FEATURE:
<223> OTHER INFORMATION: EF-loop sequence AA198ff

<400> SEQUENCE: 61

Ala Arg Tyr Ser Pro Arg Met Leu Arg Trp Ala His
1               5                   10

<210> SEQ ID NO 62
<211> LENGTH: 12
<212> TYPE: PRT
<213> ORGANISM: artificial
<220> FEATURE:
<223> OTHER INFORMATION: EF-loop sequence AA198ff

<400> SEQUENCE: 62

Ala Arg Tyr Ser Pro Arg Met Leu Arg Trp Ala His
1               5                   10

<210> SEQ ID NO 63
<211> LENGTH: 12
<212> TYPE: PRT
<213> ORGANISM: artificial
<220> FEATURE:
<223> OTHER INFORMATION: EF-loop sequence AA198ff

<400> SEQUENCE: 63

Ala Arg Tyr Ser Pro Arg Met Leu Arg Trp Ala His
1               5                   10
```

<210> SEQ ID NO 64
<211> LENGTH: 12
<212> TYPE: PRT
<213> ORGANISM: artificial
<220> FEATURE:
<223> OTHER INFORMATION: EF-loop sequence AA198ff

<400> SEQUENCE: 64

Ala Arg Tyr Ser Pro Arg Met Leu Arg Trp Ala His
1               5                   10

<210> SEQ ID NO 65
<211> LENGTH: 12
<212> TYPE: PRT
<213> ORGANISM: artificial
<220> FEATURE:
<223> OTHER INFORMATION: EF-loop sequence AA198ff

<400> SEQUENCE: 65

Ala Arg Tyr Ser Pro Arg Met Leu Arg Trp Ala His
1               5                   10

<210> SEQ ID NO 66
<211> LENGTH: 12
<212> TYPE: PRT
<213> ORGANISM: artificial
<220> FEATURE:
<223> OTHER INFORMATION: EF-loop sequence AA198ff

<400> SEQUENCE: 66

Ala Arg Tyr Ser Pro Arg Met Leu Arg Trp Ala His
1               5                   10

<210> SEQ ID NO 67
<211> LENGTH: 12
<212> TYPE: PRT
<213> ORGANISM: artificial
<220> FEATURE:
<223> OTHER INFORMATION: EF-loop sequence AA198ff

<400> SEQUENCE: 67

Ala Arg Tyr Ser Pro Arg Met Leu Arg Trp Ala His
1               5                   10

<210> SEQ ID NO 68
<211> LENGTH: 12
<212> TYPE: PRT
<213> ORGANISM: artificial
<220> FEATURE:
<223> OTHER INFORMATION: EF-loop sequence AA198ff

<400> SEQUENCE: 68

Ala Arg Tyr Ser Pro Arg Met Leu Arg Trp Ala His
1               5                   10

<210> SEQ ID NO 69
<211> LENGTH: 12
<212> TYPE: PRT
<213> ORGANISM: artificial
<220> FEATURE:
<223> OTHER INFORMATION: EF-loop sequence AA198ff

<400> SEQUENCE: 69

Ala Arg Tyr Ser Pro Arg Met Leu Arg Trp Ala His
1               5                   10

-continued

<210> SEQ ID NO 70
<211> LENGTH: 12
<212> TYPE: PRT
<213> ORGANISM: artificial
<220> FEATURE:
<223> OTHER INFORMATION: EF-loop sequence AA198ff

<400> SEQUENCE: 70

Ala Arg Tyr Ser Pro Arg Met Leu Arg Trp Ala His
1               5                   10

<210> SEQ ID NO 71
<211> LENGTH: 12
<212> TYPE: PRT
<213> ORGANISM: artificial
<220> FEATURE:
<223> OTHER INFORMATION: EF-loop sequence AA198ff

<400> SEQUENCE: 71

Ala Arg Tyr Ser Pro Arg Met Leu Arg Trp Ala His
1               5                   10

<210> SEQ ID NO 72
<211> LENGTH: 5009
<212> TYPE: DNA
<213> ORGANISM: artificial
<220> FEATURE:
<223> OTHER INFORMATION: vector pYD1

<400> SEQUENCE: 72

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgcttcagt tttagcacag gaactgacaa     600
ctatatgcga gcaaatcccc tcaccaactt tagaatcgac gccgtactct tgtcaacga      660
ctactatttt ggccaacggg aaggcaatgc aaggagtttt tgaatattac aaatcagtaa     720
cgtttgtcag taattgcggt tctcacccct aacaactag caaaggcagc cccataaaca      780
cacagtatgt ttttaagctt ctgcaggcta gtggtggtgg tggttctggt ggtggtggtt     840
ctggtggtgg tggttctgct agcatgactg gtggacagca atgggtcgg atctgtacg      900
acgatgacga taaggtacca ggatccagtg tggtggaatt ctgcagatat ccagcacagt     960
ggcggccgct cgagtctaga gggcccttcg aaggtaagcc tatccctaac cctctcctcg    1020
gtctcgattc tacgcgtacc ggtcatcatc accatcacca ttgagtttaa acccgctgat    1080
ctgataacaa cagtgtagat gtaacaaaat cgactttgtt cccactgtac ttttagctcg    1140
tacaaaatac aatatacttt tcatttctcc gtaaacaaca tgttttccca tgtaatatcc    1200
ttttctattt tcgttccgt taccaacttt acacatactt tatatagcta ttcacttcta    1260
tacactaaaa aactaagaca attttaattt tgctgcctgc catatttcaa tttgttataa    1320
```

```
attcctataa tttatcctat tagtagctaa aaaaagatga atgtgaatcg aatcctaaga   1380
gaattgggca agtgcacaaa caatacttaa ataaatacta ctcagtaata acctatttct   1440
tagcattttt gacgaaattt gctattttgt tagagtcttt tacaccattt gtctccacac   1500
ctccgcttac atcaacacca ataacgccat ttaatctaag cgcatcacca acattttctg   1560
gcgtcagtcc accagctaac ataaaatgta agctctcggg gctctcttgc cttccaaccc   1620
agtcagaaat cgagttccaa tccaaaagtt cacctgtccc acctgcttct gaatcaaaca   1680
agggaataaa cgaatgaggt ttctgtgaag ctgcactgag tagtatgttg cagtcttttg   1740
gaaatacgag tcttttaata actggcaaac cgaggaactc ttggtattct tgccacgact   1800
catctccgtg cagttggacg atatcaatgc cgtaatcatt gaccagagcc aaaacatcct   1860
ccttaggttg attacgaaac acgccaacca agtatttcgg agtgcctgaa ctattttat   1920
atgcttttac aagacttgaa attttccttg caataaccgg gtcaattgtt ctctttctat   1980
tgggcacaca tataataccc agcaagtcag catcggaatc tagagcacat tctgcggcct   2040
ctgtgctctg caagccgcaa actttcacca atggaccaga actacctgtg aaattaataa   2100
cagacatact ccaagctgcc tttgtgtgct taatcacgta tactcacgtg ctcaatagtc   2160
accaatgccc tccctcttgg ccctctcctt ttcttttttc gaccgaattt cttgaagacg   2220
aaagggcctc gtgatacgcc tattttata ggttaatgtc atgataataa tggtttctta   2280
ggacggatcg cttgcctgta acttacacgc gcctcgtatc ttttaatgat ggaataattt   2340
gggaatttac tctgtgttta tttatttta tgttttgtat ttggatttta gaaagtaaat   2400
aaagaaggta gaagagttac ggaatgaaga aaaaaaaata aacaaggtt taaaaaattt   2460
caacaaaaag cgtactttac atatatattt attagacaag aaaagcagat taaatagata   2520
tacattcgat taacgataag taaaatgtaa aatcacagga ttttcgtgtg tggtcttcta   2580
cacagacaag atgaaacaat tcggcattaa tacctgagag caggaagagc aagataaaag   2640
gtagtatttg ttggcgatcc ccctagagtc ttttacatct tcggaaaaca aaaactattt   2700
tttctttaat ttctttttt actttctatt tttaatttat atatttatat taaaaaattt   2760
aaattataat tattttttata gcacgtgatg aaaaggaccc aggtggcact ttcggggaa   2820
atgtgcgcgg aacccctatt tgtttattt tctaaataca ttcaaatatg tatccgctca   2880
tgagacaata accctgataa atgcttcaat aatattgaaa aaggaagagt atgagtattc   2940
aacatttccg tgtcgccctt attcctttt ttgcggcatt ttgccttcct gttttgctc   3000
acccagaaac gctggtgaaa gtaaaagatg ctgaagatca gttgggtgca cgagtgggtt   3060
acatcgaact ggatctcaac agcggtaaga tccttgagag ttttcgcccc gaagaacgtt   3120
ttccaatgat gagcactttt aaagttctgc tatgtggcgc ggtattatcc cgtgttgacg   3180
ccgggcaaga gcaactcggt cgccgcatac actattctca gaatgacttg gttgagtact   3240
caccagtcac agaaaagcat cttacggatg gcatgacagt aagagaatta tgcagtgctg   3300
ccataaccat gagtgataac actgcggcca acttacttct gacaacgatc ggaggaccga   3360
aggagctaac cgcttttttg cacaacatgg gggatcatgt aactcgcctt gatcgttggg   3420
aaccggagct gaatgaagcc ataccaaacg acgagcgtga caccacgatg cctgtagcaa   3480
tggcaacaac gttgcgcaaa ctattaactg gcgaactact tactctagct tcccggcaac   3540
aattaataga ctggatggag gcggataaag ttgcaggacc acttctgcgc tcggcccttc   3600
cggctggctg gtttattgct gataaatctg gagccggtga gcgtgggtct cgcggtatca   3660
ttgcagcact ggggccagat ggtaagccct cccgtatcgt agttatctac acgacgggca   3720
```

```
gtcaggcaac tatggatgaa cgaaatagac agatcgctga gataggtgcc tcactgatta      3780
agcattggta actgtcagac caagtttact catatatact ttagattgat ttaaaacttc      3840
atttttaatt taaaaggatc taggtgaaga tccttttttga taatctcatg accaaaatcc     3900
cttaacgtga gttttcgttc cactgagcgt cagaccccgt agaaaagatc aaaggatctt      3960
cttgagatcc ttttttttctg cgcgtaatct gctgcttgca acaaaaaaaa ccaccgctac     4020
cagcggtggt ttgtttgccg gatcaagagc taccaactct ttttccgaag gtaactggct      4080
tcagcagagc gcagatacca aatactgtcc ttctagtgta gccgtagtta ggccaccact      4140
tcaagaactc tgtagcaccg cctacatacc tcgctctgct aatcctgtta ccagtggctg      4200
ctgccagtgg cgataagtcg tgtcttaccg ggttggactc aagacgatag ttaccggata      4260
aggcgcagcg gtcgggctga acggggggtt cgtgcacaca gcccagcttg gagcgaacga      4320
cctacaccga actgagatac ctacagcgtg agcattgaga aagcgccacg cttcccgaag      4380
ggagaaaggc ggacaggtat ccggtaagcg gcagggtcgg aacaggagag cgcacgaggg      4440
agcttccagg ggggaacgcc tggtatcttt atagtcctgt cgggtttcgc cacctctgac      4500
ttgagcgtcg atttttgtga tgctcgtcag ggggcgcgag cctatggaaa aacgccagca      4560
acgcggcctt tttacggttc ctggccttt gctggccttt tgctcacatg ttctttcctg       4620
cgttatcccc tgattctgtg gataaccgta ttaccgcctt tgagtgagct gataccgctc      4680
gccgcagccg aacgaccgag cgcagcgagt cagtgagcga ggaagcggaa gagcgcccaa      4740
tacgcaaacc gcctctcccc gcgcgttggc cgattcatta atgcagctgg cacgacaggt      4800
ttcccgactg gaaagcgggc agtgagcgca acgcaattaa tgtgagttac ctcactcatt      4860
aggcacccca ggctttacac tttatgcttc cggctcctat gttgtgtgga attgtgagcg      4920
gataacaatt tcacacagga aacagctatg accatgatta cgccaagctc ggaattaacc      4980
ctcactaaag ggaacaaaag ctggctagt                                        5009
```

<210> SEQ ID NO 73
<211> LENGTH: 5009
<212> TYPE: DNA
<213> ORGANISM: artificial
<220> FEATURE:
<223> OTHER INFORMATION: modified vector pYD1Nhe

<400> SEQUENCE: 73

```
acggattaga agccgccgag cgggtgacag ccctccgaag gaagactctc ctccgtgcgt        60
cctcgtcttc accggtcgcg ttcctgaaac gcagatgtgc ctcgcgccgc actgctccga       120
acaataaaga ttctacaata ctagctttta tggttatgaa gaggaaaaat tggcagtaac       180
ctggccccac aaaccttcaa atgaacgaat caaattaaca accataggat gataatgcga      240
ttagtttttt agccttattt ctggggtaat taatcagcga agcgatgatt tttgatctat       300
taacagatat ataaatgcaa aaactgcata accactttaa ctaatacttt caacattttc      360
ggtttgtatt acttcttatt caaatgtaat aaaagtatca acaaaaaatt gttaatatac      420
ctctatactt taacgtcaag gagaaaaaac cccggatcgg actactagca gctgtaatac      480
gactcactat agggaatatt aagctaattc tacttcatac attttcaatt aagatgcagt      540
tacttcgctg ttttttcaata ttttctgtta ttgcttcagt gctagcacag gaactgacaa      600
ctatatgcga gcaaatcccc tcaccaactt tagaatcgac gccgtactct ttgtcaacga      660
ctactatttt ggccaacggg aaggcaatgc aaggagtttt tgaatattac aaatcagtaa      720
```

```
cgtttgtcag taattgcggt tctcacccct caacaactag caaaggcagc cccataaaca    780
cacagtatgt ttttaagctt ctgcaggcta gtggtggtgg tggttctggt ggtggtggtt    840
ctggtggtgg tggttctgct agcatgactg gtggacagca aatgggtcgg gatctgtacg    900
acgatgacga taaggtacca ggatccagtg tggtggaatt ctgcagatat ccagcacagt    960
ggcggccgct cgagtctaga gggcccttcg aaggtaagcc tatccctaac cctctcctcg   1020
gtctcgattc tacgcgtacc ggtcatcatc accatcacca ttgagtttaa acccgctgat   1080
ctgataacaa cagtgtagat gtaacaaaat cgactttgtt cccactgtac ttttagctcg   1140
tacaaaatac aatatacttt tcatttctcc gtaaacaaca tgttttccca tgtaatatcc   1200
ttttctattt ttcgttccgt taccaacttt acacatactt tatatagcta ttcacttcta   1260
tacactaaaa aactaagaca atttttaattt tgctgcctgc catatttcaa tttgttataa   1320
attcctataa tttatcctat tagtagctaa aaaaagatga atgtgaatcg aatcctaaga   1380
gaattgggca agtgcacaaa caatacttaa ataaatacta ctcagtaata acctatttct   1440
tagcattttt gacgaaattt gctattttgt tagagtcttt tacaccattt gtctccacac   1500
ctccgcttac atcaacacca ataacgccat ttaatctaag cgcatcacca acattttctg   1560
gcgtcagtcc accagctaac ataaaatgta agctctcggg gctctcttgc cttccaaccc   1620
agtcagaaat cgagttccaa tccaaaagtt cacctgtccc acctgcttct gaatcaaaca   1680
agggaataaa cgaatgaggt ttctgtgaag ctgcactgag tagtatgttg cagtcttttg   1740
gaaatacgag tcttttaata actggcaaac cgaggaactc ttggtattct tgccacgact   1800
catctccgtg cagttggacg atatcaatgc cgtaatcatt gaccagagcc aaaacatcct   1860
ccttaggttg attacgaaac acgccaacca agtatttcgg agtgcctgaa ctatttttat   1920
atgcttttac aagacttgaa attttccttg caataaccgg gtcaattgtt ctctttctat   1980
tgggcacaca tataataccc agcaagtcag catcggaatc tagagcacat tctgcggcct   2040
ctgtgctctg caagccgcaa actttcacca atggaccaga actacctgtg aaattaataa   2100
cagacatact ccaagctgcc tttgtgtgct taatcacgta tactcacgtg ctcaatagtc   2160
accaatgccc tccctcttgg ccctctcctt ttcttttttc gaccgaattt cttgaagacg   2220
aaagggcctc gtgatacgcc tatttttata ggttaatgtc atgataataa tggtttctta   2280
ggacggatcg cttgcctgta acttacacgc gcctcgtatc ttttaatgat ggaataattt   2340
gggaatttac tctgtgttta tttatttta tgttttgtat ttggatttta gaaagtaaat   2400
aaagaaggta gaagagttac ggaatgaaga aaaaaaata aacaaggtt taaaaaattt   2460 caacaaaaag cgtactttac atatatattt attagacaag aaaagcagat taaatagata   2520
tacattcgat taacgataag taaaatgtaa aatcacagga ttttcgtgtg tggtcttcta   2580
cacagacaag atgaaacaat tcggcattaa tacctgagag caggaagagc aagataaaag   2640
gtagtatttg ttggcgatcc ccctagagtc ttttacatct tcggaaaaca aaaactattt   2700
tttctttaat ttctttttt actttctatt tttaatttat atatttatat taaaaaattt   2760
aaattataat tattttttata gcacgtgatg aaaaggaccc aggtggcact tttcggggaa   2820
atgtgcgcgg aaccctatt tgtttatttt tctaaataca ttcaaatatg tatccgctca   2880
tgagacaata accctgataa atgcttcaat aatattgaaa aggaagagt atgagtattc   2940 aacatttccg tgtcgccctt attcctttt ttgcggcatt ttgccttcct gtttttgctc   3000
acccagaaac gctggtgaaa gtaaaagatg ctgaagatca gttgggtgca cgagtgggtt   3060
acatcgaact ggatctcaac agcggtaaga tccttgagag ttttcgcccc gaagaacgtt   3120
```

```
ttccaatgat gagcactttt aaagttctgc tatgtggcgc ggtattatcc cgtgttgacg    3180
ccgggcaaga gcaactcggt cgccgcatac actattctca gaatgacttg gttgagtact    3240
caccagtcac agaaaagcat cttacggatg gcatgacagt aagagaatta tgcagtgctg    3300
ccataaccat gagtgataac actgcggcca acttacttct gacaacgatc ggaggaccga    3360
aggagctaac cgcttttttg cacaacatgg gggatcatgt aactcgcctt gatcgttggg    3420
aaccggagct gaatgaagcc ataccaaacg acgagcgtga caccacgatg cctgtagcaa    3480
tggcaacaac gttgcgcaaa ctattaactg gcgaactact tactctagct tcccggcaac    3540
aattaataga ctggatggag gcggataaag ttgcaggacc acttctgcgc tcggcccttc    3600
cggctggctg gtttattgct gataaatctg gagccggtga gcgtgggtct cgcggtatca    3660
ttgcagcact ggggccagat ggtaagccct cccgtatcgt agttatctac acgacgggca    3720
gtcaggcaac tatggatgaa cgaaatagac agatcgctga taggtgcc tcactgatta    3780 agcattggta actgtcagac caagtttact catatatact ttagattgat ttaaaacttc    3840 attttttaatt taaaaggatc taggtgaaga tcctttttga taatctcatg accaaaatcc    3900
cttaacgtga gttttcgttc cactgagcgt cagaccccgt agaaaagatc aaaggatctt    3960
cttgagatcc ttttttttctg cgcgtaatct gctgcttgca acaaaaaaa ccaccgctac    4020 cagcggtggt ttgtttgccg gatcaagagc taccaactct ttttccgaag gtaactggct    4080
tcagcagagc gcagatacca aatactgtcc ttctagtgta gccgtagtta ggccaccact    4140
tcaagaactc tgtagcaccg cctacatacc tcgctctgct aatcctgtta ccagtggctg    4200
ctgccagtgg cgataagtcg tgtcttaccg ggttggactc aagacgatag ttaccggata    4260
aggcgcagcg gtcgggctga acggggggtt cgtgcacaca gcccagcttg gagcgaacga    4320
cctacaccga actgagatac ctacagcgtg agcattgaga aagcgccacg cttcccgaag    4380
ggagaaaggc ggacaggtat ccggtaagcg cagggtcgg aacaggagag cgcacgaggg    4440
agcttccagg ggggaacgcc tggtatcttt atagtcctgt cgggtttcgc cacctctgac    4500
ttgagcgtcg atttttgtga tgctcgtcag gggggccgag cctatggaaa aacgccagca    4560
acgcggcctt tttacggttc ctggcctttt gctggccttt tgctcacatg ttctttcctg    4620
cgttatcccc tgattctgtg gataaccgta ttaccgcctt tgagtgagct gataccgctc    4680
gccgcagccg aacgaccgag cgcagcgagt cagtgagcga ggaagcggaa gagcgcccaa    4740
tacgcaaacc gcctctcccc gcgcgttggc cgattcatta atgcagctgg cacgacaggt    4800
ttcccgactg gaaagcgggc agtgagcgca acgcaattaa tgtgagttac ctcactcatt    4860 aggcaccca ggctttacac tttatgcttc cggctcctat gttgtgtgga attgtgagcg    4920
gataacaatt tcacacagga aacagctatg accatgatta cgccaagctc ggaattaacc    4980
ctcactaaag ggaacaaaag ctggctagt                                      5009
```

<210> SEQ ID NO 74
<211> LENGTH: 4605
<212> TYPE: DNA
<213> ORGANISM: artificial
<220> FEATURE:
<223> OTHER INFORMATION: vector pYD1lnk

<400> SEQUENCE: 74

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga    120
```

```
acaataaaga ttctacaata ctagctttta tggttatgaa gaggaaaaat tggcagtaac    180
ctggccccac aaaccttcaa atgaacgaat caaattaaca accataggat gataatgcga    240
ttagttttttt agccttattt ctggggtaat taatcagcga agcgatgatt tttgatctat   300
taacagatat ataaatgcaa aaactgcata accactttaa ctaatacttt caacattttc    360
ggtttgtatt acttcttatt caatgtaat aaaagtatca acaaaaatt gttaatatac      420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgcttcagt gctagccgct ggggccatgg    600
ttactgattg gcgcgccgga tccttcagac tctgcagaat tcggccgcgt acttaattaa    660
gtttaaaccc gctgatctga taacaacagt gtagatgtaa caaatcgac tttgttccca     720
ctgtactttt agctcgtaca aatacaata tactttttcat ttctccgtaa acaacatgtt    780
ttcccatgta atatccttttt ctattttttcg ttccgttacc aacttttacac atactttata 840
tagctattca cttctataca ctaaaaaact aagacaattt taattttgct gcctgccata   900
tttcaattttg ttataaaattc ctataatttta tcctattagt agctaaaaaa agatgaatgt 960
gaatcgaatc ctaagagaat tgggcaagtg cacaaacaat acttaaataa atactactca  1020
gtaataacct atttcttagc atttttgacg aaatttgcta ttttgttaga gtcttttaca   1080
ccatttgtct ccacacctcc gcttacatca acaccaataa cgccatttaa tctaagcgca   1140
tcaccaacat tttctggcgt cagtccacca gctaacataa aatgtaagct ctcggggctc   1200
tcttgccttc caacccagtc agaaatcgag ttccaatcca aaagttcacc tgtcccacct   1260
gcttctgaat caaacaaggg aataaacgaa tgaggtttct gtgaagctgc actgagtagt   1320
atgttgcagt cttttggaaa tacgagtctt ttaataactg gcaaaccgag gaactcttgg   1380
tattcttgcc acgactcatc tccgtgcagt tggacgatat caatgccgta atcattgacc   1440
agagccaaaa catcctcctt aggttgatta cgaaacacgc caaccaagta tttcggagtg   1500
cctgaactat ttttatatgc ttttacaaga cttgaaattt tccttgcaat aaccgggtca   1560
attgttctct ttctattggg cacacatata atacccagca agtcagcatc ggaatctaga   1620
gcacattctg cggcctctgt gctctgcaag ccgcaaactt tcaccaatgg accagaacta   1680
cctgtgaaat taataacaga catactccaa gctgcctttg tgtgcttaat cacgtatact   1740
cacgtgctca atagtcacca atgccctccc tcttggccct ctccttttct tttttcgacc   1800
gaatttcttg aagacgaaag ggcctcgtga tacgcctatt tttataggtt aatgtcatga   1860
taataatggt ttcttaggac ggatcgcttg cctgtaactt acacgcgcct cgtatctttt   1920
aatgatggaa taatttggga atttactctg tgtttattta tttttatgtt ttgtatttgg   1980
atttagaaa gtaaataaag aaggtagaag agttacggaa tgaagaaaaa aaaataaaca    2040
aaggtttaaa aaatttcaac aaaaagcgta ctttacatat atatttatta gacaagaaaa   2100
gcagattaaa tagatataca ttcgattaac gataagtaaa atgtaaaatc acaggatttt   2160
cgtgtgtggt cttctacaca gacaagatga aacaattcgg cattaatacc tgagagcagg   2220
aagagcaaga taaaggtag tatttgttgg cgatcccct agagtctttt acatcttcgg     2280
aaaacaaaaa ctattttttc tttaatttct ttttttactt tctattttta atttatatat   2340
ttatattaaa aaatttaaat tataattatt tttatagcac gtgatgaaaa ggacccaggt   2400
ggcactttc ggggaaatgt gcgcggaacc cctatttgtt tatttttcta aatacattca    2460
aatatgtatc cgctcatgag acaataaccc tgataaatgc ttcaataata ttgaaaaagg   2520
```

```
aagagtatga gtattcaaca tttccgtgtc gcccttattc ccttttttgc ggcattttgc    2580
cttcctgttt ttgctcaccc agaaacgctg gtgaaagtaa aagatgctga agatcagttg    2640
ggtgcacgag tgggttacat cgaactggat ctcaacagcg gtaagatcct tgagagtttt    2700
cgccccgaag aacgttttcc aatgatgagc acttttaaag ttctgctatg tggcgcggta    2760
ttatcccgtg ttgacgccgg gcaagagcaa ctcggtcgcc gcatacacta ttctcagaat    2820
gacttggttg agtactcacc agtcacagaa aagcatctta cggatggcat gacagtaaga    2880
gaattatgca gtgctgccat aaccatgagt gataacactg cggccaactt acttctgaca    2940
acgatcggag gaccgaagga gctaaccgct tttttgcaca acatggggga tcatgtaact    3000
cgccttgatc gttgggaacc ggagctgaat gaagccatac caaacgacga gcgtgacacc    3060
acgatgcctg tagcaatggc aacaacgttg cgcaaactat taactggcga actacttact    3120
ctagcttccc ggcaacaatt aatagactgg atggaggcgg ataaagttgc aggaccactt    3180
ctgcgctcgg cccttccggc tggctggttt attgctgata aatctggagc cggtgagcgt    3240
gggtctcgcg gtatcattgc agcactgggg ccagatggta agccctcccg tatcgtagtt    3300
atctacacga cggggagtca ggcaactatg gatgaacgaa atagacagat cgctgagata    3360
ggtgcctcac tgattaagca ttggtaactg tcagaccaag tttactcata tatactttag    3420
attgatttaa aacttcattt ttaatttaaa aggatctagg tgaagatcct ttttgataat    3480
ctcatgacca aaatccctta acgtgagttt tcgttccact gagcgtcaga ccccgtagaa    3540
aagatcaaag gatcttcttg agatcctttt tttctgcgcg taatctgctg cttgcaaaca    3600
aaaaaaccac cgctaccagc ggtggtttgt ttgccggatc aagagctacc aactcttttt    3660
ccgaaggtaa ctggcttcag cagagcgcag ataccaaata ctgtccttct agtgtagccg    3720
tagttaggcc accacttcaa gaactctgta gcaccgccta catacctcgc tctgctaatc    3780
ctgttaccag tggctgctgc cagtggcgat aagtcgtgtc ttaccgggtt ggactcaaga    3840
cgatagttac cggataaggc gcagcggtcg ggctgaacgg ggggttcgtg cacacagccc    3900
agcttggagc gaacgaccta caccgaactg agatacctac agcgtgagca ttgagaaagc    3960
gccacgcttc ccgaagggag aaaggcggac aggtatccgg taagcggcag ggtcggaaca    4020
ggagagcgca cgagggagct tccagggggg aacgcctggt atctttatag tcctgtcggg    4080
tttcgccacc tctgacttga gcgtcgattt ttgtgatgct cgtcaggggg gcggagccta    4140
tggaaaaacg ccagcaacgc ggcctttttta cggttcctgg ccttttgctg gccttttgct    4200
cacatgttct ttcctgcgtt atcccctgat tctgtggata accgtattac cgcctttgag    4260
tgagctgata ccgctcgccg cagccgaacg accgagcgca gcgagtcagt gagcgaggaa    4320
gcggaagagc gcccaatacg caaaccgcct ctccccgcgc gttggccgat tcattaatgc    4380
agctggcacg acaggtttcc cgactggaaa gcgggcagtg agcgcaacgc aattaatgtg    4440
agttacctca ctcattaggc accccaggct ttacacttta tgcttccggc tcctatgttg    4500
tgtggaattg tgagcggata acaatttcac acaggaaaca gctatgacca tgattacgcc    4560
aagctcggaa ttaaccctca ctaaagggaa caaaagctgg ctagt                    4605
```

<210> SEQ ID NO 75
<211> LENGTH: 4886
<212> TYPE: DNA
<213> ORGANISM: artificial
<220> FEATURE:
<223> OTHER INFORMATION: vector pYD1mata

<400> SEQUENCE: 75

```
acggattaga agccgccgag cgggtgacag ccctccgaag gaagactctc ctccgtgcgt    60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagttttt agccttattt ctggggtaat taatcagcga agcgatgatt tttgatctat   300
taacagatat ataaatgcaa aaactgcata accactttaa ctaatacttt caacattttc   360
ggtttgtatt acttcttatt caatgtaat aaaagtatca acaaaaaatt gttaatatac   420
ctctatactt taacgtcaag gagaaaaaac cccggatcgg actactagca gctgtaatac   480
gactcactat agggaatatt aagctaattc tacttcatac atttcaatt aagatgcagt   540
tacttcgctg tttttcaata ttttctgtta ttgcttcagt gctagccgct ggggccatgg   600
ttactgattg gcgcgccgga tccgatgtaa caaaatcgac tttgttccca ctgtactttt   660
agctcgtaca aaatacaata tacttttcat ttctccgtaa acaacatgtt ttcccatgta   720
atatcctttt ctattttcg ttccgttacc aactttacac atactttata tagctattca   780
cttctataca ctaaaaaact aagacaattt taattttgct gcctgccata tttcaatttg   840
ttataaattc ctataattta tcctattagt agctaaaaaa agatgaatgt gaatcgaatc   900
ctaagagaat tgctgcagaa ttcggccgcg tacttaatta agtttaaacc cgctgatctg   960
ataacaacag tgtagatgta acaaaatcga ctttgttccc actgtacttt tagctcgtac  1020
aaaatacaat atacttttca tttctccgta acaacatgt tttcccatgt aatatccttt  1080
tctattttc gttccgttac aactttaca catactttat atagctattc acttctatac  1140
actaaaaaac taagacaatt ttaattttgc tgcctgccat atttcaattt gttataaatt  1200
cctataattt atcctattag tagctaaaaa aagatgaatg tgaatcgaat cctaagagaa  1260
ttgggcaagt gcacaaacaa tacttaaata aatactactc agtaataacc tatttcttag  1320
cattttgac gaaatttgct attttgttag agtcttttac accatttgtc tccacacctc  1380
cgcttacatc aacaccaata acgccattta atctaagcgc atcaccaaca ttttctggcg  1440
tcagtccacc agctaacata aaatgtaagc tctcggggct ctcttgcctt ccaacccagt  1500
cagaaatcga gttccaatcc aaaagttcac ctgtcccacc tgcttctgaa tcaaacaagg  1560
gaataaacga atgaggtttc tgtgaagctg cactgagtag tatgttgcag tcttttggaa  1620
atacgagtct tttaataact ggcaaaccga ggaactcttg gtattcttgc cacgactcat  1680
ctccgtgcag ttggacgata tcaatgccgt aatcattgac cagagccaaa acatcctcct  1740
taggttgatt acgaaacacg ccaaccaagt atttcggagt gcctgaacta ttttatatg  1800
cttttacaag acttgaaatt ttccttgcaa taaccgggtc aattgttctc tttctattgg  1860
gcacacatat aatacccagc aagtcagcat cggaatctag agcacattct gcggcctctg  1920
tgctctgcaa gccgcaaact ttcaccaatg gaccagaact acctgtgaaa ttaataacag  1980
acatactcca agctgccttt gtgtgcttaa tcacgtatac tcacgtgctc aatagtcacc  2040
aatgccctcc ctcttggccc tctccttttc ttttttcgac cgaatttctt gaagacgaaa  2100
gggcctcgtg atacgcctat ttttataggt taatgtcatg ataataatgg tttcttagga  2160
cggatcgctt gcctgtaact tacacgcgcc tcgtatcttt taatgatgga ataatttggg  2220
aatttactct gtgtttattt attttatgt tttgtatttg gatttagaa agtaaataaa  2280
gaaggtagaa gagttacgga atgaagaaaa aaaaataaac aaaggtttaa aaaatttcaa  2340
```

```
caaaaagcgt actttacata tatatttatt agacaagaaa agcagattaa atagatatac    2400
attcgattaa cgataagtaa aatgtaaaat cacaggattt tcgtgtgtgg tcttctacac    2460
agacaagatg aaacaattcg gcattaatac ctgagagcag gaagagcaag ataaaaggta    2520
gtatttgttg gcgatccccc tagagtcttt tacatcttcg gaaaacaaaa actattttt     2580 ctttaatttc tttttttact ttctatttt  aatttatata tttatattaa aaaatttaaa    2640
ttataattat tttatagca cgtgatgaaa aggacccagg tggcactttt cggggaaatg     2700
tgcgcggaac ccctatttgt ttattttct aaatacattc aaatatgtat ccgctcatga     2760
gacaataacc ctgataaatg cttcaataat attgaaaaag gaagagtatg agtattcaac    2820
atttccgtgt cgcccttatt cccttttttg cggcattttg ccttcctgtt tttgctcacc    2880
cagaaacgct ggtgaaagta aaagatgctg aagatcagtt gggtgcacga gtgggttaca    2940
tcgaactgga tctcaacagc ggtaagatcc ttgagagttt tcgccccgaa gaacgttttc    3000
caatgatgag cacttttaaa gttctgctat gtggcgcggt attatcccgt gttgacgccg    3060
ggcaagagca actcggtcgc cgcatacact attctcagaa tgacttggtt gagtactcac    3120
cagtcacaga aaagcatctt acggatggca tgacagtaag agaattatgc agtgctgcca    3180
taaccatgag tgataacact gcggccaact tacttctgac aacgatcgga ggaccgaagg    3240
agctaaccgc ttttttgcac aacatggggg atcatgtaac tcgccttgat cgttgggaac    3300
cggagctgaa tgaagccata ccaaacgacg agcgtgacac cacgatgcct gtagcaatgg    3360
caacaacgtt gcgcaaacta ttaactggcg aactacttac tctagcttcc cggcaacaat    3420
taatagactg gatggaggcg gataaagttg caggaccact tctgcgctcg gcccttccgg    3480
ctggctggtt tattgctgat aaatctggag ccggtgagcg tgggtctcgc ggtatcattg    3540
cagcactggg gccagatggt aagccctccc gtatcgtagt tatctacacg acgggcagtc    3600
aggcaactat ggatgaacga atagacaga  tcgctgagat aggtgcctca ctgattaagc    3660
attggtaact gtcagaccaa gtttactcat atatacttta gattgattta aaacttcatt    3720
tttaatttaa aaggatctag gtgaagatcc ttttttgataa tctcatgacc aaaatccctt    3780
aacgtgagtt ttcgttccac tgagcgtcag accccgtaga aaagatcaaa ggatcttctt    3840
gagatccttt ttttctgcgc gtaatctgct gcttgcaaac aaaaaaacca ccgctaccag    3900
cggtggtttg tttgccggat caagagctac caactctttt tccgaaggta actggcttca    3960
gcagagcgca gataccaaat actgtccttc tagtgtagcc gtagttaggc caccacttca    4020
agaactctgt agcaccgcct acatacctcg ctctgctaat cctgttacca gtggctgctg    4080
ccagtggcga taagtcgtgt cttaccgggt tggactcaag acgatagtta ccggataagg    4140
cgcagcggtc gggctgaacg gggggttcgt gcacacagcc cagcttggag cgaacgacct    4200
acaccgaact gagataccta cagcgtgagc attgagaaag cgccacgctt cccgaaggga    4260
gaaaggcgga caggtatccg gtaagcggca gggtcggaac aggagagcgc acgagggagc    4320
ttccaggggg gaacgcctgg tatctttata gtcctgtcgg gtttcgccac ctctgacttg    4380
agcgtcgatt tttgtgatgc tcgtcagggg ggccgagcct atggaaaaac gccagcaacg    4440
cggccttttt acgttcctg gccttttgct ggccttttgc tcacatgttc tttcctgcgt     4500 tatccctga ttctgtggat aaccgtatta ccgcctttga gtgagctgat accgctcgcc     4560
gcagccgaac gaccgagcgc agcgagtcag tgagcgagga agcggaagag cgcccaatac    4620
gcaaaccgcc tctccccgcg cgttggccga ttcattaatg cagctggcac gacaggtttc    4680
```

| ccgactggaa agcgggcagt gagcgcaacg caattaatgt gagttacctc actcattagg | 4740 |
| cacccccaggc tttacacttt atgcttccgg ctcctatgtt gtgtggaatt gtgagcggat | 4800 |
| aacaatttca cacaggaaac agctatgacc atgattacgc caagctcgga attaaccctc | 4860 |
| actaaaggga acaaaagctg gctagt | 4886 |

<210> SEQ ID NO 76
<211> LENGTH: 5801
<212> TYPE: DNA
<213> ORGANISM: artificial
<220> FEATURE:
<223> OTHER INFORMATION: vector pYD1gal

<400> SEQUENCE: 76

| acggattaga agccgccgag cgggtgacag ccctccgaag gaagactctc ctccgtgcgt | 60 |
| cctcgtcttc accggtcgcg ttcctgaaac gcagatgtgc ctcgcgccgc actgctccga | 120 |
| acaataaaga ttctacaata ctagctttta tggttatgaa gaggaaaaat tggcagtaac | 180 |
| ctggccccac aaaccttcaa atgaacgaat caaattaaca accataggat gataatgcga | 240 |
| ttagtttttt agccttattt ctggggtaat taatcagcga agcgatgatt tttgatctat | 300 |
| taacagatat ataaatgcaa aaactgcata accactttaa ctaatacttt caacattttc | 360 |
| ggtttgtatt acttcttatt caaatgtaat aaaagtatca acaaaaaatt gttaatatac | 420 |
| ctctatactt taacgtcaag gagaaaaaac cccggatcgg actactagca gctgtaatac | 480 |
| gactcactat agggaatatt aagctaattc tacttcatac attttcaatt aagatgcagt | 540 |
| tacttcgctg ttttttcaata ttttctgtta ttgcttcagt gctagccgct ggggccatgg | 600 |
| ttactgattg gcgcgccgga tccgatgtaa caaaatcgac tttgttccca ctgtactttt | 660 |
| agctcgtaca aaatcaata tacttttcat ttctccgtaa acaacatgtt ttcccatgta | 720 |
| atatcctttt ctatttttcg ttccgttacc aactttacac atactttata tagctattca | 780 |
| cttctataca ctaaaaaact aagacaattt taattttgct gcctgccata tttcaatttg | 840 |
| ttataaattc ctataattta tcctattagt agctaaaaaa agatgaatgt gaatcgaatc | 900 |
| ctaagagaat tgctgcagaa ttcacggatt agaagccgcc gagcgggtga cagccctccg | 960 |
| aaggaagact ctcctccgtg cgtcctcgtc ttcaccggtc gcgttcctga acgcagatg | 1020 |
| tgcctcgcgc cgcactgctc cgaacaataa agattctaca atactagctt ttatggttat | 1080 |
| gaagaggaaa aattggcagt aacctggccc cacaaaacctt caaatgaacg aatcaaatta | 1140 |
| acaaccatag gatgataatg cgattagttt ttagcctta tttctggggt aattaatcag | 1200 |
| cgaagcgatg atttttgatc tattaacaga tatataaatg caaaaactgc ataaccactt | 1260 |
| taactaatac tttcaacatt ttcggttttgt attacttctt attcaaatgt aataaaagta | 1320 |
| tcaacaaaaa attgttaata tacctctata ctttaacgtc aaggagaaaa accccggat | 1380 |
| cggactacta gcagctgtaa tacgactcac tatagggaat attaagctaa ttctacttca | 1440 |
| tacatttttca attaagatgc agttacttcg ctgtttttca atatttttctg ttattgcttc | 1500 |
| agttttagca caggaactga caactatatg cgagcaaatc ccctcaccaa ctttagaatc | 1560 |
| gacgccgtac tctttgtcaa cgactactat tttggccaac gggaaggcaa tgcaaggagt | 1620 |
| ttttgaatat tacaaatcag taacgtttgt cagtaattgc ggttctcacc cctcaacaac | 1680 |
| tagcaaaggc agccccataa acacacagta tgtttttaag cttctgcagg ctagtggtgg | 1740 |
| tggtggttct ggtggtggtg gttctggtgg tggtggttct gctagcatga ctggtggcca | 1800 |
| gcaaggccta attctgatgc ggccgcacat catcaccatc accattgatt aattaagttt | 1860 |

```
aaacccgctg atctgataac aacagtgtag atgtaacaaa atcgactttg ttcccactgt   1920
acttttagct cgtacaaaat acaatatact tttcatttct ccgtaaacaa catgttttcc   1980
catgtaatat cctttctat ttttcgttcc gttaccaact ttacacatac tttatatagc    2040
tattcacttc tatacactaa aaaactaaga caatttaat tttgctgcct gccatatttc    2100
aatttgttat aaattcctat aatttatcct attagtagct aaaaaaagat gaatgtgaat   2160
cgaatcctaa gagaattggg caagtgcaca aacaatactt aaataaatac tactcagtaa   2220
taacctattt cttagcattt ttgacgaaat ttgctatttt gttagagtct tttacaccat   2280
ttgtctccac acctccgctt acatcaacac caataacgcc atttaatcta agcgcatcac   2340
caacattttc tggcgtcagt ccaccagcta acataaaatg taagctctcg ggctctctt   2400 gccttccaac ccagtcagaa atcgagttcc aatccaaaag ttcacctgtc ccacctgctt   2460
ctgaatcaaa caagggaata aacgaatgag gtttctgtga agctgcactg agtagtatgt   2520
tgcagtcttt tggaaatacg agtcttttaa taactggcaa accgaggaac tcttggtatt   2580
cttgccacga ctcatctccg tgcagttgga cgatatcaat gccgtaatca ttgaccagag   2640
ccaaaacatc ctccttaggt tgattacgaa acacgccaac caagtatttc ggagtgcctg   2700
aactattttt atatgctttt acaagacttg aaattttcct tgcaataacc gggtcaattg   2760
ttctctttct attgggcaca catataatac ccagcaagtc agcatcggaa tctagagcac   2820
attctgcggc ctctgtgctc tgcaagccgc aaactttcac caatggacca gaactacctg   2880
tgaaattaat aacagacata ctccaagctg cctttgtgtg cttaatcacg tatactcacg   2940
tgctcaatag tcaccaatgc cctccctctt ggccctctcc ttttcttttt tcgaccgaat   3000
ttcttgaaga cgaaagggcc tcgtgatacg cctattttta taggttaatg tcatgataat   3060
aatggtttct taggacggat cgcttgcctg taacttacac gcgcctcgta tcttttaatg   3120
atggaataat ttgggaattt actctgtgtt tatttatttt tatgttttgt atttggattt   3180
tagaaagtaa ataagaaagg tagaagagtt acggaatgaa gaaaaaaaaa taaacaaagg   3240
tttaaaaaat ttcaacaaaa agcgtacttt acatatatat ttattagaca agaaaagcag   3300
attaaataga tatacattcg attaacgata agtaaaatgt aaaatcacag gattttcgtg   3360
tgtggtcttc tacacagaca agatgaaaca attcggcatt aatacctgag agcaggaaga   3420
gcaagataaa aggtagtatt tgttggcgat ccccctagag tcttttacat cttcggaaaa   3480
caaaaactat ttttctttta atttcttttt ttactttcta tttttaattt atatatttat   3540
attaaaaaat ttaaattata attattttta tagcacgtga tgaaaaggac ccaggtggca   3600
cttttcgggg aaatgtgcgc ggaaccccta tttgtttatt tttctaaata cattcaaata   3660
tgtatccgct catgagacaa taaccctgat aaatgcttca ataatattga aaaggaaga   3720 gtatgagtat tcaacatttc cgtgtcgccc ttattccctt ttttgcggca ttttgccttc   3780 ctgttttgc tcacccagaa acgctggtga agtaaaaga tgctgaagat cagttgggtg    3840
cacgagtggg ttacatcgaa ctggatctca acagcggtaa gatccttgag agttttcgcc   3900
ccgaagaacg ttttccaatg atgagcactt taaagttct gctatgtggc gcggtattat    3960
cccgtgttga cgccgggcaa gagcaactcg gtcgccgcat acactattct cagaatgact   4020
tggttgagta ctcaccagtc acagaaaagc atcttacgga tggcatgaca gtaagagaat   4080
tatgcagtgc tgccataacc atgagtgata acactgcggc caacttactt ctgacaacga   4140
tcggaggacc gaaggagcta accgcttttt tgcacaacat gggggatcat gtaactcgcc   4200
```

```
ttgatcgttg ggaaccggag ctgaatgaag ccataccaaa cgacgagcgt gacaccacga    4260
tgcctgtagc aatggcaaca acgttgcgca aactattaac tggcgaacta cttactctag    4320
cttcccggca acaattaata gactggatgg aggcggataa agttgcagga ccacttctgc    4380
gctcggccct tccggctggc tggtttattg ctgataaatc tggagccggt gagcgtgggt    4440
ctcgcggtat cattgcagca ctggggccag atggtaagcc ctcccgtatc gtagttatct    4500
acacgacggg cagtcaggca actatggatg aacgaaatag acagatcgct gagataggtg    4560
cctcactgat taagcattgg taactgtcag accaagttta ctcatatata ctttagattg    4620
atttaaaact tcatttttaa tttaaaagga tctaggtgaa gatcctttt gataatctca    4680 tgaccaaaat cccttaacgt gagttttcgt tccactgagc gtcagacccc gtagaaaaga    4740
tcaaaggatc ttcttgagat cctttttttc tgcgcgtaat ctgctgcttg caaacaaaaa    4800
aaccaccgct accagcggtg gtttgtttgc cggatcaaga gctaccaact cttttccga    4860 aggtaactgg cttcagcaga gcgcagatac caaatactgt ccttctagtg tagccgtagt    4920
taggccacca cttcaagaac tctgtagcac cgcctacata cctcgctctg ctaatcctgt    4980
taccagtggc tgctgccagt ggcgataagt cgtgtcttac cgggttggac tcaagacgat    5040
agttaccgga taaggcgcag cggtcgggct gaacggggg ttcgtgcaca cagcccagct    5100
tggagcgaac gacctacacc gaactgagat acctacagcg tgagcattga aaagcgcca    5160 cgcttcccga agggagaaag gcggacaggt atccggtaag cggcagggtc ggaacaggag    5220
agcgcacgag ggagcttcca ggggggaacg cctggtatct ttatagtcct gtcgggtttc    5280
gccacctctg acttgagcgt cgatttttgt gatgctcgtc aggggggccg agcctatgga    5340
aaaacgccag caacgcggcc ttttacggt tcctggcctt tgctggcct tttgctcaca    5400 tgttctttcc tgcgttatcc cctgattctg tggataaccg tattaccgcc tttgagtgag    5460
ctgataccgc tcgccgcagc cgaacgaccg agcgcagcga gtcagtgagc gaggaagcgg    5520
aagagcgccc aatacgcaaa ccgcctctcc ccgcgcgttg gccgattcat taatgcagct    5580
ggcacgacag gtttcccgac tggaaagcgg gcagtgagcg caacgcaatt aatgtgagtt    5640
acctcactca ttaggcaccc caggctttac actttatgct tccggctcct atgttgtgtg    5700
gaattgtgag cggataacaa tttcacacag gaaacagcta tgaccatgat tacgccaagc    5760
tcggaattaa ccctcactaa agggaacaaa agctggctag t                       5801
```

<210> SEQ ID NO 77
<211> LENGTH: 692
<212> TYPE: DNA
<213> ORGANISM: artificial
<220> FEATURE:
<223> OTHER INFORMATION: 4D5H

<400> SEQUENCE: 77

```
ggccagcaag gccaagaggt tcaactagtg gagtctggcg gtggcctggt gcagccaggg    60
ggctcactcc gtttgtcctg tgcagcttct ggcttcaaca ttaaagacac ctatatacac   120
tgggtgcgtc aggcccccggg taagggcctg gaatggggttg caaggattta tcctacgaat   180
ggttatacta gatatgccga tagcgtcaag ggccgtttca ctataagcgc agacacatcc   240
aaaaacacag cctacctgca gatgaacagc ctgcgtgctg aggacactgc cgtctattat   300
tgttctagat ggggagggga cggcttctat gctatggact actggggtca aggaaccctg   360
gtcaccgtct cctcggctag caccaagggc ccagcgtgt ccctctggc ccccagctcc   420 aagagcacct ccggcggcac cgccgccctg ggctgcctgg tgaaggatta cttcccagag   480
```

```
cccgtgaccg tgagctggaa cagcggcgcc ctgaccagcg gcgtgcacac ctttcccgcc    540
gtgctgcagt ccagcggcct gtactccctg agcagcgtgg tgaccgtgcc cagcagcagc    600
ctgggcaccc agacctacat ctgcaatgtg aaccacaagc ccagcaatac caaggtggat    660
aagaaggtgg agcccaagag ctgcgcggcc gc                                  692

<210> SEQ ID NO 78
<211> LENGTH: 661
<212> TYPE: DNA
<213> ORGANISM: artificial
<220> FEATURE:
<223> OTHER INFORMATION: 4D5L

<400> SEQUENCE: 78
ccatggcgga tatccagatg acccagtccc cgagctccct gtccgcctct gtgggcgata     60
gggtcaccat cacctgccgt gccagtcagg atgtgaatac tgctgtagcc tggtatcaac    120
agaaaccagg aaaagctccg aaactactga tttactcggc atccttcctc tactctggag    180
tcccttctcg cttctctgga tccagatctg gacggattt cactctgacc atcagcagtc     240
tgcagccgga agacttcgca acttattact gtcagcaaca ttatactact cctcccacgt    300
tcggacaggg taccaaggtg gagatcaaac gtacggtggc ggcgccatct gtcttcatct    360
tcccgccatc tgatgagcag ttaagtctg gaactgcctc tgttgtgtgc ctgctgaata    420
acttctatcc cagagaggcc aaagtacagt ggaaggtgga taacgccctc caatcgggta    480
actcccagga gagtgtcaca gagcaggaca gcaaggacag cacctacagc ctcagcagca    540
ccctgacgct gagcaaagca gactacgaga acacaaagt ctacgcctgc gaagtcaccc     600
atcagggcct gagctcgccc gtcacaaaga gcttcaacag gggagagtgt tgaggcgcgc    660
c                                                                    661

<210> SEQ ID NO 79
<211> LENGTH: 6468
<212> TYPE: DNA
<213> ORGANISM: artificial
<220> FEATURE:
<223> OTHER INFORMATION: vector pYD4D5hc

<400> SEQUENCE: 79
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg ttttttcaata ttttctgtta ttgcttcagt gctagccgct ggggccatgg    600
ttactgattg gcgcgccgga tccgatgtaa caaaatcgac tttgttccca ctgtactttt    660
agctcgtaca aaatacaata tactttttcat ttctccgtaa acaacatgtt tcccatgta    720 atatcctttt ctatttttcg ttccgttacc aactttacac atactttata tagctattca    780
```

```
cttctataca ctaaaaaact aagacaattt taattttgct gcctgccata tttcaatttg    840
ttataaattc ctataattta tcctattagt agctaaaaaa agatgaatgt gaatcgaatc    900
ctaagagaat tgctgcagaa ttcacggatt agaagccgcc gagcgggtga cagccctccg    960
aaggaagact ctcctccgtg cgtcctcgtc ttcaccggtc gcgttcctga aacgcagatg   1020
tgcctcgcgc cgcactgctc cgaacaataa agattctaca atactagctt ttatggttat   1080
gaagaggaaa aattggcagt aacctggccc cacaaacctt caaatgaacg aatcaaatta   1140
acaaccatag gatgataatg cgattagttt tttagcctta tttctggggt aattaatcag   1200
cgaagcgatg atttttgatc tattaacaga tatataaatg caaaaactgc ataaccactt   1260
taactaatac tttcaacatt ttcggtttgt attacttctt attcaaatgt aataaaagta   1320
tcaacaaaaa attgttaata tacctctata ctttaacgtc aaggagaaaa accccggat   1380 cggactacta gcagctgtaa tacgactcac tatagggaat attaagctaa ttctacttca   1440
tacattttca attaagatgc agttacttcg ctgtttttca atattttctg ttattgcttc   1500
agttttagca caggaactga caactatatg cgagcaaatc ccctcaccaa ctttagaatc   1560
gacgccgtac tctttgtcaa cgactactat tttggccaac gggaaggcaa tgcaaggagt   1620
ttttgaatat tacaaatcag taacgtttgt cagtaattgc ggttctcacc cctcaacaac   1680
tagcaaaggc agccccataa acacacagta tgtttttaag cttctgcagg ctagtggtgg   1740
tggtggttct ggtggtggtg gttctggtgg tggtggttct gctagcatga ctggtggcca   1800
gcaaggccaa ggttctgagg ttcaactagt ggagtctggc ggtggcctgg tgcagccagg   1860
gggctcactc cgtttgtcct gtgcagcttc tggcttcaac attaaagaca cctatataca   1920
ctgggtgcgt caggcccggg taagggcct ggaatgggtt gcaaggattt atcctacgaa   1980
tggttatact agatatgccg atagcgtcaa gggccgtttc actataagcg cagacacatc   2040
caaaaacaca gcctacctgc agatgaacag cctgcgtgct gaggacactg ccgtctatta   2100
ttgttctaga tggggagggg acggcttcta tgctatggac tactgggtc aaggaaccct   2160 ggtcaccgtc tcctcggcta gcaccaaggg ccccagcgtg ttccctctgg cccccagctc   2220
caagagcacc tccggcggca ccgccgcccct gggctgcctg gtgaaggatt acttcccaga   2280
gcccgtgacc gtgagctgga acagcggcgc cctgaccagc ggcgtgcaca cctttcccgc   2340
cgtgctgcag tccagcggcc tgtactccct gagcagcgtg gtgaccgtgc ccagcagcag   2400
cctgggcacc cagacctaca tctgcaatgt gaaccacaag cccagcaata ccaaggtgga   2460
taagaaggtg gagcccaaga gctgcgcggc cgcacatcat caccatcacc attgattaat   2520
taagtttaaa cccgctgatc tgataacaac agtgtagatg taacaaaatc gactttgttc   2580
ccactgtact tttagctcgt acaaaataca atatactttt catttctccg taaacaacat   2640
gttttcccat gtaatatcct tttctatttt tcgttccgtt accaacttta cacatacttt   2700
atatagctat tcacttctat acactaaaaa actaagacaa ttttaatttt gctgcctgcc   2760
atatttcaat ttgttataaa ttcctataat ttatcctatt agtagctaaa aaagatgaa   2820 tgtgaatcga atcctaagag aattgggcaa gtgcacaaac aatacttaaa taaatactac   2880
tcagtaataa cctatttctt agcattttg acgaaatttg ctattttgtt agagtctttt   2940
acaccatttg tctccacacc tccgcttaca tcaacaccaa taacgccatt taatctaagc   3000
gcatcaccaa cattttctgg cgtcagtcca ccagctaaca taaaatgtaa gctctcgggg   3060
ctctcttgcc ttccaaccca gtcagaaatc gagttccaat ccaaaagttc acctgtccca   3120
cctgcttctg aatcaaacaa gggaataaac gaatgaggtt tctgtgaagc tgcactgagt   3180
```

```
agtatgttgc agtcttttgg aaatacgagt cttttaataa ctggcaaacc gaggaactct    3240
tggtattctt gccacgactc atctccgtgc agttggacga tatcaatgcc gtaatcattg    3300
accagagcca aaacatcctc cttaggttga ttacgaaaca cgccaaccaa gtatttcgga    3360
gtgcctgaac tattttata tgcttttaca agacttgaaa ttttccttgc aataaccggg     3420
tcaattgttc tctttctatt gggcacacat ataatccca gcaagtcagc atcggaatct     3480
agagcacatt ctgcggcctc tgtgctctgc aagccgcaaa ctttcaccaa tggaccagaa    3540
ctacctgtga aattaataac agacatactc caagctgcct tgtgtgctt aatcacgtat      3600 actcacgtgc tcaatagtca ccaatgccct ccctcttggc cctctccttt tcttttttcg     3660
accgaatttc ttgaagacga aagggcctcg tgatacgcct attttatag gttaatgtca      3720 tgataataat ggtttcttag gacggatcgc ttgcctgtaa cttacacgcg cctcgtatct     3780
tttaatgatg gaataatttg ggaatttact ctgtgtttat ttatttttat gttttgtatt     3840
tggattttag aaagtaaata aagaaggtag aagagttacg gaatgaagaa aaaaaaataa    3900
acaaaggttt aaaaaatttc aacaaaaagc gtactttaca tatatattta ttagacaaga    3960
aaagcagatt aaatagatat acattcgatt aacgataagt aaaatgtaaa atcacaggat    4020
tttcgtgtgt ggtcttctac acagacaaga tgaaacaatt cggcattaat acctgagagc    4080
aggaagagca agataaaagg tagtatttgt tggcgatccc cctagagtct tttacatctt    4140
cggaaaacaa aaactatttt ttcttaatt tcttttttta ctttctattt ttaatttata     4200
tatttatatt aaaaaattta aattataatt attttatag cacgtgatga aaaggaccca     4260
ggtggcactt ttcggggaaa tgtgcgcgga accctattt gtttatttt ctaaatacat      4320 tcaaatatgt atccgctcat gagacaataa ccctgataaa tgcttcaata atattgaaaa    4380
aggaagagta tgagtattca acatttccgt gtcgccctta ttccctttt tgcggcattt     4440 tgccttcctg ttttgctca cccagaaacg ctggtgaaag taaaagatgc tgaagatcag    4500
ttgggtgcac gagtgggtta catcgaactg gatctcaaca gcggtaagat ccttgagagt    4560
tttcgccccg aagaacgttt tccaatgatg agcactttta aagttctgct atgtggcgcg    4620
gtattatccc gtgttgacgc cgggcaagag caactcggtc gccgcataca ctattctcag    4680
aatgacttgg ttgagtactc accagtcaca gaaaagcatc ttacggatgg catgacagta    4740
agagaattat gcagtgctgc cataaccatg agtgataaca ctgcggccaa cttacttctg    4800
acaacgatcg gaggaccgaa ggagctaacc gcttttttgc acaacatggg ggatcatgta    4860
actcgccttg atcgttggga accggagctg aatgaagcca taccaaacga cgagcgtgac    4920
accacgatgc ctgtagcaat ggcaacaacg ttgcgcaaac tattaactgg cgaactactt    4980
actctagctt cccggcaaca attaatagac tggatggagg cggataaagt tgcaggacca    5040
cttctgcgct cggcccttcc ggctggctgg tttattgctg ataaatctgg agccggtgag    5100
cgtgggtctc gcggtatcat tgcagcactg gggccagatg gtaagccctc ccgtatcgta    5160
gttatctaca cgacgggcag tcaggcaact atggatgaac gaaatagaca gatcgctgag    5220
ataggtgcct cactgattaa gcattggtaa ctgtcagacc aagtttactc atatatactt    5280
tagattgatt taaaacttca ttttaattt aaaaggatct aggtgaagat ccttttgat     5340 aatctcatga ccaaaatccc ttaacgtgag ttttcgttcc actgagcgtc agaccccgta    5400
gaaaagatca aaggatcttc ttgagatcct ttttttctgc gcgtaatctg ctgcttgcaa    5460
acaaaaaaac caccgctacc agcggtggtt tgtttgccgg atcaagagct accaactctt    5520
```

```
tttccgaagg taactggctt cagcagagcg cagataccaa atactgtcct tctagtgtag    5580
ccgtagttag gccaccactt caagaactct gtagcaccgc ctacatacct cgctctgcta    5640
atcctgttac cagtggctgc tgccagtggc gataagtcgt gtcttaccgg gttggactca    5700
agacgatagt taccggataa ggcgcagcgg tcgggctgaa cggggggttc gtgcacacag    5760
cccagcttgg agcgaacgac ctacaccgaa ctgagatacc tacagcgtga gcattgagaa    5820
agcgccacgc ttcccgaagg gagaaaggcg gacaggtatc cggtaagcgg cagggtcgga    5880
acaggagagc gcacgaggga gcttccaggg gggaacgcct ggtatcttta tagtcctgtc    5940
gggtttcgcc acctctgact tgagcgtcga ttttgtgat gctcgtcagg ggggccgagc    6000
ctatggaaaa acgccagcaa cgcggccttt ttacggttcc tggccttttg ctggccttt    6060 gctcacatgt tctttcctgc gttatcccct gattctgtgg ataaccgtat taccgccttt    6120
gagtgagctg ataccgctcg ccgcagccga acgaccgagc gcagcgagtc agtgagcgag    6180
gaagcggaag agcgcccaat acgcaaaccg cctctccccg cgcgttggcc gattcattaa    6240
tgcagctggc acgacaggtt tcccgactgg aaagcgggca gtgagcgcaa cgcaattaat    6300
gtgagttacc tcactcatta ggcaccccag gctttacact ttatgcttcc ggctcctatg    6360
ttgtgtggaa ttgtgagcgg ataacaattt cacacaggaa acagctatga ccatgattac    6420
gccaagctcg gaattaaccc tcactaaagg gaacaaaagc tggctagt                 6468
```

<210> SEQ ID NO 80
<211> LENGTH: 223
<212> TYPE: PRT
<213> ORGANISM: artificial
<220> FEATURE:
<223> OTHER INFORMATION: 4D5hp

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
              195                 200                 205
Pro Ser Asn Thr Lys Val Asp Lys Lys Val Glu Pro Lys Ser Cys
   210                 215                 220
```

<210> SEQ ID NO 81
<211> LENGTH: 7100
<212> TYPE: DNA
<213> ORGANISM: artificial
<220> FEATURE:
<223> OTHER INFORMATION: vector pYD4D5hl

<400> SEQUENCE: 81

```
acggattaga agccgccgag cgggtgacag ccctccgaag gaagactctc ctccgtgcgt    60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
taacagatat ataaatgcaa aaactgcata accactttaa ctaatacttt caacattttc   360
ggtttgtatt acttcttatt caaatgtaat aaaagtatca acaaaaaatt gttaatatac   420
ctctatactt taacgtcaag gagaaaaaac cccggatcgg actactagca gctgtaatac   480
gactcactat agggaatatt aagctaattc tacttcatac attttcaatt aagatgcagt   540
tacttcgctg tttttcaata ttttctgtta ttgcttcagt gctagccgct ggggccatgg   600
cggatatcca gatgacccag tccccgagct ccctgtccgc ctctgtgggc gatagggtca   660
ccatcacctg ccgtgccagt caggatgtga atactgctgt agcctggtat caacagaaac   720
caggaaaagc tccgaaacta ctgatttact cggcatcctt cctctactct ggagtccctt   780
ctcgcttctc tggatccaga tctgggacgg atttcactct gaccatcagc agtctgcagc   840
cggaagactt cgcaacttat tactgtcagc aacattatac tactcctccc acgttcggac   900
agggtaccaa ggtggagatc aaacgtacgg tggcggcgcc atctgtcttc atcttcccgc   960
catctgatga gcagcttaag tctgaactg cctctgttgt gtgcctgctg ataacttct  1020
atcccagaga ggccaaagta cagtggaagg tggataacgc cctccaatcg ggtaactccc  1080
aggagagtgt cacagagcag gacagcaagg acagcaccta gcctcagc agcaccctga  1140
cgctgagcaa agcagactac gagaaacaca agtctacgc ctgcgaagtc acccatcagg  1200
gcctgagctc gcccgtcaca aagagcttca caggggaga gtgttgaggc gcgccggatc  1260
cgatgtaaca aaatcgactt tgttcccact gtacttttag ctcgtacaaa atacaatata  1320
cttttcattt ctccgtaaac aacatgtttt cccatgtaat atccttttct atttttcgtt  1380
ccgttaccaa ctttacacat actttatata gctattcact tctatacact aaaaaactaa  1440
gacaatttta attttgctgc ctgccatatt tcaatttgtt ataaattcct ataatttatc  1500
ctattagtag ctaaaaaaag atgaatgtga atcgaatcct aagagaattg ctgcagaatt  1560
cacggattag aagccgccga gcgggtgaca gccctccgaa ggaagactct cctccgtgcg  1620
tcctcgtctt caccggtcgc gttcctgaaa cgcagatgtg cctcgcgccg cactgctccg  1680
aacaataaag attctacaat actagctttt atggttatga gaggaaaaa ttggcagtaa  1740
cctggcccca caaaccttca atgaacgaa tcaaattaac aaccatagga tgataatgcg  1800
attagttttt tagccttatt tctggggtaa ttaatcagcg aagcgatgat ttttgatcta  1860
ttaacagata tataaatgca aaaactgcat aaccacttta actaatactt tcaacatttt  1920
```

```
cggtttgtat tacttcttat tcaaatgtaa taaaagtatc aacaaaaaat tgttaatata      1980
cctctatact ttaacgtcaa ggagaaaaaa ccccggatcg gactactagc agctgtaata      2040
cgactcacta tagggaatat taagctaatt ctacttcata cattttcaat taagatgcag      2100
ttacttcgct gtttttcaat attttctgtt attgcttcag ttttagcaca ggaactgaca      2160
actatatgcg agcaaatccc ctcaccaact ttagaatcga cgccgtactc tttgtcaacg      2220
actactattt tggccaacgg gaaggcaatg caaggagttt ttgaatatta caaatcagta      2280
acgtttgtca gtaattgcgg ttctcacccc tcaacaacta gcaaaggcag ccccataaac      2340
acacagtatg ttttaagct tctgcaggct agtggtggtg gtggttctgg tggtggtggt       2400
tctggtggtg gtggttctgc tagcatgact ggtggccagc aaggccaaga ggttcaacta      2460
gtggagtctg gcggtggcct ggtgcagcca gggggctcac tccgtttgtc ctgtgcagct      2520
tctggcttca acattaaaga cacctatata cactgggtgc gtcaggcccc gggtaagggc      2580
ctggaatggg ttgcaaggat ttatcctacg aatggttata ctagatatgc cgatagcgtc      2640
aagggccgtt tcactataag cgcagacaca tccaaaaaca gcctacct gcagatgaac        2700 agcctgcgtg ctgaggacac tgccgtctat tattgttcta gatgggggag gacggcttc      2760 tatgctatgg actactgggg tcaaggaacc ctggtcaccg tctcctcggc tagcaccaag      2820
ggccccagcg tgttccctct ggccccagc tccaagagca cctccggcgg caccgccgcc       2880
ctgggctgcc tggtgaagga ttacttccca gagcccgtga ccgtgagctg aacagcggc       2940 gccctgacca gcggcgtgca cacctttccc gccgtgctgc agtccagcgg cctgtactcc      3000
ctgagcagcg tggtgaccgt gcccagcagc agcctgggca cccagaccta catctgcaat      3060
gtgaaccaca agcccagcaa taccaaggtg gataagaagg tggagcccaa gagctgcgcg      3120
gccgcacatc atcaccatca ccattgatta attaagttta aacccgctga tctgataaca      3180
acagtgtaga tgtaacaaaa tcgactttgt tcccactgta cttttagctc gtacaaaata      3240
caatatactt tcatttctc cgtaaacaac atgtttttccc atgtaatatc cttttctatt      3300
tttcgttccg ttaccaactt tacacatact ttatatagct attcacttct atacactaaa      3360
aaactaagac aattttaatt ttgctgcctg ccatatttca atttgttata aattcctata      3420
atttatccta ttagtagcta aaaaaagatg aatgtgaatc gaatcctaag agaattgggc      3480
aagtgcacaa acaatactta aataaatact actcagtaat aacctatttc ttagcatttt      3540
tgacgaaatt tgctattttg ttagagtctt ttacaccatt tgtctccaca cctccgctta      3600
catcaacacc aataacgcca tttaatctaa gcgcatcacc aacattttct ggcgtcagtc      3660
caccagctaa cataaaatgt aagctctcgg gctctcttg ccttccaacc cagtcagaaa       3720
tcgagttcca atccaaaagt tcacctgtcc cacctgcttc tgaatcaaac aagggaataa      3780
acgaatgagg tttctgtgaa gctgcactga gtagtatgtt gcagtctttt ggaaatacga      3840
gtcttttaat aactggcaaa ccgaggaact cttggtattc ttgccacgac tcatctccgt      3900
gcagttggac gatatcaatg ccgtaatcat tgaccagagc caaaacatcc tccttaggtt      3960
gattacgaaa cacgccaacc aagtatttcg gagtgcctga actattttta tatgctttta      4020
caagacttga aattttcctt gcaataaccg ggtcaattgt tctctttcta ttgggcacac      4080
atataatacc cagcaagtca gcatcggaat ctagagcaca ttctgcggcc tctgtgctct      4140
gcaagccgca aactttcacc aatggaccag aactacctgt gaaattaata acagacatac      4200
tccaagctgc ctttgtgtgc ttaatcacgt atactcacgt gctcaatagt caccaatgcc      4260
ctccctcttg gccctctcct tttctttttt cgaccgaatt tcttgaagac gaaagggcct      4320
```

```
cgtgatacgc ctattttat aggttaatgt catgataata atggtttctt aggacggatc    4380
gcttgcctgt aacttacacg cgcctcgtat cttttaatga tggaataatt tgggaattta    4440
ctctgtgttt atttattttt atgttttgta tttggatttt agaaagtaaa taaagaaggt    4500
agaagagtta cggaatgaag aaaaaaaaat aaacaaaggt ttaaaaaatt tcaacaaaaa    4560
gcgtacttta catatatatt tattagacaa gaaaagcaga ttaaatagat atacattcga    4620
ttaacgataa gtaaaatgta aaatcacagg attttcgtgt gtggtcttct acacagacaa    4680
gatgaaacaa ttcggcatta atacctgaga gcaggaagag caagataaaa ggtagtattt    4740
gttggcgatc ccctagagt cttttacatc ttcggaaaac aaaaactatt ttttcttaa     4800 ttctttttt  tactttctat ttttaattta tatatttata ttaaaaaatt taaattataa    4860
ttatttttat agcacgtgat gaaaaggacc caggtggcac ttttcgggga aatgtgcgcg    4920 gaaccctat  ttgtttattt ttctaaatac attcaaatat gtatccgctc atgagacaat    4980
aaccctgata aatgcttcaa taatattgaa aaaggaagag tatgagtatt caacatttcc    5040
gtgtcgccct tattcccttt tttgcggcat tttgccttcc tgttttgct cacccagaaa     5100 cgctggtgaa agtaaaagat gctgaagatc agttgggtgc acgagtgggt tacatcgaac    5160
tggatctcaa cagcggtaag atccttgaga gttttcgccc cgaagaacgt tttccaatga    5220
tgagcacttt taaagttctg ctatgtggcg cggtattatc ccgtgttgac gccgggcaag    5280
agcaactcgg tcgccgcata cactattctc agaatgactt ggttgagtac tcaccagtca    5340
cagaaaagca tcttacggat ggcatgacag taagagaatt atgcagtgct gccataacca    5400
tgagtgataa cactgcggcc aacttacttc tgacaacgat cggaggaccg aaggagctaa    5460
ccgctttttt gcacaacatg ggggatcatg taactcgcct tgatcgttgg aaccggagc     5520 tgaatgaagc cataccaaac gacgagcgtg acaccacgat gcctgtagca atggcaacaa    5580
cgttgcgcaa actattaact ggcgaactac ttactctagc ttcccggcaa caattaatag    5640
actggatgga ggcggataaa gttgcaggac cacttctgcg ctcggccctt ccggctggct    5700
ggtttattgc tgataaatct ggagccggtg agcgtgggtc tcgcggtatc attgcagcac    5760
tggggccaga tggtaagccc tcccgtatcg tagttatcta cacgacgggc agtcaggcaa    5820
ctatggatga acgaaataga cagatcgctg agataggtgc ctcactgatt aagcattggt    5880
aactgtcaga ccaagtttac tcatatatac tttagattga tttaaaactt cattttaat    5940 ttaaaggat  ctaggtgaag atcctttttg ataatctcat gaccaaaatc ccttaacgtg    6000
agttttcgtt ccactgagcg tcagaccccg tagaaaagat caaaggatct tcttgagatc    6060 cttttttct  gcgcgtaatc tgctgcttgc aaacaaaaaa accaccgcta ccagcggtgg    6120
tttgtttgcc ggatcaagag ctaccaactc ttttccgaa ggtaactggc ttcagcagag    6180
cgcagatacc aaatactgtc cttctagtgt agccgtagtt aggccaccac ttcaagaact    6240
ctgtagcacc gcctacatac ctcgctctgc taatcctgtt accagtggct gctgccagtg    6300
gcgataagtc gtgtcttacc gggttggact caagacgata gttaccggat aaggcgcagc    6360
ggtcgggctg aacggggggt tcgtgcacac agcccagctt ggagcgaacg acctacaccg    6420
aactgagata cctacagcgt gagcattgag aaagcgccac gcttcccgaa gggagaaagg    6480
cggacaggta tccggtaagc ggcagggtcg gaacaggaga gcgcacgagg gagcttccag    6540
gggggaacgc ctggtatctt tatagtcctg tcgggtttcg ccacctctga cttgagcgtc    6600
gatttttgtg atgctcgtca ggggggcga gcctatggaa aaacgccagc aacgcggcct    6660
```

-continued

```
ttttacggtt cctggccttt tgctggcctt tgctcacat gttctttcct gcgttatccc    6720
ctgattctgt ggataaccgt attaccgcct ttgagtgagc tgataccgct cgccgcagcc    6780
gaacgaccga gcgcagcgag tcagtgagcg aggaagcgga agagcgccca atacgcaaac    6840
cgcctctccc cgcgcgttgg ccgattcatt aatgcagctg gcacgacagg tttcccgact    6900
ggaaagcggg cagtgagcgc aacgcaatta atgtgagtta cctcactcat taggcacccc    6960
aggctttaca ctttatgctt ccggctccta tgttgtgtgg aattgtgagc ggataacaat    7020
ttcacacagg aaacagctat gaccatgatt acgccaagct cggaattaac cctcactaaa    7080
gggaacaaaa gctggctagt                                                 7100
```

<210> SEQ ID NO 82
<211> LENGTH: 214
<212> TYPE: PRT
<213> ORGANISM: artificial
<220> FEATURE:
<223> OTHER INFORMATION: 4D5lp

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 83
<211> LENGTH: 4
<212> TYPE: PRT
<213> ORGANISM: artificial
<220> FEATURE:
<223> OTHER INFORMATION: C-terminal residues of junction region (SEQ ID
      No. 10)

<400> SEQUENCE: 83

Ser Pro Gly Lys
1

<210> SEQ ID NO 84
<211> LENGTH: 10
<212> TYPE: PRT
<213> ORGANISM: artificial
<220> FEATURE:
<223> OTHER INFORMATION: Myc epitope of junction region (SEQ ID No. 10)

<400> SEQUENCE: 84

Glu Gln Lys Leu Ile Ser Glu Glu Asp Leu
1               5                   10

<210> SEQ ID NO 85
<211> LENGTH: 4
<212> TYPE: PRT
<213> ORGANISM: artificial
<220> FEATURE:
<223> OTHER INFORMATION: Residues 18-21 of junction region (SEQ ID No.
      10)

<400> SEQUENCE: 85

Asn Gly Ala Ala
1

<210> SEQ ID NO 86
<211> LENGTH: 4
<212> TYPE: PRT
<213> ORGANISM: artificial
<220> FEATURE:
<223> OTHER INFORMATION: N-terminal residues of junction region (SEQ ID
      No. 10)

<400> SEQUENCE: 86

Thr Val Glu Ser
1

<210> SEQ ID NO 87
<211> LENGTH: 5
<212> TYPE: PRT
<213> ORGANISM: artificial
<220> FEATURE:
<223> OTHER INFORMATION: AB-loop sequence AA143ff

<400> SEQUENCE: 87

Leu Thr Lys Asn Gln
1               5

<210> SEQ ID NO 88
<211> LENGTH: 7
<212> TYPE: PRT
<213> ORGANISM: artificial
<220> FEATURE:
<223> OTHER INFORMATION: EF loop sequence AA198ff

<400> SEQUENCE: 88

Asp Lys Ser Arg Trp Gln Gln
1               5

<210> SEQ ID NO 89
<211> LENGTH: 5
<212> TYPE: PRT
<213> ORGANISM: artificial
<220> FEATURE:
<223> OTHER INFORMATION: linker

<400> SEQUENCE: 89

```
Glu Gly Gly Gly Ser
1               5

<210> SEQ ID NO 90
<211> LENGTH: 105
<212> TYPE: PRT
<213> ORGANISM: artificial
<220> FEATURE:
<223> OTHER INFORMATION: engineered CH3 domain
<220> FEATURE:
<221> NAME/KEY: MISC_FEATURE
<222> LOCATION: (19)..(21)
<223> OTHER INFORMATION: Motif
<220> FEATURE:
<221> NAME/KEY: MISC_FEATURE
<222> LOCATION: (72)..(80)
<223> OTHER INFORMATION: Motif

<400> SEQUENCE: 90

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105

<210> SEQ ID NO 91
<211> LENGTH: 110
<212> TYPE: PRT
<213> ORGANISM: artificial
<220> FEATURE:
<223> OTHER INFORMATION: engineered CH3 domain
<220> FEATURE:
<221> NAME/KEY: MISC_FEATURE
<222> LOCATION: (19)..(21)
<223> OTHER INFORMATION: Xaa can be any naturally occurring amino acid
<220> FEATURE:
<221> NAME/KEY: MISC_FEATURE
<222> LOCATION: (73)..(80)
<223> OTHER INFORMATION: Xaa can be any naturally occurring amino acid
<220> FEATURE:
<221> NAME/KEY: MISC_FEATURE
<222> LOCATION: (83)..(84)
<223> OTHER INFORMATION: Xaa can be any naturally occurring amino acid

<400> SEQUENCE: 91

Gly Gln Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Xaa Xaa Xaa Xaa Xaa Xaa Xaa Xaa
65                  70                  75                  80
```

```
Arg Trp Xaa Xaa Gly Asn Val Phe Ser Cys Ser Val Met His Glu Ala
            85                  90                  95

Leu His Asn His Tyr Thr Gln Lys Ser Leu Ser Leu Ser Pro
            100                 105                 110

<210> SEQ ID NO 92
<211> LENGTH: 110
<212> TYPE: PRT
<213> ORGANISM: artificial
<220> FEATURE:
<223> OTHER INFORMATION: engineered CH3 domain
<220> FEATURE:
<221> NAME/KEY: MISC_FEATURE
<222> LOCATION: (19)..(21)
<223> OTHER INFORMATION: Xaa can be any one of Ala, Asp, Ser or Tyr
<220> FEATURE:
<221> NAME/KEY: MISC_FEATURE
<222> LOCATION: (73)..(80)
<223> OTHER INFORMATION: Xaa can be any one of Ala, Asp, Ser or Tyr
<220> FEATURE:
<221> NAME/KEY: MISC_FEATURE
<222> LOCATION: (83)..(84)
<223> OTHER INFORMATION: Xaa can be any one of Ala, Asp, Ser or Tyr

<400> SEQUENCE: 92

Gly Gln Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Xaa Xaa Xaa Xaa Xaa Xaa Xaa Xaa
65                  70                  75                  80

Arg Trp Xaa Xaa Gly Asn Val Phe Ser Cys Ser Val Met His Glu Ala
            85                  90                  95

Leu His Asn His Tyr Thr Gln Lys Ser Leu Ser Leu Ser Pro
            100                 105                 110

<210> SEQ ID NO 93
<211> LENGTH: 114
<212> TYPE: PRT
<213> ORGANISM: artificial
<220> FEATURE:
<223> OTHER INFORMATION: engineered CH3 domain
<220> FEATURE:
<221> NAME/KEY: MISC_FEATURE
<222> LOCATION: (19)..(21)
<223> OTHER INFORMATION: Xaa can be any naturally occurring amino acid
<220> FEATURE:
<221> NAME/KEY: MISC_FEATURE
<222> LOCATION: (75)..(82)
<223> OTHER INFORMATION: Xaa can be any naturally occurring amino acid
<220> FEATURE:
<221> NAME/KEY: MISC_FEATURE
<222> LOCATION: (87)..(88)
<223> OTHER INFORMATION: Xaa can be any naturally occurring amino acid

<400> SEQUENCE: 93

Gly Gln Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
```

```
                35                  40                  45
Asn Asn Tyr Lys Thr Thr Pro Pro Val Leu Asp Ser Asp Gly Ser Phe
 50                  55                  60

Phe Leu Tyr Ser Lys Leu Thr Val Gly Ser Xaa Xaa Xaa Xaa Xaa
 65                  70                  75                  80

Xaa Xaa Ser Gly Arg Trp Xaa Xaa Gly Asn Val Phe Ser Cys Ser Val
                 85                  90                  95

Met His Glu Ala Leu His Asn His Tyr Thr Gln Lys Ser Leu Ser Leu
                100                 105                 110

Ser Pro

<210> SEQ ID NO 94
<211> LENGTH: 114
<212> TYPE: PRT
<213> ORGANISM: artificial
<220> FEATURE:
<223> OTHER INFORMATION: engineered CH3 domain
<220> FEATURE:
<221> NAME/KEY: MISC_FEATURE
<222> LOCATION: (19)..(21)
<223> OTHER INFORMATION: Xaa can be any one of Ala, Asp, Ser or Tyr
<220> FEATURE:
<221> NAME/KEY: MISC_FEATURE
<222> LOCATION: (75)..(82)
<223> OTHER INFORMATION: Xaa can be any one of Ala, Asp, Ser or Tyr
<220> FEATURE:
<221> NAME/KEY: MISC_FEATURE
<222> LOCATION: (87)..(88)
<223> OTHER INFORMATION: Xaa can be any one of Ala, Asp, Ser or Tyr

<400> SEQUENCE: 94

Gly Gln Pro Arg Glu Pro Gln Val Tyr Thr Leu Pro Pro Ser Arg Asp
 1               5                  10                  15

Glu Leu Xaa Xaa Xaa Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Gly Ser Xaa Xaa Xaa Xaa Xaa
 65                  70                  75                  80

Xaa Xaa Ser Gly Arg Trp Xaa Xaa Gly Asn Val Phe Ser Cys Ser Val
                 85                  90                  95

Met His Glu Ala Leu His Asn His Tyr Thr Gln Lys Ser Leu Ser Leu
                100                 105                 110

Ser Pro

<210> SEQ ID NO 95
<211> LENGTH: 112
<212> TYPE: PRT
<213> ORGANISM: artificial
<220> FEATURE:
<223> OTHER INFORMATION: engineered CH3 domain
<220> FEATURE:
<221> NAME/KEY: MISC_FEATURE
<222> LOCATION: (19)..(23)
<223> OTHER INFORMATION: Xaa can be any one of Ala, Asp, Ser or Tyr
<220> FEATURE:
<221> NAME/KEY: MISC_FEATURE
<222> LOCATION: (20)..(22)
<223> OTHER INFORMATION: Xaa can be any naturally occurring amino acid
<220> FEATURE:
<221> NAME/KEY: MISC_FEATURE
<222> LOCATION: (75)..(82)
```

```
<223> OTHER INFORMATION: Xaa can be any naturally occurring amino acid
<220> FEATURE:
<221> NAME/KEY: MISC_FEATURE
<222> LOCATION: (85)..(86)
<223> OTHER INFORMATION: Xaa can be any naturally occurring amino acid

<400> SEQUENCE: 95

Gly Gln Pro Arg Glu Pro Gln Val Tyr Thr Leu Pro Pro Ser Arg Asp
  1               5                  10                  15

Glu Leu Xaa Xaa Xaa Xaa Xaa Gln Val Ser Leu Thr Cys Leu Val Lys
             20                  25                  30

Gly Phe Tyr Pro Ser Asp Ile Ala Val Glu Trp Glu Ser Asn Gly Gln
         35                  40                  45

Pro Glu Asn Asn Tyr Lys Thr Thr Pro Val Leu Asp Ser Asp Gly
     50                  55                  60

Ser Phe Phe Leu Tyr Ser Lys Leu Thr Val Xaa Xaa Xaa Xaa Xaa
 65                  70                  75                  80

Xaa Xaa Arg Trp Xaa Xaa Gly Asn Val Phe Ser Cys Ser Val Met His
             85                  90                  95

Glu Ala Leu His Asn His Tyr Thr Gln Lys Ser Leu Ser Leu Ser Pro
            100                 105                 110

<210> SEQ ID NO 96
<211> LENGTH: 112
<212> TYPE: PRT
<213> ORGANISM: artificial
<220> FEATURE:
<223> OTHER INFORMATION: engineered CH3 domain
<220> FEATURE:
<221> NAME/KEY: MISC_FEATURE
<222> LOCATION: (19)..(23)
<223> OTHER INFORMATION: Xaa can be any one of Ala, Asp, Ser or Tyr
<220> FEATURE:
<221> NAME/KEY: MISC_FEATURE
<222> LOCATION: (75)..(82)
<223> OTHER INFORMATION: Xaa can be any one of Ala, Asp, Ser or Tyr
<220> FEATURE:
<221> NAME/KEY: MISC_FEATURE
<222> LOCATION: (85)..(86)
<223> OTHER INFORMATION: Xaa can be any one of Ala, Asp, Ser or Tyr

<400> SEQUENCE: 96

Gly Gln Pro Arg Glu Pro Gln Val Tyr Thr Leu Pro Pro Ser Arg Asp
  1               5                  10                  15

Glu Leu Xaa Xaa Xaa Xaa Xaa Gln Val Ser Leu Thr Cys Leu Val Lys
             20                  25                  30

Gly Phe Tyr Pro Ser Asp Ile Ala Val Glu Trp Glu Ser Asn Gly Gln
         35                  40                  45

Pro Glu Asn Asn Tyr Lys Thr Thr Pro Val Leu Asp Ser Asp Gly
     50                  55                  60

Ser Phe Phe Leu Tyr Ser Lys Leu Thr Val Xaa Xaa Xaa Xaa Xaa
 65                  70                  75                  80

Xaa Xaa Arg Trp Xaa Xaa Gly Asn Val Phe Ser Cys Ser Val Met His
             85                  90                  95

Glu Ala Leu His Asn His Tyr Thr Gln Lys Ser Leu Ser Leu Ser Pro
            100                 105                 110
```

DISPLAY OF BINDING AGENTS

CROSS REFERENCE

This application is a continuation of U.S. application Ser. No. 12/666,618 filed Dec. 23, 2009, which is a 371 U.S. national phase application of International Application No. PCT/AT08/00232 filed Jun. 26, 2008, which claims the benefit of U.S. Provisional Application No. 60/946,287 filed Jun. 26, 2007 and U.S. Provisional Application No. 61/049,826 filed May 2, 2008. The contents of all of the above applications are hereby incorporated by reference in their entirety.

SEQUENCE LISTING

The attached sequence listing "3906_1029_revised_seq_listing_2_23" created Feb. 24, 2016, size 128 kb) is hereby incorporated by reference in its entirety.

The invention relates to a method of preparing a genetic package displaying oligomers of modular antibody domains binding to a target and to a scaffold ligand and vectors and libraries of bivalent genetic packages produced by these methods. The invention further relates to methods of selecting suitable linker sequences for use in such oligomer display.

Monoclonal antibodies have been widely used as a scaffold for binding agents. The basic antibody structure will be explained here using as example an intact IgG1 immunoglobulin.

Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy-terminal CH3, at the base of the Y's stem. A short stretch, the switch, connects the heavy chain variable and constant regions. The hinge connects CH2 and CH3 (the Fc fragment) to the remainder of the antibody (the Fab fragments). One Fc and two identical Fab fragments can be produced by proteolytic cleavage of the hinge in an intact antibody molecule. The light chains are constructed of two domains, variable (VL) and constant (CL), separated by a switch.

Disulfide bonds in the hinge region connect the two heavy chains. The light chains are coupled to the heavy chains by additional disulfide bonds. Asn-linked carbohydrate moieties are attached at different positions in constant domains depending on the class of immunoglobulin. For IgG1 two disulfide bonds in the hinge region, between Cys235 and Cys238 pairs, unite the two heavy chains. The light chains are coupled to the heavy chains by two additional disulfide bonds, between Cys229s in the CH1 domains and Cys214s in the CL domains. Carbohydrate moieties are attached to Asn306 of each CH2, generating a pronounced bulge in the stem of the Y.

These features have profound functional consequences. The variable regions of both the heavy and light chains (VH) and (VL) lie at the "tips" of the Y, where they are positioned to react with antigen. This tip of the molecule is the side on which the N-terminus of the amino acid sequence is located. The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y.

Two types of light chain, termed lambda (λ) and kappa (κ), are found in antibodies. A given immunoglobulin either has K chains or λ chains, never one of each. No functional difference has been found between antibodies having λ or κ light chains.

Each domain in an antibody molecule has a similar structure of two beta sheets packed tightly against each other in a compressed antiparallel beta barrel. This conserved structure is termed the immunoglobulin fold. The immunoglobulin fold of constant domains contains a 3-stranded sheet packed against a 4-stranded sheet. The fold is stabilized by hydrogen bonding between the beta strands of each sheet, by hydrophobic bonding between residues of opposite sheets in the interior, and by a disulfide bond between the sheets. The 3-stranded sheet comprises strands C, F, and G, and the 4-stranded sheet has strands A, B, E, and D. The letters A through G denote the sequential positions of the beta strands along the amino acid sequence of the immunoglobulin fold.

The fold of variable domains has 9 beta strands arranged in two sheets of 4 and 5 strands. The 5-stranded sheet is structurally homologous to the 3-stranded sheet of constant domains, but contains the extra strands C' and C". The remainder of the strands (A, B, C, D, E, F, G) have the same topology and similar structure as their counterparts in constant domain immunoglobulin folds. A disulfide bond links strands B and F in opposite sheets, as in constant domains.

The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B-C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B-C, C'-C", and F-G of the light chain variable domain and strands B-C, C'-C", and F-G of the heavy chain variable domain.

The loops which are not CDR-loops in a native immunoglobulin, or not part of the antigen-binding pocket as determined by the CDR loops and optionally adjacent loops within the CDR loop region, do not have antigen binding or epitope binding specificity, but contribute to the correct folding of the entire immunoglobulin molecule and/or its effector or other functions and are therefore called structural loops for the purpose of this invention.

Prior art documents show that the immunoglobulin-like scaffold has been employed so far for the purpose of manipulating the existing antigen binding site, thereby introducing novel binding properties. In most cases the CDR regions have been engineered for antigen binding, in other words, in the case of the immunoglobulin fold, only the natural antigen binding site has been modified in order to change its binding affinity or specificity. A vast body of literature exists which describes different formats of such manipulated immunoglobulins, frequently expressed in the form of single-chain Fv fragments (scFv) or Fab fragments, either displayed on the surface of phage particles or solubly expressed in various prokaryotic or eukaryotic expression systems.

WO06072620A1 describes a method of engineering an immunoglobulin which comprises a modification in a structural loop region to obtain new antigen binding sites. This method is broadly applicable to immunoglobulins and may be used to produce a series of immunoglobulins targeting a variety of antigens. A CH3 library has been shown to be useful for selecting specific binders to an antigen.

Although multivalent display of proteins on genetic packages has been described (such as direct phage cloning and display, bacterial display, yeast display), prior art refers to monomeric monovalent display of binding domains, in general. WO9209690 describes phagemid particles displaying a single copy of a fusion protein on the surface of the particle. Thereby it was described to obtain high affinity binders from a library of phagemid particles, also called bacteriophages. Replicable expression vectors comprising genes encoding a binding polypeptide and a phage coat protein are provided so to form a gene fusion encoding a fusion protein, which is a chimeric protein of a phagemid particle, the phage coat protein and the binding polypeptide.

U.S. Pat. No. 5,223,409 generally describes the method of fusing a gene encoding a protein of interest to the N-terminal domain of the gene III coat protein of the filamentous phage M13. The gene fusion is mutated to form a library of structurally related fusion proteins that are expressed in low quantity on the surface of a phagemid particle. Biological selection and screening is employed to identify novel ligands useful as drug candidates.

However, there are some limitations in using such "fusion phage" or monovalent phage display and respective single fusion proteins. Many biologicals naturally occur in oligomeric form. For the purpose of the present invention oligomeric means dimeric, trimeric or even higher polymeric forms, up to 24 monomers.

The fusion phages according to the prior art are described to display monomeric fusion proteins, mainly because it was believed that binders of highest affinity could only be selected from a library if single fusion proteins are displayed by the phagemid particles. Native proteins are however often assembled as a dimer or even at a higher degree of oligomerization. To obtain dimeric display with a single fusion protein, some techniques have been developed that involve conditional stop codons located between the coat protein and the binding polypeptide (Dall'Acqua et al The Journal of Immunology, 2002, 169: 5171-5180). Thereby soluble monomers of the polypeptides in addition to those fused to the phage are expressed, thus enabling the formation of a dimer. However, such stop codons requires propagation in specific suppressor host cells that may translate a stop codon in an amino acid, to provide an appropriate amount of fusion proteins in addition to the soluble binding polypeptides. WO 03/029456 describes the use of multi-chain eukaryotic display vectors for the selection of immunoglobulin Fab fragments on the surface of yeast cells.

Prior art fusion proteins involve in some cases linker sequences to display larger binding polypeptides. Linker sequences of up to 24 amino acids are usually employed for standard purposes of displaying variable domains of an antibody. See for example, the display vector pCOMB3× (Hybrid. Hybridomics. 2003 April; 22(2):97-108. Development of functional human monoclonal single-chain variable fragment antibody against HIV-1 from human cervical B cells. Berry J D, Rutherford J, Silverman G J, Kaul R, Elia M, Gobuty S, Fuller R, Plummer F A, Barbas C F.)

It is an object of this invention to provide an effective method for the preparation of oligomers of modular antibody domains and to prepare such oligomers displayed on the surface of a replicable genetic package.

BRIEF DESCRIPTION OF THE INVENTION

The objects are solved by the subject matter of the present invention.

According to the invention a method of preparing a genetic package displaying oligomers of modular antibody domains binding to a target and to a scaffold ligand comprising
  providing a genetic package, and
  displaying at least two of the antibody modular domains
    by fusing to the outer surface of the package
is covered.

The genetic package can be displayed in a mobilized or cellular system, wherein according to the invention the mobilized system can be selected from viruses, phages, phagemids, in-vitro display systems, mRNA systems and ribosomal display systems. Alternatively, a cellular system can be selected using yeast, mammalian cells, bacterial cells, bacterial spores or insect cells.

Oligomers are possibly formed by oligomerization motifs associated with the structure of said agents, such as leucine zipper, disulfide bonds, electrostatic or hydrophobic motifs.

According to one embodiment of the invention the oligomers can be dimers, trimers or tetramers, involving the same type of monomers (homomers) or different types (heteromers). The preferred method according to the invention is specifically useful for providing homomers, in particular homodimers of oligonucleotides on a genetic package, such as a phagemid particle or a phage or yeast.

The method according to the invention can be applied to oligomers which are polypeptides with a target binding site that directs towards the surface of the genetic package and is close to said surface that are biologicals, such as polypeptides.

Alternatively, the appropriate design of such a polypeptide is employed with a binding site that is closer to the surface of the genetic package than to the surrounding environment of the genetic package. This may be advantageous for a binding polypeptide with a potential binding site that is closer to the C-terminus than to the N-terminus of the polypeptide, in particular when the binding site is engineered in a C-terminal loop position. When the potential binding site is engineered at a position that is adjacent to the site where the genetic package particle is bound, for instance to a surface structure of a cell or a virus, it is advantageous to choose a stable construct with defined accessibility of the binding partner of said binding agent. C-terminal loop positions are, for instance, less accessible than N-terminal loop positions, when they are fused to the N-terminus of the protein 3 of a filamentous phage because they are exposed and in sterical proximity to the genetic package.

According to a preferred embodiment of the invention, however, a defined structure, such as a true oligomeric or dimeric fusion protein is provided to enable the efficient engineering of the potential binding site at an N-terminal loop position. One embodiment of the invention refers to polypeptides with at least two target binding sites, possibly engineered at the monomeric or the oligomeric target binding agent. In some cases the interaction between the monomeric structures enables additional variations of structures and thus additional potential binding sites.

According to a preferred embodiment of the invention the modular antibody is an antibody, Fc fragment, an antibody fragment with a CDR region and combinations thereof, possibly also comprising a fragment with a binding site at a structural loop position.

It can also be an antibody fragment with a CDR region like for example Fab, dAb, scFv, diabody, unibody, SMIPs, TANDABS, Fc fusion proteins and combinations thereof.

In case the genetic package is a filamentous bacteriophage, the preferred fusion structure employed with a bacteriophage involves at least part of an outer surface protein, such as p3, p6, or p8, however, p9 or p10 may also be used for the purpose of the invention.

In case the genetic package is yeast it is preferred that the oligomer is a fusion protein comprising one of the proteins of yeast cell surface receptors selected from the group consisting of alpha-agglutinin, a-agglutinin, Aga1p, Aga2p or FL01.

The appropriate genetic package is preferably provided in a particular form, and containing a vector encoding at least one of said fusion proteins. According to the invention there is, for example, provided a cassette vector, containing sequences encoding one or more than one fusion protein operatively linked to the genetic package. Thus, at least two of the chimeric fusion proteins are bound at the surface of the vector particle. The vector can be, for example, a phagemid.

An expression system for expressing oligomers of modular antibody domains bound at the surface of a genetic package produced according to the inventive method is also covered wherein the oligomers are encoded by a single gene and the fusion protein is displayed with at least two copies on the surface of the genetic package.

By using the method and means according to the invention it is possible to display oligomers of modular antibodies without the need of controlled expression of a soluble form of one of the oligomerization partners. The technique can be utilized for molecules such as antibody fragments, even those containing more than two immunoglobulin domains, e.g. at least four immunoglobulin domains. Thus difficult constructs involving stop codons, such as amber stop codons, can be avoided. There will be no need to get a mixture of fusion proteins and soluble monomers for the dimer display. Thus, a preferred technique of managing mixtures of a variety of binding agents can easily be employed, while the risk of insufficient matching of the monomers is reduced. It is also possible to avoid the suppressor strains as a host cell. Conventional host cells, with non-suppressor function, can serve in a standard way to propagate the oligomeric fusion proteins.

In another embodiment according to the invention, the fusion between the binding partner and the surface protein of the genetic package is such that no conditional stop codon (i.e. no amber, ochre, opal or other similar conditional stop codon) is present in between. In such a situation, upon infection with helper phage, the binding partner is present only as a fusion protein and not in soluble form. In order for the dimer (trimer or higher) to form on the surface of the genetic package, the linker which connects the binding partner to the genetic package needs to be of sufficient length and sufficient flexibility. Linkers that fulfil this requirement can be selected using the method described above.

In another embodiment according to the invention, a helper phage can be used that has specific properties that favour the display of more than one copy of the fusion protein on the surface of the genetic package. An example for such a helper phage is the so-called hyperphage (Rondot S, Koch J, Breitling F, Dubel S. A helper phage to improve single-chain antibody presentation in phage display. Nat Biotechnol. 2001 January; 19(1):75-78), which itself is devoid of p3, and therefore depends totally on the p3 fusion protein provided by the phagmid in order to be infective. Using such helper phage leads preferentially to phage particles that carry more than one copies of the fusion protein on their surface, and thus favors the formation of dimers of the binding protein on the surface of the genetic package.

According to a preferred embodiment of the invention each of the fusion protein monomers are prepared in the context of an oligomer, so that the portion of soluble binding agents is less than 20%, more preferably less than 10%, most preferably less than 1%.

According to the inventive method a genetic package can be prepared preferably displaying at least two fusion proteins. In a specific embodiment each monomer of the inventive oligomer is bound to the outer surface of the genetic package. The invention also provides bivalent phage displaying two fusion proteins from oligomers each containing an oligomer that dimerizes upon expression.

A library of genetic packages is also claimed, which can exemplarily comprise at least 10 variant genetic packages, wherein said variant genetic packages can display heteromers of modular antibody domains. The heteromer can be based on a scaffold comprising a target binding site. According to a specific embodiment of the invention the target binding site and the scaffold binding site can be similar or identical. A scaffold ligand according to the invention can also be a CDR target. For example, the scaffold can be a parent Fab and at least 20%, preferably at least 30%, more preferred at least 40% of the parent Fab variants are binding to the CDR-target of said parent Fab.

The inventive library can also contain variants of the oligomer produced according to the invention having differences in the amino acid sequence.

This can be provided by modifying the amino acid sequences by at least one insertion or substitution to introduce at least one foreign amino acid, and by a deletion. Foreign amino acids can be introduced by a randomization technique. The foreign amino acids can also be selected from a specific group of amino acids to obtain a library enriched with specific amino acids at the randomized positions. When the foreign amino acid is selected from a specific group of amino acids, such as amino acids with specific polarity, or hydrophobicity, a library enriched in the specific group of amino acids at the randomized positions can be obtained according to the invention. Such libraries are also called "focused" libraries.

According to the invention there is further provided a method of selecting a linker for binding a polypeptide to the outer surface of a genetic package, comprising
  a. providing a library of genetic packages containing a variety of linkers to connect a first polypeptide to the genetic package,
  b. determining the member of the library containing a linker that does not significantly interfere with the function of said first polypeptide, and
  c. selecting said linker for connecting a second polypeptide to said genetic package.

Thereby suitable linkers to be used for fusion proteins of the same type can be obtained. By the same type of fusion proteins those are meant that link the same formats of genetic packages and binding agent to each other.

Such a method according to the invention can further be used to prepare enriched libraries containing a preselected group of linker variants that fulfil at least one selection criterion, such as flexibility and sterical accessibility of the binding site to the binding partner. This can be determined by measuring the binding properties of a well-known binding agent in the presence of a variety of linker sequences. The enriched library may thus be further selected for another criterion, such as protease resistance, which is e.g. important for the stability in a medium containing bacterial proteases.

The selected specific linker sequence can then be used to prepare libraries of fusion proteins of the same format, however, with variants of the binding agents, thus enabling the identification, selection and preparation of those agents with the best binding properties in predetermined test systems.

In a preferred embodiment according to the invention such a linker is at least 20 amino acids long, preferably at least 25 amino acid residues, more preferably at least 30 amino acid residues, up to 50 amino acid residues. Especially when amino acids such as Gly, Ser or Ala are involved, which are responsible for the flexibility of a linker, such a linker is advantageously used for the display of a potential binding site, which is close to the surface of the genetic package and which potential binding site may not be able to bind to its partner for sterical reasons.

The linker between the protein to be displayed and the anchor protein of the genetic package (in case of filamentous phage e.g. p3, p8, pX, pIX, pVII) is especially important if the potential binding site of the displayed molecule is in spatial vicinity of the phage particle. In antibody libraries utilizing variable domains and antigen binding sites formed by CDR-loops and display of the library members as amino-terminal fusion to p3 the potential antigen binding site is directed away from the phage particle. Therefore, the linker structure between library members and the phage coat protein is not important. Engineering the bottom loops of immunoglobulin domains and performing phage display may however be an inefficient process and decrease yields of antigen binding clones or even preclude it. Varying the linker between a library member protein and its fusion partner on the surface can solve or may at least reduce this problem.

In order to select for optimal linker sequences (in terms of length and flexibility as well as stability) a library of linkers can be prepared in which the anchor protein at the surface of the genetic replicable package is fused to a known binding protein which is for sterical reasons notoriously difficult to select for.

This library of sequences can be varied in length and amino acid content.

Selection methods of the linker library for optimal linkers depend on the application but basically it should be for selecting all properties one wishes to have in a certain methodology. Enrichment against an antigen that is difficult to select may yield linker sequences which allow library members a good access to the antigen. Incubation in protease solutions or under other harsh conditions or frequent passaging through host cells under proteolytic conditions (e.g. old microbial cultures) may be an appropriate selection for stable display linkers.

A library of linkers may be produced by any well known library technology. Synthetic linker sequence lengths may vary between 10-500 amino acids. Alternatively, linker can be complete proteins known to be of flexible nature.

The invention also provides a method of producing an oligomer of modular antibody domains binding to a target comprising the steps of:

providing a library of oligomers of modular antibody domains produced according to the inventive method as described contacting said library with said target in the presence of a scaffold ligand, selecting a library member binding to said target in the presence of a scaffold ligand, and manufacturing a preparation of the functional oligomer.

The scaffold ligand can be selected from the group consisting of an effector molecule, FcRn, serum albumin, Protein A, Protein G, Protein L or a CDR target. As an example, the effector molecule can be selected from the group consisting of CD64, CD16, CD32, Fc receptors.

The oligomers can be dimers selected from the group of VH/VL, CH1/CL, CH2/CH2, CH3/CH3, Fc and Fab, or single chains thereof.

The method according to the invention can provide a library containing at least $10^2$ independent clones expressing functional oligomers of modular antibody domains or variants thereof. The library member can then be selected according to the requested binding affinity, preferably it has a target binding affinity of Kd<$10^{-8}$M. According to the invention it is also provided a pool of preselected independent clones, which is e.g. affinity maturated, which pool comprises preferably at least 10, more preferably at least 100, more preferably at least 1000, more preferably at least 10000, even more than 100000 independent clones. Those libraries, which contain the preselected pools, are preferred sources to select the high affinity modular antibodies according to the invention.

Preferably the library is a yeast library and the yeast host cell exhibits at the surface of the cell the oligomers with the biological activity. The yeast host cell is preferably selected from the genera *Saccharomyces*, *Pichia*, *Hansenula*, *Schizisaccharomyces*, *Kluyveromyces*, *Yarrowia* and *Candida*. Most preferred, the host cell is *Saccharomyces cerevisiae*.

According to a specific embodiment of the invention, the target is a receptor of the erbB class. In this case, by the method of the invention an immunoglobulin can be obtained that binds to a receptor of the erbB class.

The invention further provides a high quality library containing at least $10^6$ independent clones of functional dimers of modular antibody domains or variants thereof, or the pools of optimized or preselected clones, e.g. the affinity matured clones, which pools are containing at least 10 independent clones that are binding to a target and to a scaffold ligand. The target can be a ligand binding to a parent molecule subject to amino acid variation. The parent molecule can be a functional Fc or a functional Fab, or part thereof.

According to a specific embodiment of the invention the parent molecules can be varied by random or site specific mutagenesis.

The library can contain functional dimers of modular antibody domains that are binding to a target and to a scaffold ligand, and at least 20%, preferably at least 30%, more preferred at least 40% of the functional dimers are binding to CD64. This is particularly preferred with a modular antibody that contains CH2 domains, such as an Fc scaffold.

Alternatively, the library can contain functional dimers of modular antibody domains that are binding to a target and to a scaffold ligand, and at least 20%, preferably at least 30%, more preferred at least 40% of the functional dimers are binding to protein A. This is particularly preferred with a modular antibody that contains CH2 and CH3 domains, such as an Fc scaffold.

Alternatively, the library can contain functional dimers of modular antibody domains that are binding to a target and to a scaffold ligand, and at least 20%, preferably at least 30%, more preferred at least 40% of the functional dimers are binding to the same CDR target. This is particularly preferred with modular antibodies containing a variable region, such as an Fab scaffold with specificity to a single CDR target.

FIGURES

FIG. 1:
Schematic presentation of the PCRs used for production of the fragments used for assembly of the library Fcab01. PCR primers are indicated by arrows with their respective 5'-3' orientation, and vertical lines indicate the approximate positions of the introduced restriction sites which were used for assembly of the mutated gene. The restriction sites are contained on the primers for ligations of the PCR fragments.

Figure 2:
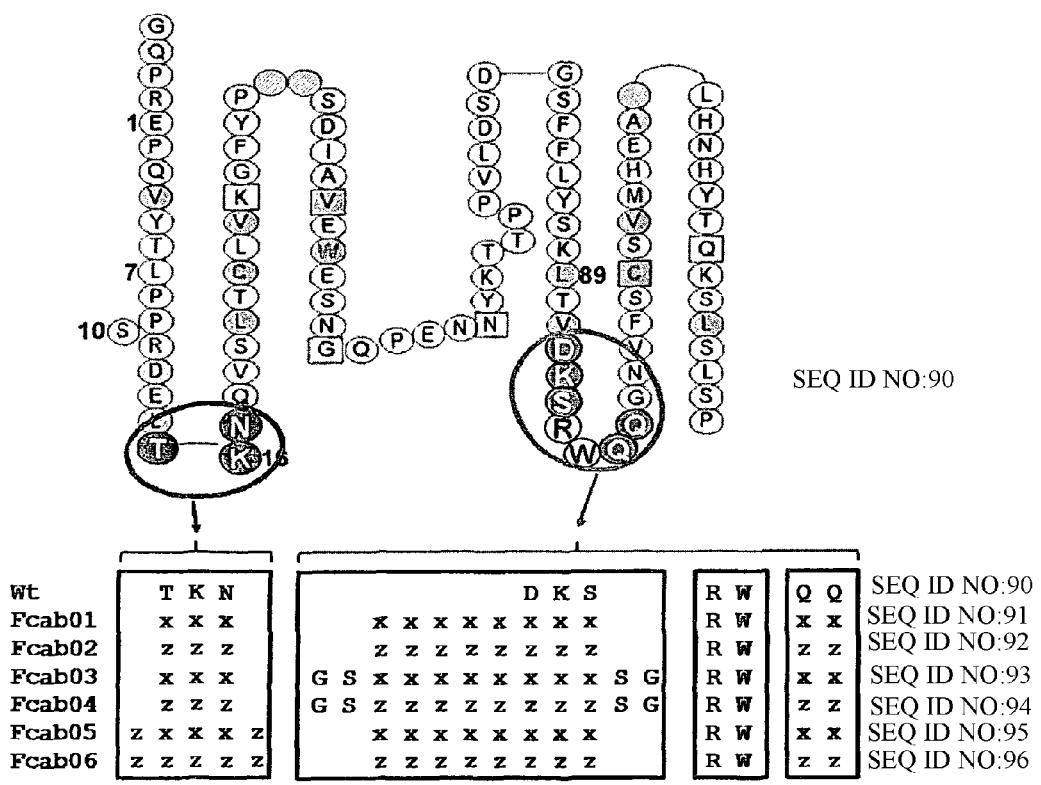

FIG. 2:
Amino acid sequence and secondary structure of a CH3 domain (IMGT numbering). The randomization scheme is provided for the libraries Fcab01 to Fcab06.

Randomized positions in the AB and EF loop are marked with a circle. X stands for all 20 amino acids (encoded by NNB), z only for Ala, Asp, Ser, Tyr (encoded by KMT; focused library).

DETAILED DESCRIPTION OF THE INVENTION

The oligomers of the modular antibody domains according to the present invention will be useful as stand-alone molecules, as well as fusion proteins or derivatives, most typically fused before or after modification in such a way as to be part of larger structures, e.g. of complete antibody molecules, or parts thereof. Immunoglobulins or fusion proteins as produced according to the invention thus also comprise Fc fragments, Fab fragments, Fv fragments, single domain antibodies, single chain antibodies, in particular single-chain Fv fragments, bior multispecific scFv, diabodies, unibodies, multibodies, multivalent or multimers of immunoglobulin domains and others. It will be possible to use the engineered proteins to produce molecules which are monospecific, bispecific, trispecific, and may even carry more specificities. By the invention it is possible to control and preselect the valency of binding at the same time according to the requirements of the planned use of such molecules.

Specific terms as used throughout the specification have the following meaning.

The term "immunoglobulin" as used according to the present invention is defined as polypeptides or proteins that may exhibit mono- or bi- or multi-specific, or mono-, bi- or multivalent binding properties, preferably at least two, more preferred at least three specific binding sites for epitopes of e.g. antigens, effector molecules or proteins either of pathogen origin or of human structure, like self-antigens including cell-associated or serum proteins. The term immunoglobulin as used according to the invention also includes functional fragments of an antibody, such as Fc, Fab, scFv, single chain dimers of CH1/CL domains, Fv, dimers like VH/VL, CH1/CL, CH2/CH2, CH3/CH3, or other derivatives or combinations of the immunoglobulins, like single chains of pairs of immunoglobulin domains. The definition further includes domains of the heavy and light chains of the variable region (such as dAb, Fd, Vl, Vk, Vh, VHH) and the constant region or individual domains of an intact antibody such as CH1, CH2, CH3, CH4, C1 and Ck, as well as mini-domains consisting of at least two beta-strands of an immunoglobulin domain connected by a structural loop.

"Modular antibodies" as used according to the invention are defined as antigen-binding molecules, like human antibodies, composed of at least one polypeptide module or protein domain, preferably in the natural form. The term "modular antibodies" includes antigen-binding molecules that are either immunoglobulins, immunoglobulin-like proteins, or other proteins exhibiting modular formats and antigen-binding properties similar to immunoglobulins or antibodies, which can be used as antigen-binding scaffolds, preferably based on human proteins.

The term "immunoglobulin-like molecule" as used according to the invention refers to any antigen-binding protein, in particular to a human protein, which has a domain structure that can be built in a modular way. Immunoglobulin-like molecules as preferably used for the present invention are T-cell receptors (TCR), fibronectin, transferrin, CTLA-4, single-chain antigen receptors, e.g. those related to T-cell receptors and antibodies, antibody mimetics, adnectins, anticalins, phylomers, repeat proteins such as ankyrin repeats, avimers, Versabodies™, scorpio toxin based molecules, and other non-antibody protein scaffolds with antigen binding properties.

Ankyrin repeat (AR), armadillo repeat (ARM), leucine-rich repeat (LRR) and tetratricopeptide repeat (TPR) proteins are the most prominent members of the protein class of repeat proteins. Repeat proteins are composed of homologous structural units (repeats) that stack to form elongated domains. The binding interaction is usually mediated by several adjacent repeats, leading to large target interaction surfaces.

Avimers contain A-domains as strings of multiple domains in several cell-surface receptors. Domains of this family bind naturally over 100 different known targets, including small molecules, proteins and viruses. Truncation analysis has shown that a target is typically contacted by multiple A-domains with each domain binding independently to a unique epitope. The avidity generated by combining multiple binding domains is a powerful approach to increase affinity and specificity, which these receptors have exploited during evolution Anticalins are engineered human proteins derived from the lipocalin scaffold with defined binding properties typical for humanized antibodies. Lipocalins comprise 160-180 amino acids and form conical beta-barrel proteins with a ligand-binding pocket surrounded by four loops. Small hydrophobic compounds are the natural ligands of lipocalins, and different lipocalin variants with new compound specificities (also termed 'anticalins') could be isolated after randomizing residues in this binding pocket.

Single chain or single domain antigen receptors contain a single variable domain and are 20% smaller than camelid single domain antibodies.

Phylomers are peptides derived from biodiverse natural protein fragments.

It is understood that the term "modular antibody", "immunoglobulin", "immunoglobulin-like proteins" includes a derivative thereof as well. A derivative is any combination of one or more modular antibodies of the invention and or a fusion protein in which any domain or minidomain of the modular antibody of the invention may be fused at any position of one or more other proteins (such as other modular antibodies, immunoglobulins, ligands, scaffold proteins, enzymes, toxins and the like). A derivative of the modular antibody of the invention may also be obtained by association or binding to other substances by various chemical techniques such as covalent coupling, electrostatic interaction, di-sulphide bonding etc. The other substances bound to the immunoglobulins may be lipids, carbohydrates, nucleic acids, organic and inorganic molecules or any combination thereof (e.g. PEG, prodrugs or drugs). A derivative would also comprise an antibody with the same amino acid sequence but made completely or partly from non-natural or chemically modified amino acids.

A "structural loop" or "non-CDR-loop" according to the present invention is to be understood in the following manner: modular antibodies, immunoglobulins or immunoglobulin-like substances are made of domains with a so called immunoglobulin fold. In essence, strands of antiparallel beta sheets are connected by loops to form a compressed antiparallel beta barrel. In the variable region, some of the loops of the domains contribute essentially to the specificity of the antibody, i.e. the binding to an antigen by the natural binding site of an antibody. These loops are called CDR-loops. The CDR loops are located within the CDR loop region, which may in some cases include also the variable framework region (called "VFR") that is adjacent to the CDR loops. It is known that VFRs may contribute to the antigen binding pocket of an antibody, which generally is mainly determined by the CDR loops. Thus, those VFRs are considered as part of the CDR loop region, and would not be appropriately used for engineering new antigen binding sites. Contrary to those VFRs within the CDR loop region or located proximal to the CDR loops, other VFRs of variable domains would be particularly suitable for use according to the invention. Those are the structural loops of the VFRs located opposite to the CDR loop region, or at the C-terminal side of a variable immunoglobulin domain.

The term "antigen" or "target" as used according to the present invention shall in particular include all antigens and target molecules capable of being recognised by a binding site of a modular antibody. Specifically preferred antigens as targeted by the receptor molecule according to the invention are those antigens or molecules, which have already been proven to be or are capable of being immunologically or therapeutically relevant, especially those, for which a clinical efficacy has been tested.

The term "target" or "antigen" as used herein shall comprise molecules selected from the group consisting of allergens, tumor associated antigens, self antigens including cell surface receptors, enzymes, Fc-receptors, FcRn, RSA, IgG, interleukins or cytokines, proteins of the complement system, transport proteins, serum molecules, bacterial antigens, fungal antigens, protozoan antigens and viral antigens, also molecules responsible for transmissible spongiform encephalitis (TSE), such as prions, infective or not, and markers or molecules that relate to inflammatory conditions, such as pro-inflammatory factors, multiple sclerosis or alzheimer disease, or else haptens.

The term "cell surface antigens" shall include all antigens capable of being recognised by an antibody structure on the surface of a cell, and fragments of such molecules. Preferred cell surface antigens are those antigens, which have already been proven to be or which are capable of being immunologically or therapeutically relevant, especially those, for which a preclinical or clinical efficacy has been tested. Those cell surface molecules are specifically relevant for the purpose of the present invention, which mediate cell killing activity. Upon binding of the immunoglobulin according to the invention to preferably at least two of those cell surface molecules the immune system provides for cytolysis or cell death, thus a potent means for attacking human cells may be provided.

The antigen is either recognized as a whole target molecule or as a fragment of such molecule, especially substructures of targets, generally referred to as epitopes.

Substructures of antigens are generally referred to as "epitopes" (e.g. B-cell epitopes, T-cell epitopes), as long as they are immunologically relevant, i.e. are also recognisable by natural or monoclonal antibodies. The term "epitope" as used herein according to the present invention shall mean a molecular structure which may completely make up a specific binding partner or be part of a specific binding partner to a binding site of a modular antibody or an immunoglobulin of the present invention. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably 8 to 50 amino acids, and more preferably between about 10-20 amino acids in the peptide. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide chain. Linear epitopes can be contiguous or overlapping. Conformational epitopes are comprised of amino acids brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

As used herein, the term "specifically binds" or "specific binding" refers to a binding reaction which is determinative of the cognate ligand of interest in a heterogeneous population of molecules. Thus, under designated conditions (e.g. immunoassay conditions), the modular antibody binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may also be integrated into the host chromosome.

Alternatively, an expression system can be used for in vitro transcription/translation. The expression system preferably is employing a host cell that is either a eukaryotic or prokaryotic host cell, preferably a mammalian or yeast host cell, as well as a bacterial host cell.

The preferred expression system for the fusion proteins is a non-suppressor host cell, which would be sensitive to a stop codon, such as an amber stop codon, and would thus stop translation thereafter. In the absence of such a stop codon such non-suppressor host cells, preferably E. coli, are preferably used. In the presence of such a stop codon supressor host cells would be used.

All numbering of the amino acid sequences of the immunoglobulins is according to the IMGT numbering scheme (IMGT, the international ImMunoGeneTics, Lefranc et al., 1999, Nucleic Acids Res. 27: 209-212).

For the purposes of this invention, the term "binding agent" or "ligand" refers to a member of a binding pair, in particular binding polypeptides having the potential of serving as a binding domain for a binding partner. Examples of binding partners include pairs of binding agents with functional interactions, such as receptor binding to ligands, antibody binding to antigen or receptors, a drug binding to a target, and enzyme binding to a substrate The term "fusion protein" or "chimeric fusion protein" as used for the purpose of the invention shall mean the molecule composed of a genetic package, at least part of an outer surface structure, such as a coat protein or part thereof, optionally a linker sequence, and a binding agent. The fusion protein is encoded by a vector with the gene of the binding agent and information to display a copy of the binding agent at the surface of the genetic package.

The term "cytotoxic activity" as used for the purpose of the invention shall mean the activity on effector cells resulting in activation of cytotoxic T-cells or on cells, which mediate antibody-dependent cell cytotoxicity (ADCC), complement dependent cytotoxicity (CDC) and/or antibody-dependent cellular phagocytosis (ADCP). Modular antibodies according to the invention thus kill antibody-coated target cells, which they optionally bind with their Fc receptors.

"Scaffold" shall mean a temporary framework either natural or artificial used to support the molecular structure of a polypeptide in the construction of variants or a repertoire of the polypeptide. It is usually a modular system of polypeptide domains that maintains the tertiary structure or the function of the parent molecule. Exemplary scaffolds are modular antibodies, which may be mutagenized to produce variants within said scaffold, to obtain a library.

The term 'scaffold ligand" as used for the purpose of the invention shall mean a ligand that binds to a scaffold or the backbone of modular antibodies, thus determining the molecular structure or primary function and specificity of said modular antibody. In preferred cases the scaffold ligand is a functional ligand, mediating a biological function upon binding, like an effector ligand. In an alternative embodiment the scaffold ligand is a functional ligand, which is a specific target bound by the CDR region, non-structural loop region or structural loop region. The same scaffold ligand can bind many variants of a modular antibody regardless of their target specificities. In general, the presence of scaffold ligand binding site indicates that the variant is expressed and folded correctly. Thus, binding of the scaffold ligand to its binding site provides a method for preselecting functional polypeptides from a repertoire of polypeptides. Designing variants of modular antibodies that keep the binding property to a scaffold ligand avoids the preparation of variants that are non-functional, for example as a result of the introduction of mutations, folding mutants or expression mutants which would be or are incapable of binding to substantially any target or effector ligand. Such non-functional mutants sometimes are generated by the normal randomisation and variation procedures employed in the construction of polypeptide repertoires. Providing functional mutants that bind to a scaffold ligand permits the person skilled in the art to prepare a library of modular antibodies which is enriched in functional, well folded and highly expressed library members.

The term "effector ligand" as used for the purpose of the invention shall mean a ligand mediating effector functions, like an effector molecule. Exemplary effector ligands are Pc receptors or Pc receptor-like molecules interfering with immunoglobulins. An Pc receptor is a protein found on the surface of certain cells—including natural killer cells, macrophages, neutrophils, and mast cells—that contribute to the protective functions of the immune system. Its name is derived from its binding specificity for a part of an antibody known as the Fc (Fragment-crystallizable) region. Pc receptors bind to antibodies that are attached to infected cells or invading pathogens. Their activity stimulates phagocytic or cytotoxic cells to destroy microbes, or infected cells by antibody-mediated cellular phagocytosis (ADCP) or antibody-dependent cell-mediated cytotoxicity (ADCC). There are several different types of Pc receptors, which are classified based on the type of antibody that they recognize; those that bind the most common class of antibody, IgG, are called Pc-gamma receptors (FcγR), those that bind IgA are called Pc-alpha receptors (FcaR) and those that bind IgE are called Pc-epsilon receptors (FcER). Equivalent to an effector ligand and thus incorporated into the definition is any surrogate ligand that recognizes the same or similar binding site within the modular antibody, such as Protein A.

All FcγRs belong to the immunoglobulin superfamily and are the most important Fc receptors for inducing phagocytosis of opsonized (coated) microbes. This family includes several members that differ in their antibody affinities due to their different molecular structure: FcγRI (CD64), FcγRIIA (CD32a), FcγRIIB (CD32b), FcγRIIIA (CD16a), FcγRIIIB (CD16b. For instance, FcγRI binds to IgG more strongly than FcγRII and FcγRIII, and has an extracellular portion composed of three immunoglobulin (Ig)-like domains, one more domain than FcγRII and FcγRIII. These properties allow activation of FcγRI by a sole IgG molecule (or monomer), while the latter two Fcγ receptors must bind multiple IgG molecules within an immune complex to be activated.

Another FcR is expressed on multiple cell types and is similar in structure to MHC class I. This receptor also binds IgG and is involved in preservation of this antibody in order to increase its biological half-life in vivo. However, since this Fc receptor is also involved in transferring IgG from a mother either via the placenta to her fetus or in milk to her suckling infant, it is called the neonatal Fc receptor (FcRn). Recently this receptor has been implicated in being involved in homeostasis of IgG serum levels.

Antibody-Dependent Cell-Mediated Cytotoxicity (ADCC) is a mechanism of cell-mediated immunity whereby an effector cell of the immune system actively lyses a target cell that has been bound by specific antibodies. It is one of the mechanisms through which antibodies, as part of the humoral immune response, can act to limit and contain infection. Classical ADCC is mediated by natural killer (NK) cells; monocytes and eosinophils can also mediate ADCC. For example Eosinophils can kill certain parasitic worms known as helminths through ADCC. ADCC is part of the adaptive immune response due to its dependence on a prior antibody response.

The term "foreign" in the context of amino acids shall mean the newly introduced amino acids being naturally occurring, but foreign to the site of modification, or substitutes of naturally occurring amino acids. "Foreign" with reference to an antigen binding sites means that the antigen binding site is not naturally formed by the specific binding region of the agent, and a foreign binding partner, but not the natural binding partner of the agent, is bound by the newly engineered binding site.

The term "variable binding region" sometimes called "CDR region" as used herein refers to molecules with varying structures capable of binding interactions with antigens. Those molecules can be used as such or integrated within a larger protein, thus forming a specific region of such protein with binding function. The varying structures can be derived from natural repertoires of binding proteins such as immunoglobulins or phylomers or synthetic diversity, including repeat-proteins, avimers and anticalins. The varying structures can as well be produced by randomization techniques, in particular those described herein. These include mutagenized CDR or non-CDR regions, loop regions of immunoglobulin variable domains or constant domains.

Modified binding agents with different modifications at specific sites are referred to as "variants". Variants of a scaffold are preferably grouped to form libraries of binding agents, which can be used for selecting members of the library with predetermined functions. In accordance therewith, a loop region of a binding agent comprising positions within one or more loops potentially contributing to a binding site, is preferably mutated or modified to produce libraries, preferably by random, semi-random or, in particular, by site-directed random mutagenesis methods, in particular to delete, exchange or introduce randomly generated inserts into loops, preferably into structural loops. Alternatively preferred is the use of combinatorial approaches. Any of the known mutagenesis methods may be employed, among them cassette mutagenesis. These methods may be used to make amino acid modifications at desired positions of the immunoglobulin of the present invention. In some cases positions are chosen randomly, e.g. with either any of the possible amino acids or a selection of preferred amino acids to randomize loop sequences, or amino acid changes are made using simplistic rules. For example all residues may be mutated preferably to specific amino acids, such as alanine, referred to as amino acid or alanine scanning. Such methods may be coupled with more sophisticated engineering approaches that employ selection methods to screen higher levels of sequence diversity.

The preferred cytotoxic modular antibody according to the invention with a molecular weight of less than 60 kD or up to 60 kD has a small size as compared to full length antibodies. The preferred size is up to 55 kD. Modular antibody single domains usually have a molecular size of 10-15 kD, thus a molecule based on 4 modular antibody domains would have a molecular size of 40-60 kD, depending on the glycosylation or any additional conjugation of pharmacologically active substances, like toxins or peptides.

The preferred format is an oligomer, composed of modular antibody domains, preferably up to 4 domains, more preferred 3 domains, and even more preferred made up of 2 domains. Formats based on the combination of 5 modular antibody domains or more are commonly thought not to exert the specific advantages of small sized antibody fragments, which are e.g. ease of expression in various expression systems and tissue penetration.

It is feasible to provide the preferred modular antibody of the invention as a single domain antibody. However, antibody domains tend to dimerize upon expression, either as a homodimer, like an Fc, or a heterodimer, like an Fab. The dimeric structure is thus considered as a basis for the preferred stable molecule. The preferred dimers of immunoglobulin domains are selected from the group consisting of single domain dimers, like VH/VL, CH1/CL (kappa or lambda), CH2/CH2 and CH3/CH3. Dimers or oligomers of modular antibody domains can also be provided as single chain or two chain molecules, in particular those linking the C-terminus of one domain to the N-terminus of another.

Binding partners are agents that specifically bind to one another, usually through non-covalent interactions. Examples of binding partners include pairs of binding agents with functional interactions, such as receptor binding to ligands, antibody binding to antigen, a drug binding to a target, and enzyme binding to a substrate. Binding partners have found use in many therapeutic, diagnostic, analytical and industrial applications. Most prominent binding partners, also called binding pairs, are antibodies or immunoglobulins, fragments or derivatives thereof. In most cases the binding of such binding agents is required to mediate a biological effect or a function, a "functional interaction".

According to a specific embodiment of the present invention the binding agent is an immunoglobulin of human or murine origin, and may be employed for various purposes, in particular in pharmaceutical compositions. Of course, the modified immunoglobulin may also be a humanized or chimeric immunoglobulin.

The binding agent which is a human immunoglobulin is preferably selected or derived from the group consisting of IgA1, IgA2, IgD, IgE, IgG1, IgG2, IgG3, IgG4 and IgM. The murine immunoglobulin binding agent is preferably selected or derived from the group consisting of IgA, IgD, IgE, IgG1, IgG2A, IgG2B, IgG2C, IgG3 and IgM.

Such a binding agent comprises preferably a heavy and/or light chain or a part thereof. A modified immunoglobulin according to the invention may comprise a heavy and/or light chain, at least one variable and/or constant domain, or a part thereof including a minidomain.

A constant domain is an immunoglobulin fold unit of the constant part of an immunoglobulin molecule, also referred to as a domain of the constant region (e.g. CH1, CH2, CH3, CH4, Ck, Cl).

A variable domain is an immunoglobulin fold unit of the variable part of an immunoglobulin, also referred to as a domain of the variable region (e.g. Vh, Vk, Vl, Vd).

An exemplary modular antibody according to the invention consists of a constant domain selected from the group consisting of CH1, CH2, CH3, CH4, Igk-C, Igl-C, combinations, derivatives or a part thereof including a minidomain, with at least one loop region, and is characterised in that said at least one loop region comprises at least one amino acid modification forming at least one modified loop region, wherein said at least one modified loop region binds specifically to at least one epitope of an antigen.

Another modular antibody according to the invention can consist of a variable domain of a heavy or light chain, combinations, derivatives or a part thereof including a minidomain, with at least one loop region, and is characterised in that said at least one loop region comprises at least one amino acid modification forming at least one modified loop region, wherein said at least one modified loop region binds specifically to at least one epitope of an antigen.

The modular antibody according to the present invention may comprise one or more domains (e.g. at least two, three, four, five, six, ten domains). If more than one domain is present in the modular antibody these domains may be of the same type or of varying types (e.g. CH1-CH1-CH2, CH3-

CH3, (CH2)2-(CH3)2, with or without the hinge region). Of course also the order of the single domains may be of any kind (e.g. CH1-CH3-CH2, CH4-CH1-CH3-CH2).

The invention preferably refers to parts of antibodies, such as IgG, IgA, IgM, IgD, IgE and the like. The modular antibodies of the invention may also be a functional antibody fragment such as Fab, Fab2, scFv, Fv, Fc, Fcab™, an antigen-binding Fc, or parts thereof, or other derivatives or combinations of the immunoglobulins such as minibodies, domains of the heavy and light chains of the variable region (such as dAb, Fd (binding site made up of one or more single domains), VL, including Vlambda (Vl) and Vkappa (Vk), VH, VHH) as well as mini-domains consisting of two beta-strands of an immunoglobulin domain connected by at least two structural loops, as isolated domains or in the context of naturally associated molecules. A particular embodiment of the present invention refers to the Fc fragment of an antibody molecule, either as antigen-binding Fc fragment (Fcab™) through modifications of the amino acid sequence or as conjugates or fusions to receptors, peptides or other antigen-binding modules, such as scFv.

The modular antibodies can be used as isolated polypeptides or as combination molecules, e.g. through recombination, fusion or conjugation techniques, with other peptides or polypeptides. The peptides are preferably homologous to immunoglobulin domain sequences, and are preferably at least 5 amino acids long, more preferably at least 10 or even at least 50 or 100 amino acids long, and constitute at least partially the loop region of the immunoglobulin domain. The preferred binding characteristics relate to predefined epitope binding, affinity and avidity.

The modular antibody according to the invention is possibly further combined with one or more modified modular antibodies or with unmodified modular antibodies, or parts thereof, to obtain a combination modular antibody. Combinations are preferably obtained by recombination techniques, but also by binding through adsorption, electrostatic interactions or the like, or else through conjugation or chemical binding with or without a linker. The preferred linker sequence is either a natural linker sequence or a functionally suitable artificial sequence.

In general the modular antibody according to the invention may be used as a building block to molecularly combine other modular antibodies or biologically active substances or molecules. It is preferred to molecularly combine at least one antibody binding to the specific partner via the variable or non-variable sequences, like structural loops, with at least one other binding molecule which can be an antibody, antibody fragment, a soluble receptor, a ligand or another antibody domain, or a binding moiety thereof. Other combinations refer to proteinaceous molecules, nucleic acids, lipids, organic molecules and carbohydrates.

The engineered molecules according to the present invention will be useful as stand-alone proteins as well as fusion proteins or derivatives, most typically fused in such a way as to be part of larger antibody structures or complete antibody molecules, or parts or fragments thereof, such as Fab fragments, Fc fragments, Fv fragments and others. It will be possible to use the engineered proteins to produce molecules which are monospecific, bispecific, trispecific, and maybe even carry more specificities at the same time, and it will be possible at the same time to control and preselect the valency of binding at the same time according to the requirements of the planned use of such molecules.

According to the present invention, the modular antibody optionally exerts one or more binding regions to antigens, including the binding site binding specifically to the cell surface target and the binding sites mediating effector function. Antigen binding sites to one or more antigens may be presented by the CDR-region or any other natural receptor binding structure, or be introduced into a structural loop region of an antibody domain, either of a variable or constant domain structure. The antigens as used for testing the binding properties of the binding sites may be naturally occurring molecules or chemically synthesized molecules or recombinant molecules, either in solution or in suspension, e.g. located on or in particles such as solid phases, on or in cells or on viral surfaces. It is preferred that the binding of an immunoglobulin to an antigen is determined when the antigen is still adhered or bound to molecules and structures in the natural context. Thereby it is possible to identify and obtain those modified immunoglobulins that are best suitable for the purpose of diagnostic or therapeutic use.

Modular antibody or immunoglobulin domains may be modified according to the present invention (as used herein the terms immunoglobulin and antibody are interchangeable) which modifications are preferably effected in immunoglobulin domains or parts thereof that contain a loop, either a CDR-loop or a non-CDR loop, structural loops being the preferred sites of modifications or mutagenesis. In some cases it is preferable to use a defined modified structural loop or a structural loop region, or parts thereof, as isolated molecules for binding or combination purposes.

It is particularly preferred that the modular antibody according to the invention is binding to said cell surface target through at least part of a structural loop and/or CDR loop.

In an alternate embodiment it is preferred that the modular antibody according to the invention is binding to said effector ligand, or a surrogate ligand for such an effector ligand, like protein A, through at least part of a structural loop and/or CDR loop, thus mediating the effector function.

In a preferred embodiment the binding agent is binding with its native or modified binding structure or newly formed binding site, specifically to at least two such epitopes that are identical or differ from each other, either of the same antigen or of different antigens.

In a preferred domain structure of a binding agent it is preferred to modify at least one loop region resulting in a substitution, deletion and/or insertion of one or more nucleotides or amino acids, preferably a point mutation, or even the exchange of whole loops, more preferred the change of at least 2, 3, 4, 5, 6, 7, 8, 9, 10, 11, 12, 13, 14 or 15, up to 30 amino acids. Thereby the modified sequence comprises amino acids not included in the conserved regions of the loops, the newly introduced amino acids being naturally occurring, but foreign to the site of modification, or substitutes of naturally occurring amino acids.

However, the maximum number of amino acids inserted into a loop region of a binding agent preferably may not exceed the number of 30, preferably 25, more preferably 20 amino acids at a maximum. The substitution and the insertion of the amino acids occurs preferably randomly or semi-randomly using all possible amino acids or a selection of preferred amino acids for randomization purposes, by methods known in the art and as disclosed in the present patent application.

The site of modification may be at a specific single loop or a loop region, in particular a structural loop or a structural loop region. A loop region usually is composed of at least one, preferably at least two, preferably at least 3 or at least 4 loops that are at the tip or the bottom of a domain, in proximity or adjacent to each other, and which may contribute to the binding of an antigen through forming an antigen binding site or antigen binding pocket. It is preferred that the one or more sites of modification are located within the area of 10 amino acids, more preferably within 20, 30, 40, 50, 60, 70, 80, 90 up to 100 amino acids, in particular within a structural region to form a surface or pocket where the antigen can sterically access the loop regions.

In this regard the preferred modifications are engineered in the loop regions of CH1, CH2, CH3 and CH4, in particular in the range of amino acids 7 to 21, amino acids 25 to 39, amino acids 41 to 81, amino acids 83 to 85, amino acids 89 to 103 and amino acids 106 to 117.

In another preferred embodiment a modification in the structural loop region comprising amino acids 92 to 98 is combined with a modification in the structural loop region comprising amino acids 8 to 20.

The above identified amino acid regions of the respective immunoglobulins comprise loop regions to be modified. Preferably, a modification in the structural loop region comprising amino acids 92 to 98 is combined with a modification in one or more of the other structural loops.

In a preferred embodiment a modification in the structural loop region comprising amino acids 92 to 98 is combined with a modification in the structural loop region comprising amino acids 41 to 45.2.

Most preferably each of the structural loops comprising amino acids 92 to 98, amino acids 41 to 45.2 and amino acids 8 to 20 contain at least one amino acid modification.

In another preferred embodiment each of the structural loops comprising amino acids 92 to 98, amino acids 41 to 45.2, and amino acids 8 to 20 contain at least one amino acid modification.

According to another preferred embodiment the amino acid residues in the area of positions 15 to 17, 29 to 34, 41 to 45.2, 84 to 85, 92 to 100, and/or 108 to 115 of CH3 are modified.

The preferred modifications of Igk-C and Igl-C of human origin are engineered in the loop regions in the area of amino acids 8 to 20, amino acids 26 to 36, amino acids 41 to 82, amino acids 83 to 88, amino acids 92 to 100, amino acids 107 to 124 and amino acids 123 to 126.

The preferred modifications of loop regions of Igk-C and Igl-C of murine origin are engineered at sites in the area of amino acids 8 to 20, amino acids 26 to 36, amino acids 43 to 79, amino acids 83 to 85, amino acids 90 to 101, amino acids 108 to 116 and amino acids 122 to 126.

Another preferred immunoglobulin preferably used as a therapeutic according to the invention consists of a variable domain of a heavy or light chain, or a part thereof including a minidomain, with at least one loop region, preferably a structural loop region, and is characterised in that said at least one loop region comprises at least one amino acid modification forming at least one modified loop region, wherein said at least one modified loop region forms a relevant binding site as described above.

According to a specific embodiment the immunoglobulin preferably used according to the invention may contain a modification within the variable domain, which is selected from the group of VH, Vkappa, Vlambda, VHH and combinations thereof. More specifically, they comprise at least one modification within amino acids 7 to 22, amino acids 39 to 55, amino acids 66 to 79, amino acids 77 to 89 or amino acids 89 to 104, where the numbering of the amino acid position of the domains is that of the IMGT.

In a specific embodiment, the immunoglobulin preferably used according to the invention is characterised in that the loop regions of VH or Vkappa or Vlambda of human origin comprise at least one modification within amino acids 7 to 22, amino acids 43 to 51, amino acids 67 to 77, amino acids 77 to 88, and amino acids 89 to 104, most preferably amino acid positions 12 to 17, amino acid positions 45 to 50, amino acid positions 68 to 77, amino acids 79 to 88, and amino acid positions 92 to 99, where the numbering of the amino acid position of the domains is that of the IMGT.

The structural loop regions of the variable domain of the immunoglobulin of human origin, as possible selected for modification purposes are preferably located in the area of amino acids 8 to 20, amino acids 44 to 50, amino acids 67 to 76, amino acids 78 to 87, and amino acids 89 to 101.

According to a preferred embodiment the structural loop regions of the variable domain of the immunoglobulin of murine origin as possible selected for modification purposes are preferably located in the area of amino acids 6 to 20, amino acids 43 to 52, amino acids 67 to 79, amino acids 79 to 87, and amino acids 91 to 100.

The immunoglobulin preferably used as a therapeutic according to the invention may also be of camelid origin. Camel antibodies comprise only one heavy chain and have the same antigen affinity as normal antibodies consisting of light and heavy chains. Consequently camel antibodies are much smaller than, e.g., human antibodies, which allows them to penetrate dense tissues to reach the antigen, where larger proteins cannot. Moreover, the comparative simplicity, high affinity and specificity and the potential to reach and interact with active sites, camel's heavy chain antibodies present advantages over common antibodies in the design, production and application of clinically valuable compounds.

According to another preferred embodiment of the present invention the structural loop regions of a modular antibody or an immunoglobulins of camelid origin are modified, e.g. within a VHH, in the region of amino acids 7 to 19, amino acids 43 to 55, amino acids 68 to 76, amino acids 80 to 87 and amino acids 91 to 101.

The preferred method of producing the modular antibody according to the invention refers to engineering a modular antibody that is binding specifically to at least one first epitope and comprising modifications in each of at least two structural loop regions, and determining the specific binding of said at least two loop regions to at least one second epitope, wherein the unmodified structural loop region (non-CDR region) does not specifically bind to said at least one second epitope. Thus, an antibody or antigen-binding structure specific for a first antigen may be improved by adding another valency or specificity against a second antigen, which specificity may be identical, either targeting different epitopes or the same epitope, to increase valency or to obtain bi-, oligo- or multispecific molecules.

On the other hand it is preferred to make use of those modular antibodies that contain native structures interacting with effector molecules or immune cells. Those native structures either remain unchanged or are modulated for an increased effector function. Binding sites for e.g. Fc receptors are described to be located in a CH2 and/or CH3 domain region, and may be mutagenized by well known techniques.

ADCC, antibody-dependent cell-mediated cytotoxicity is the killing of antibody-coated target cells by cells with Fc receptors that recognize the constant region of the bound antibody. Most ADCC is mediated by NK cells that have the Fc receptor FcgammaRIII or CD16 on their surface. Typical assays employ target cells, like Ramos cells, incubated with serially diluted antibody prior to the addition of freshly isolated effector cells. The ADCC assay is then further incubated for several hours and % cytotoxicity detected.

Usually the Target: Effector ratio is about 1:16, but may be 1:1 up to 1:50.

Complement-dependent cytotoxicity (CDC) is a mechanism of killing cells in which antibody bound to the target cell surface fixes complement, which results in assembly of the membrane attack complex that punches holes in the target cell membrane resulting in subsequent cell lysis. The commonly used CDC assay follows the same procedure as for ADCC determination, however, with complement containing serum instead of effector cells.

The cytotoxic activity as determined by either of ADCC and CDC assay is proven for a modular antibody according to the invention, if there is a significant increase in the percentage of cytolysis as compared to a control The absolute percentage increase preferably is higher than 5%, more preferably higher than 10%, even more preferred higher than 20%.

The antibody-dependent cellular phagocytosis, ADCP sometimes called ADPC, is usually investigated side by side with cytolysis of cultured human cells. Phagocytosis by phagocytes, usually human monocytes or monocyte-derived macrophages, as mediated by an antibody can be determined as follows. Purified monocytes may be cultured with cytokines to enhance expression of FcγRs or to induce differentiation into macrophages. ADCP and ADCC assays are then performed with target cells. Phagocytosis is determined as the percentage of positive cells measured by flow cytometry. The positive ADCP activity is proven with a significant uptake of the antibody-antigen complex by the phagocytes. The absolute percentage preferably is higher than 5%, more preferably higher than 10%, even more preferred higher than 20%.

In a typical assay PBMC or monoycytes or monocyte derived macrophages are resuspended in RF2 medium (RPMI 1640 supplemented with 2% FCS) in 96-well plates at a concentration of $1 \times 10^5$ viable cells in 100 ml/well. Appropriate target cells, expressing the target antigen, e.g. Her2/neu antigen and SKBR3 cells, are stained with PKH2 green fluorescence dye. Subsequently $1 \times 10^4$ PKH2-labeled target cells and an Her 2 specific (IgG1) antibody (or modular antibody) or mouse IgG1 isotype control (or modular antibody control) are added to the well of PBMC's in different concentrations (e.g. 1-100 pg/ml) and incubated in a final volume of 200 ml at 37° C. for 24 h. Following the incubation, PBMCs or monoycytes or monocyte derived macrophages and target cells are harvested with EDTA-PBS and transferred to 96-well V-bottomed plates. The plates are centrifuged and the supernatant is aspirated. Cells are counterstained with a 100-ml mixture of RPE-conjugated anti-CD11b, anti-CD14, and human IgG, mixed and incubated for 60 min on ice. The cells are washed and fixed with 2% formaldehyde-PBS. Two-color flow cytometric analysis is performed with e.g. a FACS Calibur under optimal gating. PKH2-labeled target cells (green) are detected in the FL-1 channel (emission wavelength, 530 nm) and RPE-labeled PBMC or monoycytes or monocyte derived macrophages (red) are detected in the FL-2 channel (emission wavelength, 575 nm). Residual target cells are defined as cells that are PKH2$^+$/RPE$^-$ Dual-labeled cells (PKH2$^+$/RPE$^{--}$) are considered to represent phagocytosis of targets by PBMC or monoycytes or monocyte derived macrophages. Phagocytosis of target cells is calculated with the following equation: percent phagocytosis=100×[(percent dual positive)/(percent dual positive+percent residual targets)]. All tests are usually performed in duplicate or triplicate and the results are expressed as mean 6 SD.

The effector function of the modular antibody according to the invention usually differs from any synthetic cytotoxic activity, e.g. through a toxin that may be conjugated to an immunoglobulin structure. Toxins usually do not activate effector molecules and the biological defence mechanism. Thus, the preferred cytotoxic activity of the modular antibodies according to the invention is a biological cytotoxic activity, which usually is immunostimulatory, leading to effective cytolysis.

The modular antibody according to the invention may specifically bind to any kind of binding molecules or structures, in particular to antigens, proteinaceous molecules, proteins, peptides, polypeptides, nucleic acids, glycans, carbohydrates, lipids, organic molecules, in particular small organic molecules, anorganic molecules, or combinations or fusions thereof, including PEG, prodrugs or drugs. The preferred modular antibody according to the invention may comprise at least two loops or loop regions whereby each of the loops or loop regions may specifically bind to different molecules or epitopes.

Preferably the target antigen is selected from cell surface antigens, including receptors, in particular from the group consisting of erbB receptor tyrosine kinases (such as EGFR, HER2, HER3 and HER4, in particular those epitopes of the extracellular domains of such receptors, e.g. the 4D5 epitope), molecules of the TNF-receptor superfamily, such as Apo-1 receptor, TNFR1, TNFR2, nerve growth factor receptor NGFR, CD40, T-cell surface molecules, T-cell receptors, T-cell antigen 0×40, TACI-receptor, BCMA, Apo-3, DR4, DR5, DR6, decoy receptors, such as DcR1, DcR2, CAR1, HVEM, GITR, ZTNFR-5, NTR1, TNFL1 but not limited to these molecules, B-cell surface antigens, such as CD10, CD19, CD20, CD21, CD22, antigens or markers of solid tumors or hematologic cancer cells, cells of lymphoma or leukaemia, other blood cells including blood platelets, but not limited to these molecules.

According to a further preferred embodiment the target antigen is selected from those antigens presented by cells, like epithelial cells, cells of solid tumors, infected cells, blood cells, antigen-presenting cells and mononuclear cells. Those target antigens expressed or overexpressed by cells are preferably targeted, which are selected from the group consisting of tumor associated antigens, in particular EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, allergy related molecules IgE, cKIT and Fc-epsilon-receptor1, IRp60, IL-5 receptor, CCR3, red blood cell receptor (CR1), human serum albumin, mouse serum albumin, rat serum albumin, Fc receptors, like neonatal Fc-gamma-receptor FcRn, Pc-gamma-receptors Pc-gamma RI, Pc-gamma-Rh, Pc-gamma Rill, Pc-alpha-receptors, Pc-epsilon-receptors, fluorescein, lysozyme, toll-like receptor 9, erythropoietin, CD2, CD3, CD3E, CD4, CD11, CD11a, CD14, C016, CD18, CD19, CD20, CD22, CD23, CD25, CD28, CD29, CD30, CD32, CD33 (p67 protein), CD38, CD40, CD40L, CD52, CD54, CD56, CD64, CD80, CD147, GD3, IL-1, IL-1R, IL-2, IL-2R, IL-4, IL-5, IL-6, IL-6R, IL-8, IL-12, IL-15, IL-17, IL-18, IL-23, LIE, CSM, interferon alpha, interferon beta, interferon gamma; TNF-alpha, TNFbeta2, TNFalpha, TNFalphabeta, TNF-R1, TNF-RII, FasL, CD27L, CD30L, 4-1BBL, TRAIL, RANKL, TWEAK, APRIL, BAFF, LIGHT, VEG1, OX4OL, TRAIL Receptor-1, A1 Adenosine Receptor, Lymphotoxin Beta Receptor, TACI, BAFF-R, EPO; LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, GM-CSF, M-CSF, RANKL, VLA-1, VLA-4, L-selectin, anti-Id, E-selectin, HLA, HLA-DR, CTLA-4, T cell receptor, B7-1, 87-2, VNRintegrin, TGEbeta1, TGFbeta2, eotaxin1, BLyS (B-lymphocyte Stimulator), complement C5, IgE, IgA, IgD, IgM, IgG, factor VII, CBL, NCA 90, EGFR (ErbB-1), Her2/neu (ErbB2), Her3 (ErbB-3), Her4 (ErbB4), Tissue Factor, VEGF, VEGFR, endothelin receptor, VLA-4, carbohydrates such as blood group antigens and related carbohydrates, Galili-Glycosylation, Gastrin, Gastrin receptors, tumor associated carbohydrates, Hapten NP-cap or NIP-cap, T cell receptor alpha/beta, E-selectin, P-glycoprotein, MRP3, MRP5, glutathione-S-transferase pi (multi drug resistance proteins), alpha-granule membrane protein (GMP) 140, digoxin, placental alkaline phosphatase (PLAP) and testicular PLAP-like alkaline phosphatase, transferrin receptor, Heparanase I, human cardiac myosin, Glycoprotein IIb/IIIa (GPIIb/IIIa), human cytomegalovirus (HCMV) gH envelope glycoprotein, HIV gp120, HCMV, respiratory syncital virus RSV F, RSVF Fgp, VNRintegrin, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, *Clostridium perfringens* toxin and fragments thereof.

Preferred modular antibodies according to the invention are binding said target antigen with a high affinity, in particular with a high on and/or a low off rate, or a high avidity of binding. Usually a binder is considered a high affinity binder with a Kd of <$10^{-9}$ M. Medium affinity binders with a Kd of less than $10^{-6}$ up to $10^{-9}$ M may be provided according to the invention as well, preferably in conjunction with an affinity maturation process.

Affinity maturation is the process by which antibodies with increased affinity for antigen are produced. With structural changes of an antibody, including amino acid mutagenesis or as a consequence of somatic mutation in immunoglobulin gene segments, variants of a binding site to an antigen are produced and selected for greater affinities. Affinity matured modular antibodies may exhibit a several logfold greater affinity than a parent antibody. Single parent antibodies may be subject to affinity maturation. Alternatively pools of modular antibodies with similar binding affinity to the target antigen may be considered as parent structures that are varied to obtain affinity matured single antibodies or affinity matured pools of such antibodies.

The preferred affinity matured variant of a modular antibody according to the invention exhibits at least a 10 fold increase in affinity of binding, preferably at least a 100 fold increase. The affinity maturation may be employed in the course of the selection campaigns employing respective libraries of parent molecules, either with modular antibodies having medium binding affinity to obtain the modular antibody of the invention having the specific target binding property of a Kd<$10^{-8}$ M and/or a potency of IC50<$10^{-8}$ M. Alternatively, the binding potency or affinity may be even more increased by affinity maturation of the modular antibody according to the invention to obtain the high values corresponding to a Kd or IC50 of less than $10^{-9}$ M, preferably less than $10^{-10}$ M or even less than $10^{-11}$ M, most preferred in the picomolar range.

The IC50, also called 50% saturation concentration, is a measure for the binding potency of a modular antibody. It is the molar concentration of a binder, which produces 50% of the maximum possible binding at equilibrium or under saturation. The potency of an antagonist is usually defined by its IC50 value. This can be calculated for a given antagonist by determining the concentration of antagonist needed to elicit half saturation of the maximum binding of an agonist. Elucidating an IC50 value is useful for comparing the potency of antibodies or antibody variants with similar efficacies; however the dose-response curves produced by both drug antagonists must be similar. The lower the IC50, the greater the potency of the antagonist, and the lower the concentration of drug that is required to inhibit the maximum biological response, like effector function or cytotoxic activity. Lower concentrations of drugs may also be associated with fewer side effects.

Usually the affinity of an antibody correlates well with the IC50. The affinity of an antagonist for its binding site (Ki), is understood as its ability to bind to a receptor, which determines the duration of binding and respective agonist activity. Measures to increase the affinity by affinity maturation usually also increase the potency of binding, resulting in the respective reduction of IC50 values in the same range of the Kd values.

The IC50 and Kd values may be determined using the saturation binding assays well-known in the art.

The modular antibody according to the invention is preferably conjugated to a label or reporter molecule, selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Modified immunoglobulins conjugated to labels or reporter molecules may be used, for instance, in assay systems or diagnostic methods.

The modular antibody according to the invention may be conjugated to other molecules which allow the simple detection of said conjugate in, for instance, binding assays (e.g. ELISA) and binding studies.

In a preferred embodiment, antibody variants are screened using one or more cell-based or in vivo assays. For such assays, purified or unpurified modified immunoglobulins are typically added exogenously such that cells are exposed to individual immunoglobulins or pools of immunoglobulins belonging to a library. These assays are typically, but not always, based on the function of the immunoglobulin; that is, the ability of the antibody to bind to its target and mediate some biochemical event, for example effector function, ligand/receptor binding inhibition, apoptosis, and the like. Such assays often involve monitoring the response of cells to the antibody, for example cell survival, cell death, change in cellular morphology, or transcriptional activation such as cellular expression of a natural gene or reporter gene. For example, such assays may measure the ability of antibody variants to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Modular antibodies may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored.

In a preferred embodiment, the DELFIART EuTDA-based cytotoxicity assay (Perkin Elmer, MA) may be used.

Alternatively, dead or damaged target cells may be monitored by measuring the release of one or more natural intracellular components, for example lactate dehydrogenase.

Transcriptional activation may also serve as a method for assaying function in cell-based assays. In this case, response may be monitored by assaying for natural genes or immunoglobulins which may be upregulated, for example the release of certain interleukins may be measured, or alternatively readout may be via a reporter construct. Cell-based assays may also involve the measure of morphological changes of cells as a response to the presence of modular antibodies. Cell types for such assays may be prokaryotic or eukaryotic, and a variety of cell lines that are known in the art may be employed. Alternatively, cell-based screens are performed using cells that have been transformed or transfected with nucleic acids encoding the variants. That is, antibody variants are not added exogenously to the cells. For example, in one embodiment, the cell-based screen utilizes cell surface display. A fusion partner can be employed that enables display of modified immunoglobulins on the surface of cells (Wittrup, 2001, Curr Opin Biotechnol, 12:395-399).

In a preferred embodiment, the immunogenicity of the modular antibodies may be determined experimentally using one or more cell-based assays. In a preferred embodiment, ex vivo T-cell activation assays are used to experimentally quantitate immunogenicity. In this method, antigen presenting cells and naive T cells from matched donors are challenged with a peptide or whole antibody of interest one or more times. Then, T cell activation can be detected using a number of methods, for example by monitoring production of cytokines or measuring uptake of tritiated thymidine. In the most preferred embodiment, interferon gamma production is monitored using Elispot assays.

The biological properties of the modular antibody according to the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic with the appropriate half-life, effector function, apoptotic activity, cytotoxic or cytolytic activity. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the modular antibody according to the invention. Tests of the substances in humans are ultimately required for approval as drugs, and thus of course these experiments are contemplated. Thus the modular antibodies of the present invention may be tested in humans to determine their therapeutic efficacy, toxicity, immunogenicity, pharmacokinetics, and/or other clinical properties. Especially those modular antibodies according to the invention that bind to single cell or a cellular complex through at least two binding motifs, preferably binding of at least three structures cross-linking target cells, would be considered effective in effector activity or preapoptotic or apoptotic activity upon cell targeting and cross-linking. Multivalent binding provides a relatively large association of binding partners, also called cross-linking, which is a prerequisite for apoptosis and cell death.

The modular antibody of the present invention may find use in a wide range of antibody products. In one embodiment the modular antibody of the present invention is used for therapy or prophylaxis, e.g. as an active or passive immunotherapy, for preparative, industrial or analytic use, as a diagnostic, an industrial compound or a research reagent, preferably a therapeutic The modular antibody may find use in an antibody composition that is monoclonal or polyclonal. In a preferred embodiment, the modular antibodies of the present invention are used to capture or kill target cells that bear the target antigen, for example cancer cells. In an alternate embodiment, the modular antibodies of the present invention are used to block, antagonize, or agonize the target antigen, for example by antagonizing a cytokine or cytokine receptor.

In an alternately preferred embodiment, the modular antibodies of the present invention are used to block, antagonize, or agonize growth factors or growth factor receptors and thereby mediate killing the target cells that bear or need the target antigen.

In an alternately preferred embodiment, the modular antibodies of the present invention are used to block, antagonize, or agonize enzymes and substrate of enzymes.

In a preferred embodiment, a modular antibody is administered to a patient to treat a specific disorder. A "patient" for the purposes of the present invention includes both humans and other animals, preferably mammals and most preferably humans. By "specific disorder" herein is meant a disorder that may be ameliorated by the administration of a pharmaceutical composition comprising a modified immunoglobulin of the present invention.

In one embodiment, a modular antibody according to the present invention is the only therapeutically active agent administered to a patient. Alternatively, the modular antibody according the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The modular antibody may be administered concomitantly with one or more other therapeutic regimens. For example, a modular antibody of the present invention may be administered to the patient along with chemotherapy, radiation therapy, or both chemotherapy and radiation therapy. In one embodiment, the modular antibody of the present invention may be administered in conjunction with one or more antibodies, which may or may not comprise a modular antibody of the present invention. In accordance with another embodiment of the invention, the modular antibody of the present invention and one or more other anti-cancer therapies is employed to treat cancer cells ex vivo. It is contemplated that such ex vivo treatment may be useful in bone marrow transplantation and particularly, autologous bone marrow transplantation. It is of course contemplated that the antibodies of the invention can be employed in combination with still other therapeutic techniques such as surgery.

A variety of other therapeutic agents may find use for administration with the modular antibody of the present invention. In one embodiment, the modular antibody is administered with an anti-angiogenic agent, which is a compound that blocks, or interferes to some degree, the development of blood vessels. The anti-angiogenic factor may, for instance, be a small molecule or a protein, for example an antibody, Fc fusion molecule, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the modular antibody is administered with a therapeutic agent that induces or enhances adaptive immune response, for example an antibody that targets CTLA-4. In an alternate embodiment, the modified immunoglobulin is administered with a tyrosine kinase inhibitor, which is a molecule that inhibits to some extent tyrosine kinase activity of a tyrosine kinase. In an alternate embodiment, the modular antibody of the present invention are administered with a cytokine. By "cytokine" as used herein is meant a generic term for proteins released by one cell population that act on another cell as intercellular mediators including chemokines.

Pharmaceutical compositions are contemplated wherein modular antibodies of the present invention and one or more therapeutically active agents are formulated. Stable formulations of the modular antibodies of the present invention are prepared for storage by mixing said immunoglobulin having the desired degree of purity with optional pharmaceutically acceptable carriers, excipients or stabilizers, in the form of lyophilized formulations or aqueous solutions. The formulations to be used for in vivo administration are preferably sterile. This is readily accomplished by filtration through sterile filtration membranes or other methods. The modular antibody and other therapeutically active agents disclosed herein may also be formulated as immunoliposomes, and/or entrapped in microcapsules.

Administration of the pharmaceutical composition comprising a modular antibody of the present invention, preferably in the form of a sterile aqueous solution, may be done in a variety of ways, including, but not limited to, orally, subcutaneously, intravenously, intranasally, intraotically, transdermally, mucosal, topically (e.g., gels, salves, lotions, creams, etc.), intraperitoneally, intramuscularly, intrapulmonary (e.g., $^{AERX}$TM inhalable technology commercially available from Aradigm, or I$_n$h$_{ance}$™ pulmonary delivery system commercially available from Inhale Therapeutics), vaginally, parenterally, rectally, or intraocularly.

A preferred method according to the invention refers to a randomly modified nucleic acid molecule coding for an immunoglobulin, immunoglobulin domain or a part thereof which comprises at least one nucleotide repeating unit within a structural loop coding region having the sequence 5T-NNS-3', 5T-NNN-3', 5'-NNB-3' or 5'-NNK-3'. In some embodiments the modified nucleic acid comprises nucleotide codons selected from the group of TNT, WMT, BMT, RMC, RMG, MRT, SRC, KMT, RST, YMT, MKC, RSA, RRC, NNK, NNN, NNS or any combination thereof (the coding is according to IUPAC).

The modification of the nucleic acid molecule may be performed by introducing synthetic oligonuleotides into a larger segment of nucleic acid or by de novo synthesis of a complete nucleic acid molecule. Synthesis of nucleic acid may be performed with tri-nucleotide building blocks which would reduce the number of nonsense sequence combinations if a subset of amino acids is to be encoded (e.g. Yanez et al. Nucleic Acids Res. (2004) 32:e158; Virnekas at al. Nucleic Acids Res. (1994) 22:5600-5607)

The randomly modified nucleic acid molecule may comprise the above identified repeating units, which code for all known naturally occurring amino acids or a subset thereof. Those libraries that contain modified sequences wherein a specific subset of amino acids are used for modification purposes are called "focused" libraries. The members of such libraries have an increased probability of an amino acid of such a subset at the modified position, which is at least two times higher than usual, preferably at least 3 times or even at least 4 times higher. Such libraries have also a limited or lower number of library members, so that the number of actual library members reaches the number of theoretical library members. In some cases the number of library members of a focused library is not less than $10^3$ times the theoretical number, preferably not less than $10^2$ times, most preferably not less than 10 times.

Usually libraries according to the invention comprise at least 10 fusion proteins or potential binding agents or variants of scaffold proteins, preferably at least 100, more preferred at least 1000, more preferred at least $10^4$, more preferred at least $10^5$, more preferred at least $10^6$, more preferred at least $10^7$, more preferred at least $10^8$, more preferred at least 10% more preferred at least $10^{10}$, more preferred at least $10^{11}$, up to $10^{12}$, in cases of in vitro display methods, such as ribosomal display, even higher number are feasible.

Various alternatives are available for the manufacture of the gene encoding the randomized library. It is possible to produce the DNA by a completely synthetic approach, in which the sequence is divided into overlapping fragments which are subsequently prepared as synthetic oligonucleotides. These oligonucleotides are mixed together, and annealed to each other by first heating to ca. 100° C. and then slowly cooling down to ambient temperature. After this annealing step, the synthetically assembled gene can be either cloned directly, or it can be amplified by PCR prior to cloning.

Alternatively, other methods for site directed mutagenesis can be employed for generation of the library insert, such as the Kunkel method (Kunkel TA. Rapid and efficient site-specific mutagenesis without phenotypic selection. Proc Natl Acad Sci USA. 1985 January; 82(2):488-92) or the DpnI method (Weiner M P, Costa G L, Schoettlin W, Cline J, Mathur E, Bauer J C. Site-directed mutagenesis of double-stranded DNA by the polymerase chain reaction. Gene. 1994 Dec. 30; 151(1-2):119-23.).

For various purposes, it may be advantageous to introduce silent mutations into the sequence encoding the library insert. For example, restriction sites can be introduced which facilitate cloning or modular exchange of parts of the sequence. Another example for the introduction of silent mutations is the ability to "mark" libraries, that means to give them a specific codon at a selected position, allowing them (or selected clones derived from them) e.g. to be recognized during subsequent steps, in which for example different libraries with different characteristics can be mixed together and used as a mixture in the selection or panning procedure.

The invention also provides a method of producing an oligomer of modular antibody domains binding to a target comprising the steps of:

providing a library of oligomers of modular antibody domains produced according to the inventive method as described contacting said library with said target in the presence of a scaffold ligand, selecting a library member binding to said target in the presence of a scaffold ligand, and manufacturing a preparation of the functional oligomer.

The scaffold ligand can be selected from the group consisting of an effector molecule, FcRn, Protein A and CDR target. As an example, the effector molecule can be selected from the group consisting of CD64, CD32, CD16, Fc receptors.

The oligomers can be dimers selected from the group of VH/VL, CH1/CL, CH2/CH2, CH3/CH3, Fc and Fab, or single chains thereof The method according to the invention can provide a library containing at least $10^2$ independent clones expressing functional oligomers of modular antibody domains or variants thereof.

Libraries as used according to the invention preferably comprise at least $10^2$ library members, more preferred at least $10^3$, more preferred at least $10^4$, more preferred at least $10^5$, more preferred at least $10^6$ librarymembers, more preferred at least $10^7$, more preferred at least $10^8$, more preferred at least 10% more preferred at least $10_{10}$, more preferred at least $10^{11}$, up to $10^{12}$ members of a library, preferably derived from a parent molecule, which is a functional modular antibody as a scaffold containing at least one specific function or binding moiety, and derivatives thereof to engineer a new binding site apart from the original functional binding region of said parent moiety.

Usually the libraries according to the invention further contain variants of the modular antibody, resulting from mutagenesis or randomization techniques. These variants include inactive or non-functional antibodies. Thus, it is preferred that any such libraries be screened with the appropriate assay for determining the functional effect. Preferred libraries, according to the invention, comprise at least $10^2$ variants of such modular antibodies, more preferred at least $10^3$, more preferred at least $10^4$, more preferred at least $10^5$, more preferred at least $10^6$, more preferred at least $10^7$, more preferred at least $10^8$, more preferred at least 10% more preferred at least $10^{10}$, more preferred at least $10^{11}$, up to $10^{12}$ variants or higher to provide a highly diverse repertoire of antibodies for selecting the best suitable binders. Any such synthetic libraries may be generated using mutagenesis methods as disclosed herein.

Preferably the library is a yeast library and the yeast host cell exhibits at the surface of the cell the oligomers, or monomers that form oligomers, with the biological activity. The yeast host cell is preferably selected from the genera *Saccharomyces, Pichia, Hansenula, Schizisaccharomyces, Kluyveromyces, Yarrowia* and *Candida*. Most preferred, the host cell is *Pichia* or *Saccharomyces cerevisiae*.

The invention further provides a high quality library containing at least $10^2$ independent clones of functional dimers of modular antibody domains or variants thereof that are binding to a target and to a scaffold ligand. The target can be a ligand binding to a parent molecule subject to amino acid variation. The parent molecule can be a functional oligomer, in particular a functional Pc or a functional Fab, or part thereof.

As is well-known in the art, there is a variety of display and selection technologies that may be used for the identification and isolation of proteins with certain binding characteristics and affinities, including, for example, display technologies such as cellular and non-cellular, in particular mobilized display systems. Among the cellular systems the phage display, virus display, yeast or other eukaryotic cell display, such as mammalian or insect cell display, may be used. Mobilized systems are relating to display systems in the soluble form, such as in vitro display systems, among them ribosome display, mRNA display or nucleic acid display.

Methods for production and screening of antibody variants are well-known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76.

A library according to the invention may be designed as a dedicated library that contains at least 50% specific formats, preferably at least 60%, more preferred at least 70%, more preferred at least 80%, more preferred at least 90%, or those that mainly consist of specific antibody formats. Such a preferred library mainly contains the same kind of library members having similar structural features. Specific antibody formats are preferred, such that the preferred library according to the invention is selected from the group consisting of a VH library, VHH library, Vkappa library, Vlambda library, Fab library, a CH1/CL library, an Fe library and a CH3 library. Libraries characterized by the content of composite molecules containing more than one antibody domains, such as an IgG library or Fe library are specially preferred. Other preferred libraries are those containing T-cell receptors, forming T-cell receptor libraries. Further preferred libraries are epitope or peptide libraries, wherein the fusion protein comprises a molecule with a variant of an epitope, also enabling the selection of competitive molecules having similar binding function, but different functionality. Exemplary is a TNFalpha library, wherein trimers of the TNFalpha fusion protein are displayed by a single genetic package.

Another important aspect of the invention is that each potential binding domain remains physically associated with the particular DNA or RNA molecule which encodes it, and in addition, the fusion proteins oligomerize at the surface of a genetic package to present the binding polypeptide in the native and functional oligomeric structure. Once successful binding domains are identified, one may readily obtain the gene for expression, recombination or further engineering purposes. The form that this association takes is a "replicable genetic package", such as a virus, cell or spore which replicates and expresses the binding domain-encoding gene, and transports the binding domain to its outer surface. Another form is an in-vitro replicable genetic package such as ribosomes that link coding RNA with the translated protein. In ribosome display the genetic material is replicated by enzymatic amplification with polymerases.

Those cells or viruses or nucleic acid bearing the binding agents which recognize the target molecule are isolated and, if necessary, amplified. The genetic package preferably is M13 phage, and the protein includes the outer surface transport signal of the M13 gene III protein.

Preferably in the method of this invention the vector or plasmid of the genetic package is under tight control of the transcription regulatory element, and the culturing conditions are adjusted so that the amount or number of vector or phagemid particles displaying less than two copies of the fusion protein on the surface of the particle is less than about 20%. More preferably, the amount of vector or phagemid particles displaying less than two copies of the fusion protein is less than 10% the amount of particles displaying one or more copies of the fusion protein. Most preferably the amount is less than 1%.

The expression vector preferably used according to the invention is capable of expressing a binding polypeptide, and may be produced as follows: First a binding polypeptide gene library is synthesized by introducing a plurality of polynucleotides encoding different binding sequences. The plurality of polynucleotides may be synthesized in an appropriate amount to be joined in operable combination into a vector that can be propagated to express a fusion protein of said binding polypeptide. Alternatively the plurality of polynucleotides can also be amplified by polymerase chain reaction to obtain enough material for expression. However, this would only be advantageous if the binding polypeptide would be encoded by a large polynucleotide sequence, e.g. longer than 200 base pairs or sometimes longer than 300 base pairs. Thus, a diverse synthetic library is preferably formed, ready for selecting from said diverse library at least one expression vector capable of producing binding polypeptides having the desired preselected function and binding property, such as specificity.

The foregoing description will be more fully understood with reference to the following examples. Such examples are, however, merely representative of methods of practicing one or more embodiments of the present invention and should not be read as limiting the scope of invention.

EXAMPLES

Example 1

Construction of the Non-Focussed Fcab Library (Fcab01) and Phage Surface Display The crystal structure of an IgG1 Fc fragment, which is published in the Brookhaven Database as entry 10Q0.pdb was used to aid in the design of the Fcab library.

The sequence which was used as the basis for construction of the Fcab library is given in SEQ ID No. 1. In this sequence, the first amino acid corresponds to Glu 216 of human IgG1 (EU numbering; according to the IMGT database (http://imgt.cines.fr/textes/IMGTrepertoire/Proteins/protein/human/IGH/IGHC/Hu_IGHCallgenes.html; lookup 2007 06 25), it is the first residue of the human IgG1 hinge region, which is given as: (E) PKSCDKTHTCPPCP) of the heavy constant chain hinge region of human IgG1.) The second-last residue of SEQ ID No. 1 corresponds to Gly 446 of human IgG1 (EU numbering; IMGT: residue number 129 of the CH3 domain of human IgG1).

After detailed analysis of the structure of logo.pdb and by visual inspection of the residues forming the loops which connect the beta strands, it was decided to randomize residues 144, 145 and 146, which are part of the loop connecting beta strand A-B as well as 198, 199, 200, 203 and 204, which are part of the loop connecting beta strand E-F of SEQ ID No.1. In addition to the mutated residues, 5 residues were inserted at residue number 198 of SEQ ID No.1. In SEQ ID No. 2, the sequence of the library insert of library Fcab01 is given in which all randomized residue positions as well as the 5 inserted residues are designated with the letter X.

The engineered gene was produced by a series of PCR reactions using degenerate primers followed by ligation of the resulting PCR products. To facilitate ligation, some of the codons of the nucleotide sequence coding for SEQ ID No. 1 were modified to produce restriction sites without changing the amino acid sequences (silent mutations). For insertion into the cloning vector pHEN1 (Nucleic Acids Res. 1991 Aug. 11; 19(15):4133-7. Multi-subunit proteins on the surface of filamentous phage: methodologies for displaying antibody (Fab) heavy and light chains. Hoogenboom H R, Griffiths A D, Johnson K S, Chiswell D J, Hudson P, Winter G.) in frame with the pelB secretion signal, the NcoI restriction site close to the 3' end of the pelB secretion signal was used. For the randomized residues, the codon NNS (IUPAC code, where S means nucleotides C and G) was chosen which encodes all 20 naturally occurring amino acids, but avoids 2 out of 3 stop codons. Other codons such as for example the NNB (B meaning nucleotides T, C and G) can also be used. The engineered sequence is given as a nucleotide sequence in SEQ ID No. 3. This sequence also includes the restriction sites used for cloning into the phagmid display vector pHEN1, namely an NcoI site at the 5' end and a NotI site at the 3' end.

The sequences of the PCR primers used for assembly of the mutated CH3 domain are given in SEQ ID No. 4 through SEQ ID No. 9.

SEQ ID No. 4 (PCR primer EPKSNCO) ccatggccgagc-ccaaatcttgtgacaaaactc

SEQ ID No. 5 (PCR primer CH3LSAC) agtcgagctcgt-cacgggatgggggcaggg

SEQ ID No. 6 (PCR primer CH3CSAC) gtac-gagctcnnsnnsnnscaagtcagcctgacctgcctgg

SEQ ID No. 7 (PCR primer CH3CHIN) tgccaagcttgctgta-gaggaagaaggagccg

SEQ ID No. 8 (PCR primer CH3RHIN) tgccaagettaccgt-gnnsnnsnnsaggtggnnsnnsgggaacgtcttctcatgctccg SEQ ID No. 9 (PCR primer CH3RNOT) agttgeggccgctttac-coggagacagggagag FIG. 1 shows a schematic presentation of the PCR fragments generated for assembly of the mutated gene, and the primers used therefore.

cDNA of the heavy chain of the human monoclonal antibody 3D6 (Felgenhauer M, Kohl J, RUker F. Nucleotide sequences of the cDNAs encoding the V-regions of H- and L-chains of a human mono-clonal antibody specific to HIV-1-gp41. Nucleic Acids Res. 1990 Aug. 25; 18(16): 4927.) was used as template for the PCR reactions. The 3 PCR products were digested with Sac' and/or HindIII respectively and ligated together. The ligation product was further digested with NcoI and NotI and ligated into the surface display phagmid vector pHEN1, which had previously been digested with NcoI and NotI. The ligation product was then transformed into E. coli by electroporation. A number of selected clones were controlled by restriction analysis and by DNA sequencing and were found to contain the insert as planned, including the correctly inserted randomized sequences. For the following steps of phage preparation, standard protocols were followed. Briefly, the ligation mixture was transformed into E. coli TG1 cells by electroporation. Subsequently, phage particles were rescued from E. coli TG1 cells with helper phage M13-K07. Phage particles were then precipitated from culture supernatant with PEG/NaCl in 2 steps, dissolved in water and used for selection by panning or, alternatively, they were stored at minus 80° C.

Example 2

Construction of the Focussed Fcab Library (Fcab02) and Phage Surface Display

As described in example 1, an Fcab library was prepared in which the randomized library positions are fully randomized, i.e. they are encoded by a codon such as NNS, NNB, NNK, NNN or others are used.

For clarity, the meaning of the letters such as N, B, S or K is defined by the IUPAC nucleotide ambiguity code, which is given in the following table:

TABLE 1

IUPAC nucleotide ambiguity code

| Symbol | Meaning | Nucleic Acid |
| --- | --- | --- |
| A | A | Adenine |
| C | C | Cytosine |
| G | G | Guanine |
| T |  | Thymine |
| U |  | Uracil |
| M | A or C |  |
| R | A or G |  |
| W | A or T |  |
| S | C or G |  |
| Y | C or T |  |
| K | G or T |  |
| V | A or C or G |  |
| H | A or C or T |  |
| D | A or G or T |  |
| B | C or G or T |  |
| X | G or A or T or C |  |
| N | G or A or T or C |  |

Source: Nomenclature for incompletely specified bases in nucleic acid sequences: recommendations 1984. A Cornish-Bowden, Nucleic Acids Res. 1985 May 10; 13(9): 3021-3030.

These codons given above are designed such that all 20 amino acids are encoded by them. It may be preferable to choose subsets out of the possible amino acids. Examples can be found in the literature (Fellouse F A, Li B, Compaan D M, Peden A A, Hymowitz S G, Sidhu S S. Molecular recognition by a binary code. J Mol Biol. 2005 May 20; 348(5):1153-62. Epub 2005 Apr. 1.; Fellouse F A, Wiesmann C, Sidhu S S. Synthetic antibodies from a four-amino-acid code: a dominant role for tyrosine in antigen recognition. Proc Natl Acad Sci USA. 2004 Aug. 24; 101(34):12467-72. Epub 2004 Aug. 11.). Focused libraries which for example allow for only 4 different amino acid types can be constructed e.g. by employing the codon KMT, which codes for the amino acids Ser, Tyr, Ala and Asp.

A focused Fcab library, designated Fcab02, has been constructed in the same way as described in example 1, except that the NNS codons were replaced by KMT codons. Therefore, the letter "X" in SEQ ID No. 2 now means "S, Y, A and D" (Ser, Tyr, Ala and Asp) in order to describe the focused library Fcab02

Example 3

Construction of a Phage Surface Display Library with Additional Amino Acid Residues Between the Library Insert (Binding Partner) and p3

In order to investigate accessibility of the potential binding site of the displayed protein a binding assay is performed: the phage suspension is reacted with anti-myc mAb 9E10-coated microplates (or immunotubes). After washing, the bound phages are detected with anti-M13-enzyme conjugate. As a control, helper phage—which does not display the protein fusion and the myc-tag is reacted with the plates. Other controls are reaction of phages with non-coated plates and reaction of phages with antiserum recognizing the p3-fusion partner of the phages.

Ideally, the anti-myc-reactivity of phages displaying the p3-fusion protein should give very clear ELISA readouts whereas helper phage reactions to anti-myc-mAb should not be above background (non-coated plates). The structure of a CH3 dimer displayed at the surface of an M13 phage through binding to protein III as an anchor is such, that each CH3 is anchored to protein III using various linker length and compositions. Thus, the CH3 dimer is preferably displayed by two anchors.

Linker Optimization:

The linker between the protein to be displayed and the anchor protein of the genetic package (in case of filamentous phage e.g. p3, p8, pX, pIX, pVII) is especially important if the potential binding site of the displayed molecule is in spatial vicinity of the phage particle. In antibody libraries utilizing variable domains and antigen binding sites formed by CDR-loops and display of the library members as amino-terminal fusion to p3 the potential antigen binding site is directed away from the phage particle. Therefore, the linker structure between library members and the phage coat protein is less important. Engineering the bottom loops of immunoglobulin domains and performing phage display may however be an inefficient process and decrease yields of antigen binding clones or even preclude it. Varying the linker between a library member protein and its fusion partner on the surface can solve or may at least reduce this problem.

In order to select for optimal linker sequences (in terms of length and flexibility as well as stability) a library of linkers can be prepared in which the anchor protein at the surface of the genetic replicable package is fused to a known binding protein which is for sterical reasons notoriously difficult to select for.

This library of sequences can be varied in length and amino acid content.

Selection methods of the linker library for optimal linkers depend on the application but basically it should be for selecting all properties one wishes to have in a certain methodology. Enrichment against a difficult to select for antigen may yield linker sequences which allow library members a good access to the antigen. Incubation in protease solutions or under other harsh conditions or frequent passaging through host cells under proteolytic conditions (e.g. old microbial cultures) may be an appropriate selection for stable display linkers.

A library of linkers may be produced by any well known library technology. Synthetic linker sequence lengths may vary between 10-500 amino acids. Alternatively, linker can be complete proteins known to be of flexible nature.

Linker Optimization FcabO1:

As an example, library FcabO1 (as described in example 1) can be used. Originally, this library is cloned in the phagmid display vecor pHEN1, using NcoI and NotI restriction sites. When cloned in this manner, 18 amino acid residues are in between the C-terminal amino acid residue of the FcabO1 library insert and the N-terminal amino acid residue of phage M13 p3. The sequence of this junction region is given in SEQ ID No. 10 SPGKAAAEQKLISEED-LNGAATVES—and is explained as follows: the first 4 residues, SPGK (SEQ ID No. 83), are the 4 C-terminal residues of the FcabO1 library insert, followed by the amino acid sequence AAA, which is the amino acid residues encoded by the NotI restriction site, followed by the sequence EQKLISEEDL (SEQ ID No. 84), which is the myc epitope, followed by NGAA (SEQ ID No. 85), after which there is an amber stop codon, which is translated to Glutamine (Q) in amber suppressor strains of E. coli such as TG1.

The C-terminal 4 residues of SEQ ID No. 10, TVES (SEQ ID No. 86), are the N-terminal 4 residues of phage M13 p3 as present in the vector pHEN1.

In order to construct a phage which displays an Fcab insert with an increased distance between the Fcab (the binding partner) and the body of the phage (the genetic package), 5 additional residues were inserted at the C-terminus of the Fcab insert FcabRGD4, directly upstream of the NotI cloning site, resulting in the clone FcabRGD4L. FcabRGD4 is an Fcab that has an integrin-binding RGD motif inserted in the EF-loop of the CH3 domain and which binds to αvβ-integrin in ELISA. As an increased-length linker sequence, the amino acid sequence EGGGS (SEQ ID No.89), which appears 8 times in the phage M13 p3 sequence was used. The resulting amino acid sequence of FcabRGD4L as expressed after cloning in pHEN1 is given in SEQ ID No.11. In SEQ ID No.11, amino acid residues 198-204 represent the RGD motif, amino acid residue 237 is the C-terminal residue of the Fcab insert, residues 238-242 represent the inserted linker sequence (which is the difference to unmodified pHEN1), which is followed by myc tag, amber stop codon and the p3 sequence.

For cloning of the construct, the FcabRGD4 sequence was amplified from pHENFcabRGD4 (SEQ ID No. 12) using PCR primers EPKSNCO (SEQ ID No. 4) and CH3rlink actagcggccgcagagccaccaccctecttacccggagacagggagag (SEQ ID No. 13) and cloned via NcoI and NotI restriction sites into the vector pHEN1. The resulting vector, pHENFcabRGD4L (SEQ ID. No. 14) has the additional linker sequence at nucleotide positions 3057-3071.

The two phagemid vectors, pHENFcabRGD4 and pHENFcabRGD4L were transformed into *E. coli* TG1. Subsequently, phage particles were rescued from *E. coli* TG1 cells with helper phage M13-1K07. Phage particles were then precipitated from culture supernatant with PEG/NaCl in 2 steps, dissolved in water and used for ELISA.

Phage ELISA was performed as follows: The phage suspension is reacted with aV133-integrin-coated microplates (or immunotubes). After washing, the bound phages are detected with anti-M13-enzyme conjugate. As controls, helper phage—which does not display the protein fusion and the myc-tag is reacted with the plates as well as phage particles carrying wtFcab on their surface. Other controls are reaction of phages with non-coated plates and reaction of phages with antiserum recognizing the Fcab-fusion partner of the phages. Phage particles with the increased-length linker resulting from pHENFcabRGD4L react more readily with avp3 integrin than phage particles with the original linker as contained in pHENFcabRGD4, and therefore give a stronger signal in ELISA.

Phage selections can be performed in which phage particles with wtFcab are mixed with small amounts of phage particles carrying either FcabRGD4 or FcabRGD4L. After several (typically 3-5) rounds of panning, preferentially phages displaying FcabRGD4L are selected.

Example 4

Fcab Library Design ("Fcab" is a registered trademark of f-star Biotechnologische Forschungs- and Entwicklungsges.m.b.H.)

Design of Fcab Libraries (illustrated in FIG. 2): amino acid positions in non CDR-loops of CH3 constant domains of antibodies are considered for randomization. Especially loops A-B, C-D and E-F are considered as they are on one side of the domain. Some of the design criteria for randomization at a certain position are described herein.

Amino acids frequently involved in antigen antibody interactions are described herein to be included in a focused library. Here the amino acids Ala, Asp, Ser and Tyr are used to design the focused library.

Libraries with restricted amino acid utilization have been shown to be sufficient to generate binders against virtually any antigen (Sidhu & Fellhouse, NATURE CHEMICAL BIOLOGY VOLUME 2 page 682ff; Koide et al PNAS, volume 104 p6632-6637). The advantage of such restricted (or focused) libraries is that they can be covered completely by current technologies. Ideally, the amino acid utilization reflects a natural amino acid utilization of ligand receptor binding. However, even libraries utilizing only 2 amino acids (Tyrosine and Serine) have been reported to yield good selection results (in terms of frequency of binders against different binders and in terms of affinity).

Loop Flexibility:

Certain loop structures may be required by the scaffold protein in order to keep the overall natural structure. Randomizing many amino acid positions in loops and even elongation of loops may be facilitated by building certain sequences either on one or on both sides of the randomized positions. These sequences may be flexible sequences in order to allow to compensate for any tensions with certain library sequences in such a position.

TABLE 2

Exemplary Fcabm libraries, focused and non-focused

| | # of randomized positions | Theoretical diversity on amino acid level | Number of independent bacterial clones |
|---|---|---|---|
| FcabO1 | 13 | $8.2 \times 10^{16}$ | $0.6 \times 10^9$ |
| Fcab02 | 13, focused | $6.7 \times 10^7$ | $0.6 \times 10^9$ |
| Fcab03 | 13 | $8.2 \times 10^{16}$ | $1.0 \times 10^9$ |
| Fcab04 | 13, focused | $6.7 \times 10^7$ | $0.8 \times 10^9$ |
| Fcab05 | 15 | $1.3 \times 10^{18}$ | $0.8 \times 10^9$ |
| Fcab06 | 15, focused | $1.3 \times 10^9$ | $1.0 \times 10^9$ |

FcabO1 library is described in the examples above. The sequence space of the focused library designs Fcab02, Fcab04 and Fcab06 are covered by the actual bacterial library sizes of approximately 10e9. In contrast, the completely randomized libraries Fcab01, Fcab03 and Fcab05 are actually grossly underrepresented.

Example 5

Cloning of Yeast Display Libraries by Homologous Recombination

Vector pYD1 (Invitrogen) is used as the basic vector. The vector is modified as follows, in order to remove an XhoI site: pYD1 is cleaved with XhoI, treated with Klenow fragment of DNA polymerase and religated. The resulting sequence is given in pYD1dX (SEQ ID No. 15).

pYD1dX contains a unique BamEI restriction site at position 921/925 and a unique NotI restriction site at position 963/967. It is opened with these two restriction enzymes.

An insert encoding CH1-hinge-CH2-CH3 from human IgG1 is prepared by PCR from cDNA encoding the heavy chain of a human IgG1 monoclonal antibody. In this insert, a point mutation is introduced using standard procedures to mutate the C-terminal Cystein residue of the CH1 domain to a Serine. The insert is amplified using PCR primers that attached a BamHI and a Not restriction site to both ends respectively. These restriction sites are then used for cloning the insert into pYD1dX to yield the display vector pYD1dXFc (SEQ Id No. 16). The mutated codon at the C-terminus of the CH1 domain (Cys to Ser) is at positions 1233-1235 in the sequence pYD1DxFc. The stop codon of the insert is at position 1917/1919.

This vector is used as a positive control for the display of human CH1-hinge-CH2-CH3 on the surface of yeast and as a starting point for the construction of the vector pYD1CH12 (see below).

Cloning of Libraries

Cloning of libraries in which mutations are introduced into structural loops of CH3 domains is performed in yeast by homologous recombination (gap repair). For this purpose, a recipient vector is prepared that lacks the CH3 domain: pYD1dXFc is cleaved with XhoI (position 1603/1607) and NotI (position 1921/1925), the large fragment is prepared by preparative gel electrophoresis, treated with Klenow fragment of DNA polymerase and re-ligated. This procedure reconstitutes a unique XhoI site (position 1603/1607) and yielded vector pYD1CH12 (SEQ ID No. 17). pYD1CH12 is subsequently cleaved with XhoI and is used as recipient vector for gap repair in yeast.

As a source of insert, Fcab libraries Fcab01 (SEQ ID No. 18), Fcab02 (SEQ ID No. 19), Fcab03 (SEQ ID No. 20), Fcab04 (SEQ ID No. 21), Fcab05 (SEQ ID No. 22) and Fcab06 (SEQ ID No. 23) are used. These libraries are prepared by standard DNA synthesis, and contain randomized residues as well as inserted residues in the AB loop (between residues 359 and 361 (EU numbering)) as well as in the EF loop (between residues 413 and 419 (EU numbering)) of the CH3 domain of human IgG1. From this synthetic DNA, the insert for gap repair in yeast is amplified by PCR using PCR primer pair gapch35 caacaaggccctgcct-gccccat cgagaagaccatctccaaggccaagggccagcctcgagaac-cacaggtgtacaccctgccc (SEQ ID No. 24) and gapfcs3 gagac-cgaggagagggttagggataggcttacct tcgaagggccctctagactcgatcgagegggccgctcatttacccggagaca-gggagagctc ttc (SEQ ID No. 25). 100 pg of XhoI cleaved vector pYD1CH12 and 100 pg of insert are mixed and transformed in Saccharomyces strain EBY100 (Invitrogen) using the Lithium acetate procedure according to the following protocol, which is upscaled by a factor 100 to transform the required amount of cells and of DNA. Briefly, for a single transformation of 1 pg vector DNA and 1 pg insert DNA, 10 ml of YPD (2% peptone, 2% dextrose (D-glucose)) are inoculated with a yeast colony and shaken overnight at 30° C. The 0D600 of the overnight culture is determined and the culture diluted to an 0D600 of 0.4 in 50 ml of YPD and grown for an additional 6 hours. Cells are pelleted at 2500 rpm and resuspended in 40 ml distilled water. Cells are pelleted again at 2500 rpm and resuspended in 100 mM LiAc, followed by incubation at 30° C. for 30 minutes. 1 pg vector DNA, 1 pg insert and 50 pl denatured sheared salmon sperm DNA (2 mg/ml) are mixed with 300 pl of the yeast suspension. 700 pl of a solution of 200 mM Li-acetate and 40% PEG-3350 are added and mixed with the yeast/DNA suspension, followed by incubation at 30° C. for 30 minutes. 88 pl DMSO are added, mixed and the mixture is incubated at 42° C. for 40 minutes, followed by centrifugation in a microcentrifuge for 10 seconds. The supernatant is then removed, the cell pellet is resuspended in 1 ml distilled water. The pellet is then resuspended in 50-100 pl TE and plated on minimal dextrose plates containing leucine (10 g/l yeast nitrogen base, 20 g/l dextrose, 0.1 g/l leucine, 15 g/l agar). After incubation of the plates at 30° C. for 2 to 4 days single colonies appeared that are subsequently harvested.

Cultivation—Induction

The harvested yeast libraries (yFcab libaries) are inoculated in 10 ml SD-CAA medium (10 g/l yeast nitrogen base, 10 g/l casamino acids, and 20 g/l dextrose, 0.1 g/l leucine, 9.67 g/l NaH2PO4-2H20 and 10.19 g/l Na2HPO4.7H20) and grown on a shaker at 250 rpm at 28° C. for 6-8 hours. The 0D600 of the culture is determined, and the culture is diluted to an 0D600 of 0.2, and grown under the same conditions until an 0D600 of 1-2 is reached. Cells are harvested by centrifugation (3000 rpm 5 min/4° C.) and resuspended in induction medium SG/R-CAA (10 g/l yeast nitrogen base, 10 g/l casamino acids, and 20 g/l galactose, 10 g/l raffinose, 0.1 g/l leucine, 9.67 g/l NaH2PO4-2H20 and 10.19 g/l Na2HPO4-7H20). Cultures are induced by incubation for 2 days on a shaker at 250 rpm at 20° C. and subsequently analysed and sorted.

Quality Control of yFcab Libraries.

yFcab libraries are tested for their expression level and quality of expressed Fcab's two days after induction with SD-CAA medium. The expression level is tested using a polyclonal anti human IgG-Fc antiserum (Sigma). For this purpose 0.5×10e6 library cells are diluted in 1 ml staining buffer (SB), which comprises PBS with 2% BSA. Cells are pelleted and stained with 100 pl SB containing 1/2000 diluted anti human IgG-Pc-PE antiserum (Sigma) for 30 min on ice, washed twice with SB and subsequently analyzed in the FACS. In general 70%-80% of all cells in each library express Fcabs on their cell surface. To test correct folding of Fcabs, staining with Protein A is performed. Again 0.5×10e6 library cells are diluted in 1 ml staining buffer SB, cells are pelleted and stained with 100 pl SB containing 1 pg/ml Prot-A-FITC (Fluka) for 30' on ice, washed twice with SB and subsequently analyzed in the FACS. In general, the yFcab libraries as described above show >40% Prot A positive cells. In order to test whether the Fcabs are expressed as dimers on the surface of the cells a staining with human CD64 is performed. The affinity of CD64 is too low for efficient monomeric binding therefore CD64 complexes with dimers are used. For this purpose e.g. 1ug recombinant CD64 from R&D Systems (containing a HIS-tag) is mixed with 1 ug anti Penta HIS-alexafluor 488 (from Qiagen) in 1 ml SB (total volume). yFcab libraries are tested for binding to CD64 by incubating the 5×10e5 cells with 100 pl of the complex-mixture for 30 minutes on ice, as control the cells are incubated with equivalent of the anti HIS-alexafluor 488 alone (1/200 dilution in SB). After incubation the cells are washed twice with ice cold SB and analysed in the FACS. In general >50% of all cells in each library express dimeric Fcabs on their cell surface.

Biotinylation of Antigen (her2)

Recombinant antigen e.g. Her2 (Bendermedsystems) was done with he EZ link system of Pierce according to the manufacturers instruction. In short, the antigen is dialyzed against PBS, diluted to 1 mg/ml in PBS and mixed with 10 m'l sulfo-LC-LC− biotin (EZ link, Pierce), which was pre-disolved in water. The final ratio between antigen and biotin is 1:3 and the mixture is incubated at room temperature from 30'. Afterwards the mixture is "dialyzed" against PBS using Vivaspin MWC03000 (Sartorius) columns (5×8', 4000 rpm). Finally the concentration of the biotinylated antigen (Her2) is tested by HPLC and aliquots are stored at −20° C.

The quality of the biotinylated antigen is tested by ELISA. First the plates are coated with an anti-Her2 antibody (e.g. Herceptin) at 10 pg/ml in PBS, 100 pl/well overnight at 4° C., after this the plate is washed 3× with washing buffer (WB)(PBS+0.05% Tween20) and blocked by blocking buffer (BB) (PBS+2% BSA) 1 h at room temperature. After 3× washing with WB, different concentrations of Her2-biotin are added in 100 pl/well BB for 1 h at room temperature, followed by 3× washing with WB. Finally the plate is incubated with 1:25000 streptavidin-HRP (GE healthcare) in BB for 1 h at room temperature and washed 3× with WB. Colour is developed by adding 100 pl/well of the substrate TMB (Sigma) after ~10 minutes the reaction is stopped by adding 100 pl/well of 30% H2SO4. The results is analysed with an ELISA reader at 450-630 nm.

Example 6

Production of Antigen Specific (her2) Fcabs

Selection of antigen specific (Her2) Fcabs using FACS
First Selection Round:
Two days before FACSorting a yeast library containing 2.5×10e 8 individual Fcab clones is induced with SG/R-CAA medium to express the Fcabs on their cell surface as described above. After two days, the amount of cells covering e.g. 10 times the library (=2.5×10e9) is incubated for 30 minutes on ice with 500 nM biotinylated antigen (Her2) in 20l SB. Then the cells are washed once with cold SB and subsequently incubated for 30' on ice with streptavidin-PE (from R&D systems) diluted 1 100 in SB. The cells are washed twice with ice cold SB and diluted to an end concentration of 1×10e9 cells/ml. Control stainings with 5×10e6 cell/ml in 100 pl are made with streptavidin-PE only, in the absence of antigen. Both the complete library and the control stainings are analysed in e.g. a FACS ARIA from BD. To set the gates for sorting the control cells are used. First a FSC/SSC gate (G1) is set to identify healthy yeast cells, from G1 a FSC-width versus FSC-area plot is made and only non-aggregating cells are selected in a new gate (G2). Cells in G2 are subsequently analysed for reactivity with streptavidin-PE using FSC versus FL-2 (PE channel). G3 is set to include 0.1% of (false) positive cells. Subsequently, at least 5×10e8 stained cells (twice the library size ideally more) are analysed with the settings as indicated above and the cells in G3 are sorted into a tube containing 2-3 ml SD-CAA medium. Roughly 5×10e5 cells (Pooh) are harvested in the first round of selection and propagated for 1 to 2 days, after which the cells can be stored at −80° C. and aliquots can be induced to express the Fcabs as described above. After two more days the next selection round can take place.
Second Selection Round:
Pooh 1 selected in round 1 are induced to express the Fcab on their surface as described above. At least 5×10e6 cells (comprising multiple copies of Pooh) are incubated for 30' on ice with 500 nM biotinylated antigen (Her2) in 1 ml SB. Then the cells are washed once with cold SB and subsequently incubated for 30' on ice with streptavidin-PE (from R&D systems) diluted 1 in 100 in SB together with 2 g/ml Protein A-FITC (Fluka). Next the cells are washed twice with ice cold SB and diluted to an end concentration of ~2×10e6 cells/ml. In addition, control stainings are made in which 5×10e6 cells/ml of Pooh 1 in 100 pl cells are incubated with a mixture of Prot A and streptavidin-PE as indicated above, but without the incubation with the antigen (Her2). In addition, 5×10e5 cell in 100 pl of a yeast clone expressing Fcab wt non randomized Pc fragment) is stained with Prot A-FITC as described above in the absence of streptavidin-PE. Fcab-wt expressing cells are analysed in e.g. a FACS ARIA from BD to set gates for sorting. First a FSC/SSC gate (G1) is set to identify healthy yeast cells, from Cl a FSC-width versus FSC-area plot is made and only non aggregating cells are selected in new gate (G2).

Cells in G2 are subsequently analysed for Protein A expression using FSC versus FL-1 (FITC). G3 is set to cover strong Prot A positive cells (50-60% of parent gate) and G4 is set to cover weak Prot A positive cells (20-30% of parent cells). G3+G4 will include roughly 70-80% of all cells in G2. Now the Pool cells stained for streptavidin-PE in the presence of Prot A-FITC are used to set the rest of the sorting gates. First Cl and G2 are checked with the Pool cells and if necessary adjusted. Pool cells will have lesser events in G3 and maybe also in G4 indicating that not all cells in Pooh 1 express Fcabs that are folded as the Fcab-wt. Using the control stained Pool cells a new gate is prepared both for G3 and G4. The new gates are set in a plot FSC and FL-2 (PE). Gate (G5) is prepared that includes 0.1% (false) streptavidin positive cells in G3 and the same is done for cells in G4 resulting in G6. In the next step at least 5×10e6 cells stained for Her2-biotin+streptavidin-PE and Prot A-FITC are sorted by the FACS-ARIA. Cells are collected from G5 (Pool2.1 and G6 (Pool2.2) in separate tubes containing 2-3 ml yeast culture medium. Between 10 and 1000 clones can be expected from both gates. Both new pools are propagated for 1 or 2 days and stored at −80° C. Cells from 2.1 and 2.2 may be either used for direct further sorting in a third round or they may be subjected, (preferably after mixing the two clone together again) to a round of additional randomization of the AB loop (affinity maturation) before they are further sorted in FACS.
Affinity Maturation for Selected Clones/Pools
For affinity maturation, diversity is introduced in selected clones or in pools of selected clones in the AB loop. For this purpose, a PCR is made with a primer that contained degenerate codons at positions 359, 360 and 361 (EU numbering) (primer Abmut, gaaccacaggtgtacaccctgcc-cccatccgggatgagctgnnbnnbnnbca ggtcagcctgacctgcc tggt-caaag, SEQ ID No. 26) or alternatively with a primer that contained degenerate codons at positions 358, 359, 360, 361 and 362 (EU numbering) (primer Abmut2LR, gaaccacaggt-gtacaccctgcccccatcccgggatgagnnbnnbnnbnnbnnbgtcagc ctgacctgcctggtcaaag, SEQ ID No. 27). The second primer used in these PCRs is gapfcs3 in both cases. In order to create flanking sequences for efficient gap repair in yeast, the resulting PCR products are further amplified with the primer pair gapch35 and gapfsc3 and subsequently transformed in *Saccharomyces cerevisiae* strain EBY100 by Lithiumacetate transformation together with XhoI cleaved pYD1CH12 as described above. As alternative primers for randomization of the described residues in the AB loop, primers such as AbmutIL (gaaccacaggtgtacaccctgcccccatcccgggatgagnnbnn-bnnbnnbcaggtcagc ctgacctgcctggtcaaag, SEQ ID No. 28) or AbmutIR (gaaccacaggtgta caccctgcccccatcccgggatgagctgn-nbnnbnnbnnbgtcagcctgacctgcctggtc aaag, SEQ ID No. 29) can also be used. In an analogous manner, residues in the EF loop can be randomized e.g. by total randomization or by randomization using spiked oligonucleotides as primers or by similar mutagenesis techniques. The Abmut primer will result in 8000 new variants (Pool2.3) of each clone and the Abmut2LR primer with lead to 3×10e6 new variants (Pool2.4). Therefore Pools 2.3. and 2.4 will both results in new libraries of approximately 10e8 individual since the starting material (P0012.1+2.2) already contains approximately 10-1000 clones.

Third Selection Round

Affinity matured pools 2.3 and 2.4 and if necessary Pool2.1 (only the Prot A positive cells are preferred) are induced to express Fcabs on their cell surface as described above and subsequently sorted as described for "Second selection round", with exception that the Pools 2.3 and 2.4 are much bigger and therefore staining volumes for the pools are equal to those of the library staining described in "First selection round". In the third selection round, only Her2 positive/Prot A positive cells are sorted. Pools derived from these selections contain typically >20% Her2/Prot A positive cells. If not then a fourth and fifth (or even more) round(s) of selection combining Prot A with Her2 can be performed.

Clone Analyses:

Individual clones from pools containing Her2/Prot A cells (>20% is preferred) are prepared either by plating the pools on agar plates with SD-CAA medium or by sorting the singles cells (=clones) directly from the FACS ARIA onto the plates without generating a pool. Clones are allowed to grow and are transferred to liquid cultures and stored in −80° C. Aliquots of the clones are subsequently induced to express Fcabs on their cell surface as described above and screened for a number of parameters in the FACS. These parameters may be: a dose response range of the antigen used for selection (Her2) with and without the presence of Prot A-FITC, CD64 staining as described above. In addition using similar staining protocols a number of irrelevant biotinylated antigen can be screened to identify non-cross reacting Fcabs.

It is to be expected that, after several rounds of selecting antigen (Her2)+Prot A positive cells, a large percentage of clones show >25% antigen (Her2) positivity when stained with 500 nM antigen (Her2) and >70% Prot A positivity when stained with 2 pg/ml Prot A-FITC. In most of the cases these clones will also show >50% CD64 binding. Thus mimicking the Prot A and CD64 levels of non-randomized Pc fragments (Fcab wt) expressed on yeast.

Clones selected as described above with characteristics as described above are now ready to be produced as soluble molecules. This can be done by transient transfection or by stable transfection of the Fcab DNA into new host cells. For this purpose the DNA from individual yeast clones is isolated using standard procedures. The relevant DNA coding for the complete CH3 domain or only the part of the CH3 domain that is randomized in the library is amplified by PCR and transferred into a new expression vector containing the missing part of the Fcab+a suitable promoter and one of more selection markers such as G418, that allows selection of transfected cells out of a pool of non transfected cells. The new vector is then e.g. transiently transfected into a new host cell such as HEK293 or CHO. The host cells are allowed to recover and are subsequently cultured for a number of days. The supernatant of the cultures with contain the soluble Fcab which can be used for further testing with or without purification over e.g. Prot A. Stable cell lines can also be made by standard procedures.

TABLE 2

Sequences of selected Her2 clones: with reference to numbering of Seq. ID No. 1

| Clone name | AB loop AA143ff | EF Loop AA198ff |
|---|---|---|
| Fcab wt | LTKNQ (SEQ ID No. 87) | ---------------DKSRWQQ (SEQ ID No. 88) |
| y‾Her.C2-P3.1-1 | LDNSQ (SEQ ID No. 30) | IRSSVGSRRWWS (SEQ ID No. 51) |
| y‾Her.C2-P3.1-3 | YEGSS (SEQ ID No. 31) | ARYSPRMLRWAH (SEQ ID No. 52) |
| y-Her.C2-P3.1-5 | YMSAD (SEQ ID No. 32) | SRRDSSLLRWAH (SEQ ID No. 53) |
| y‾Her.C2-P3.1-6 | YRRGD (SEQ ID No. 33) | APGSKGYRRWAL (SEQ ID No. 54) |
| y‾Her.C2-P3.1-8 | LMSRQ (SEQ ID No. 34) | DKPFWGTSRWSR (SEQ ID No. 55) |
| y‾Her.C2-P3.1-16 | LHLAQ (SEQ ID No. 35) | SINDLINHRWPY (SEQ ID No. 56) |
| y‾Her.C2-P3.1-18 | YLSKD (SEQ ID No. 36) | MWGSRDYWRWSH (SEQ ID No. 57) |
| y‾Her.C2-P3.2-3 | YRSGS (SEQ ID No. 37) | NSGSAMMVRWAH (SEQ ID No. 58) |
| y‾Her.C2-P3.2-9 | LRDGQ (SEQ ID No. 38) | QRSRLSRQRWWR (SEQ ID No. 59) |
| y‾Her.C2.P4.2-1 | YSANT (SEQ ID No. 39) | ARYSPRMLRWAH (SEQ ID No. 60) |
| y‾Her.C2.P4.2-3 | YASNT (SEQ ID No. 40) | ARYSPRMLRWAH (SEQ ID No. 61) |
| y‾Her.C2.P4.2-4 | YSDGD (SEQ ID No. 41) | ARYSPRMLRWAH (SEQ ID No. 62) |
| y‾Her.C2.P4.2-5 | YSGGS (SEQ ID No. 42) | ARYSPRMLRWAH (SEQ ID No. 63) |
| y-Her.C2.P4.2-6 | YGRDS (SEQ ID No. 43) | ARYSPRMLRWAH (SEQ ID No. 64) |
| y-Her.C2.P4.2-8 | YAGGT (SEQ ID No. 44) | ARYSPRMLRWAH (SEQ ID No. 65) |
| y‾Her.C2.P4.2-10 | YSSDS (SEQ ID No. 45) | ARYSPRMLRWAH (SEQ ID No. 66) |
| y‾Her.C2.P4.2-12 | YHSGS (SEQ ID No. 46) | ARYSPRMLRWAH (SEQ ID No. 67) |
| y‾Her.C2.P4.2-15 | YLTNS (SEQ ID No. 47) | ARYSPRMLRWAH (SEQ ID No. 68) |
| y‾Her.C2.P4.2-18 | YGSEE (SEQ ID No. 48) | ARYSPRMLRWAH (SEQ ID No. 69) |
| y‾Her.C2.P4.2-19 | YRSGE (SEQ ID No. 49) | ARYSPRMLRWAH (SEQ ID No. 70) |
| y‾Her.C2.P4.2-20 | YGTDD (SEQ ID No. 50) | ARYSPRMLRWAH (SEQ ID No. 71) |

Example 7

Yeast Display of 4D5 Fab

For the display of a Fab fragment on yeast, the yeast display vector pYD1 (Invitrogen) (SEQ ID No. 72) is modified as follows:

A NheI restriction site is introduced by site directed mutagenesis at position 581/586 to yield the modified vector pYD1Nhe (SEQ ID No. 73). This vector is restricted with NheI and PmeI, to yield 3 fragments. The largest fragment is the remaining vector backbone, in which a synthetic oligonucleotide linker is inserted to yield the vector pYD1lnk (SEQ ID No. 74). A cassette which includes the MATa transcription termination region is then amplified by PCR from the vector pYD1 and is cloned into pYD1lnk via BamHI and PstI restriction and ligation. The resulting vector is pYD1mata (SEQ ID No. 75). A cassette that contains the GAL1 promotor, the gene coding for Aga2 and a synthetic linker with NotI and SfiI cloning sites is amplified by PCR from pYD1 and cloned in pYD1mata via EcoRI and Pad restriction to yield the vector pYD1gal (SEQ. ID No. 76).

As an example for a Fab to be displayed on yeast, the genes coding for VH-CH1 and VL-CL respectively of the antibody 4D5 (Herceptin) are made synthetically (sequences 4D5H (SEQ ID No. 77) and 4D5L (SEQ ID No. 78)).

4D5H is flanked by SfiI and NotI restriction sites, and cloned into the vector pYD1gal to yield the vector pYD4D5hc (SEQ ID No. 79). In this vector, the N-terminus of 4D5H is fused to the C-terminus of Aga2, and at the C-terminus of 4D5H, a hexahistidine tag is attached, followed by the stop codon. The amino acid sequence of VH-CH1 of 4D5 is given in 4D5 hp (SEQ ID No. 80).

4D5L is flanked by NcoI and AscI restriction sites, and cloned into the vector pYD4D5hc to yield the vector pYD4D5h1 (SEQ ID No. 81). 4D5L is preceded by an Aga2 secretion signal, and carries a stop codon after the C-terminal Cysteine residue of the CL domain. The amino acid sequence of VL-CL of 4D5 is given in 4D51p (SEQ ID No. 82).

For display of the 4D5 Fab, the vector pYD4D5h1 is transformed into the yeast strain EBY100 (Invitrogen), transformants are selected on minimal medium without tryptophan, and expression of the recombinant protein is induced by growth on galactose containing medium according to standard protocols (Invitrogen).

Example 8

Construction of a Library with Randomized Residues in Structural Loops of the CL Domain of 4D5 Fab As first step in the yeast display library construction, the wildtype CL (C kappa) domain is cut out from the display vector pYD4D5h1 with restriction enzymes BsiWI and AscI. A synthetic gene encoding human C kappa domain flanked by BsiWI and AscI sites (in the context according to pYD4D5h1) is prepared in which random mutations and insertions respectively are introduced in the AB and EF loops. In this particular example, insertions of 3, 4 or 5 NNB codons are made between amino acid positions 16 and 17 of the human C kappa domain, and residue positions 92, 93, 94, 95, 97, 98 and 99 are replaced by NNB codons. (IMGT numbering, see FIG. 2). An NNB codon contains all 4 nucleotides at positions 1 and 2, and C, G and T at position 3. NNB therefore encodes all 20 naturally encoded amino acids.

The library is prepared and selected following standard procedures.

As a scaffold ligand the CDR target Her2neu and 4D5 epitope is used. Those members of the library are selected for production of a cytotoxic modular antibody according to the invention, that have a binding site engineered into the CL domain, which is specifically binding to an effector molecule, such as an Fcgamma receptor, or a half-life prolonging protein, such as serum albumin. The resulting Fab is tested for (i) Her2neu binding with a Kd<$10^{-8}$ M and an 1050<$10^{-8}$ M, and (ii) effector function using a CDC and/or ADCC assay, and alternatively to determine albumin binding.

We claim:

1. A method of producing a functional binding agent, wherein the functional binding agent binds to both a target antigen and a scaffold ligand, wherein the scaffold ligand binds to the backbone of the oligomer of modular antibody domains regardless of the target antigen specificity of the functional binding agent, wherein the functional binding agent is an antibody Fc fragment comprising a CH2 domain and a CH3 domain, with at least one structural loop region, characterized in that said at least one loop region comprises at least one amino acid modification forming at least one modified loop region, wherein said at least one modified loop region binds specifically to said target antigen, the method comprising the steps of:
   (a) providing a library of the functional binding agents by a method comprising
      (i) providing a genetic package, wherein the genetic package is yeast, and
      (ii) displaying at least two of the functional binding agents by fusing them to the outer surface of the genetic package, so that a genetic package displaying functional binding agents capable of binding both to a target antigen and to a scaffold ligand is prepared,
   (b) contacting said library with said target antigen in the presence of a scaffold ligand, wherein said target antigen and said scaffold ligand are different molecules, wherein said scaffold ligand is selected from the group consisting of CD64, CD16, CD32, FcRn and Protein A,
   (c) selecting a library member binding to said target antigen in the presence of said scaffold ligand to obtain a functional binding agent which binds to both the target antigen and the scaffold ligand, and
   (d) producing a preparation of the selected functional binding agent which binds to both the target antigen and the scaffold ligand.

2. The method of claim 1, wherein said library of the functional binding agents contains at least $10^2$ independent clones expressing oligomers of modular antibody domains.

3. The method of claim 1, wherein said library of the functional binding agents contains at least $10^6$ independent clones expressing oligomers of modular antibody domains.

4. The method of claim 1, wherein said target antigen is a receptor of the erbB class.

5. The method of claim 1, wherein said target antigen is human Her2.

6. The method of claim 1, wherein the selected functional binding agent has a molecular weight of less than 60 kD.

7. The method of claim 1, wherein the selected functional binding agent has a target antigen binding affinity of $Kd<10^{-8}$ M.

8. The method of claim 1, further comprising the steps of:
   (e) affinity maturating the selected functional binding agent by amino acid variation to obtain an affinity matured pool of binding agents, and
   (f) selecting a member of said pool which binds to the target antigen in the presence of the scaffold ligand to obtain an affinity maturated functional binding agent.

9. The method of claim 8, wherein the selected affinity maturated functional binding agent from step 8(f) exhibits at least a 10 fold increase in affinity of binding to the target antigen compared to the selected functional binding agent from step 1(c).

* * * * *